US006294531B1

(12) United States Patent
Barmore et al.

(10) Patent No.: US 6,294,531 B1
(45) Date of Patent: Sep. 25, 2001

(54) CALCILYTIC COMPOUNDS

(75) Inventors: Robert M. Barmore, Salt Lake City, UT (US); Pradip Kumar Bhatnagar, Exton, PA (US); William M. Bryan; Joelle Lorraine Burgess, both of Phoenixville, PA (US); James Francis Callahan, Philadelphia; Raul Rolando Calvo, Royersford, both of PA (US); Eric G. Del Mar, Salt Lake City, UT (US); Maria Amparo Lago, Audubon; Thomas The Nguyen, King of Prussia, both of PA (US); Derek Sheehan, Salt Lake City, UT (US); Robert Lawrence Smith, Lansdale; Linda Sue Southall, West Chester, both of PA (US); Bradford C. Van Wagenen, Salt Lake City, UT (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/402,310

(22) PCT Filed: Apr. 8, 1998

(86) PCT No.: PCT/US98/06928

§ 371 Date: Oct. 1, 1999

§ 102(e) Date: Oct. 1, 1999

(87) PCT Pub. No.: WO98/45255

PCT Pub. Date: Oct. 15, 1998

Related U.S. Application Data

(60) Provisional application No. 60/061,327, filed on Oct. 8, 1997, provisional application No. 60/061,329, filed on Oct. 8, 1997, provisional application No. 60/061,330, filed on Oct. 8, 1997, provisional application No. 60/061,333, filed on Oct. 8, 1997, provisional application No. 60/061,331, filed on Oct. 8, 1997, and provisional application No. 60/042,724, filed on Apr. 8, 1997.

(51) Int. Cl.[7] .................. C07C 255/50; C07C 311/16; C07D 295/26; C07D 295/182

(52) U.S. Cl. .................. 514/227.5; 514/237.5; 514/239.5; 514/255; 514/330; 514/331; 514/423; 514/424; 514/603; 514/619; 544/59; 544/159; 544/162; 544/165; 544/383; 544/386; 546/226; 546/232; 548/539; 548/542; 558/390; 564/86

(58) Field of Search .................. 564/220, 349, 564/86; 558/390; 544/59, 159, 162, 165, 383, 386; 546/232, 226; 548/539, 542; 514/227.5, 237.5, 239.5, 255, 330, 331, 423, 424, 603, 619

(56) References Cited

U.S. PATENT DOCUMENTS

| 3,634,511 | * | 1/1972 | Howe et al. | 564/220 |
| 3,712,927 |   | 1/1973 | Howe et al. | 560/46 |
| 4,165,384 |   | 8/1979 | Enar et al. | 424/324 |
| 5,064,863 |   | 11/1991 | Alig et al. | 514/653 |
| 5,166,218 |   | 11/1992 | Alig et al. | 514/652 |
| 6,022,894 | * | 2/2000 | Del Mar et al. | 514/524 |

FOREIGN PATENT DOCUMENTS

| 298506 | 2/1992 | (DE) . |
| 0459298 | 12/1991 | (EP) . |
| 9737967 | 10/1997 | (WO) . |

OTHER PUBLICATIONS

D. H. Copp, et al., "Endocrine Regulation of Calcium Metabolism", (1970), Annual Review of Physiology, vol. 32, pp. 61–86.
Garrido et al., Chemical Abstracts, 97:38575, 1982.*
Haenel et al., Chemical Abstracts, 124:193365, 1996.*
Ibanez–Paniello, Chemical Abstracts, 87:151825, 1977.*

* cited by examiner

Primary Examiner—Fiona T. Powers
(74) Attorney, Agent, or Firm—Soma G. Simon; William T. King; Charles M. Kinzig

(57) ABSTRACT

Novel arylalkylamino compounds exhibiting calcilytic properties are provided.

8 Claims, No Drawings

CALCILYTIC COMPOUNDS

This is a 371 of International Application PCT/US98/06928, filed Apr. 8, 1998, which claims benefit from the following Provisional Applications: 60/042,724, Apr. 8, 1997; 60/061,327, Oct. 8, 1997; 60/061,329, Oct. 8, 1997; 60/061,330, Oct. 8, 1997; 60/061,333, Oct. 8, 1997; 60/061,331, Oct. 8, 1997.

The present invention relates to novel arylalkylamine calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., *Nature* 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., *Cell Calcium* 11:319, 1990. For example, extracellular $Ca^{2+}$ plays a role in parafollicular (C-cells) and parathyroid cells. See Nemeth, *Cell Calcium* 11:323, 1990. The role of extracellular $Ca^{2+}$ on bone osteoclasts has also been studied. See Zaidi, *Bioscience Reports* 10:493, 1990.

Various compounds are known to mimic the effect of extra-cellular $Ca^{2+}$ on a calcium receptor. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators which are active at $Ca^{2+}$ receptors. Such calcilytics are useful in the treatment of various disease states characterized by abnormal levels of one or more components, e g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention comprises arylalkylamine derivatives represented by Formula (I) and their use as calcium receptor antagonists which are useful in the treatment of a variety of diseases associated with abnormal bone or mineral homeostasis, including but not limited to hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present compounds maintain calcium receptor activity and selectivity while having minimal affinity for the beta adrenergic receptor.

The present invention further provides a method for antagonizing calcium receptors in an animal, including humans, which comprises administering to an animal in need thereof an effective amount of a compound of Formula (I).

DETAILED DESCRIPTION OF THE INVENTION

The compounds of the present invention are represented by structural Formula (I):

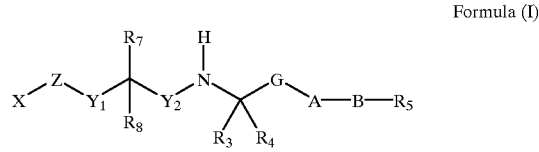

Formula (I)

wherein:

$Y_1$ is a covalent bond, alkylene or alkenylene of up to 4 carbon atoms, unsubstituted or substituted by $C_{1-4}$ alkyl;

$Y_2$ is methylene, unsubstituted or substituted by $C_{1-4}$ alkyl or $CF_3$;

Z is selected from the group consisting of a covalent bond, O, S, NH, N—$C_{1-4}$ alkyl, $O(CH_2)_n$, $(CH_2)_nO$, NR'" C=O and C=ONR'", where R'" is $C_{1-4}$ alkyl and n is an integer from 1 to 3, $R_3$ and $R_4$ are, independently, methyl or ethyl, or, together, form cyclopropyl;

$R_5$ is phenyl or naphthyl, unsubstituted or substituted with one or more substituents selected from the group consisting of OH, $C_{1-4}$alkyl, halo, $CH(CH_3)_2$, halo $C_{1-4}$ alkyl, $C_{1-4}$ alkoxy, $C_{3-6}$ cycloalkyl, $OSO_2R^{IV}$, CN, $NO_2$, $OCF_3$, $CF_3$, and $CH_2CF_3$, wherein $R^{IV}$ represents $C_{1-4}$ alkyl or $C_{3-6}$ cycloalkyl;

G is a covalent bond or C—$R_6$ wherein $R_6$ is H, OH or O (forming a carbonyl moiety);

$R_7$ is H, OH, or O—$C_{1-4}$ alkyl;

$R_8$ is H or $C_{1-4}$ alkyl; or $R_7$ and $R_8$ together form a carbonyl moiety; the —A—B— moiety is represented by $CH_2CH_2$, a covalent bond, —CH=CH— or —C≡C—; and X is selected from the group consisting of sub-formulae (Ia), (Ib), (Ic) (Id) and (Ie) hereinbelow:

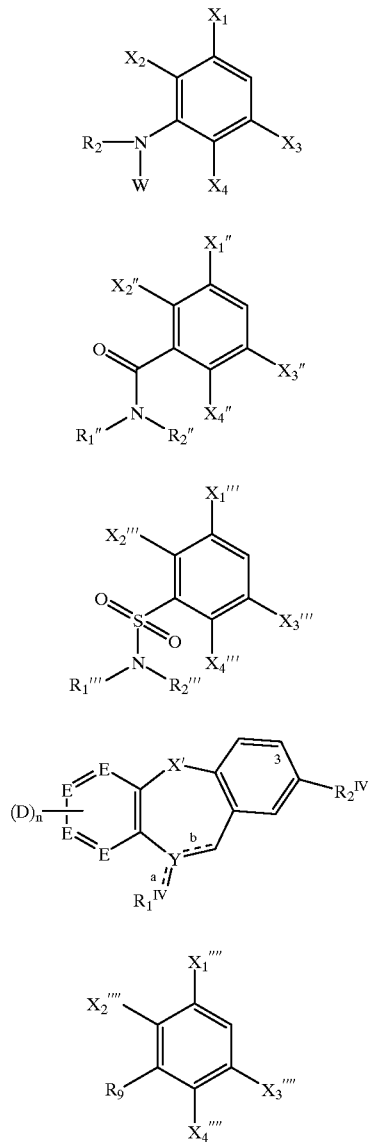

wherein:

in sub-formula (Ia):

W is selected from the group consisting of $R_1$, $SO_2R_1$, $C(O)R_1$, $SO_2NR_1R_1'$, $C(O)NR_1R_1'$, $C(O)OR_1SO_3R_1'$, wherein $R_1$ and $R_1'$ are independently selected from the group consisting of hydrogen, $C_{1-4}$ alkyl, $C_{3-6}$ cycloalkyl, $C_{2-5}$ alkenyl, $C_{2-5}$ alkynyl, heterocycloalkyl aryl and aryl $C_{1-4}$ alkyl; or $R_1$ and $R_1'$ together form a 3 to 7 membered optionally substituted heterocyclic ring; wherein any substituents are selected from the group consisting of CN, aryl, $CO_2R$, $CO_2NHR$, OH, OR, $NH_2$, halo, $CF_3$, $OCF_3$ and $NO_2$; wherein R represents $C_{1-4}$ alkyl, or $C_{3-6}$ cycloalkyl;

$X_1$ is selected from the group consisting of CN, $NO_2$, Cl, F, Br, I, H, R', OR', $CF_3$, $OCF_3$ and $OSO_2R'$, wherein R' represents $C_{1-4}$ alkyl, or $C_{3-6}$ cycloalkyl;

$X_2$, $X_3$ and $X_4$ are, independently, selected from the group consisting of CN, $NO_2$, Cl, F, Br, I, H, R'', OR'', $CF_3$, $OCF_3$ and $OSO_2R''$, wherein R' is $C_{1-4}$ alkyl or haloalkyl; or $X_1$ and $X_2$ together form an aryl or heteroaryl ring, substituted or unsubstituted; wherein the heteroatom is selected from N, S and O; and any substituents are selected from the group consisting of halo, $C_{1-4}$ alkyl, $OCF_3$, $CF_3$, OMe, CN, $OSO_2R'$ and $NO_2$; or $X_3$ and $X_4$ independently represent $C(O)R_1$; provided that when there are multiple halo substitutions in the haloalkyl, halo represents F; also provided that either $X_1$ or $X_3$ is hydrogen; and $R_2$ is selected from the group consisting of hydrogen, $C_{1-4}$ alkyl, $C_{3-6}$ cycloalkyl, $C_{2-5}$ alkenyl, $C_{2-5}$ alkynyl, heterocycloalkyl aryl and aryl-$C_{1-4}$ alkyl;

in sub-formula (Ib):

$X_1'$ is selected from the group consisting of CN, $NO_2$, Cl, F, Br, I, H, R, OR, $CF_3$, $OCF_3$ and $OSO_2R$, wherein R represents $C_{1-4}$ alkyl, or $C_{3-6}$ cycloalkyl;

$X_2''$, $X_3''$ and $X_4''$ are, independently, selected from the group consisting of CN, $NO_2$, Cl, F, Br, I, H, R', OR', $CF_3$, $OCF_3$ and $OSO_2R'$, wherein R' is $C_{1-4}$ alkyl or haloalkyl; provided that when there are multiple halo substitutions in the haloalkyl, halo represents F, or $X_1''$ and $X_2''$ together form an aryl or heteroaryl ring, substituted or unsubstituted; wherein the heteroatom is selected from N, S and O and any substituents are selected from the group consisting of halo, $C_{1-4}$ alkyl, $OCF_3$, $CF_3$, OMe, CN, $OSO_2$-$C_{1-4}$ alkyl, $OSO_2$-$C_{3-6}$ cycloalkyl and $NO_2$;

or $X_3''$ and $X_4''$ independently represent $C(O)R_1$; provided that either $X_1''$ or $X_3''$ is hydrogen; and $R_1''$ and $R_2''$ are, independently, selected from the group consisting of hydrogen, $C_{1-4}$ alkyl, $C_{3-6}$ cycloalkyl, $C_{2-5}$ alkenyl, $C_{2-5}$ alkynyl, heterocycloalkyl and aryl; or $R_1''$ and $R_2''$ together form a 3 to 7 membered optionally substituted heterocyclic ring, optionally containing an additional heteroatom selected from O, S and N; wherein any substituents are selected from the group consisting of CN, aryl, $CO_2R''$, $CO_2NHR''$, OH, OR'', $NH_2$, halo, $CF_3$, $OCF_3$ and $NO_2$; wherein R'' represents $C_{1-4}$ alkyl, or $C_{3-6}$ cycloalkyl;

in sub-formula (Ic):

$X_1'''$ is selected from the group consisting of CN, $NO_2$, Cl, F, Br, I, H, R, OR, $CF_3$, $OCF_3$ and $OSO_2R$, wherein R represents $C_{1-4}$ alkyl, or $C_{3-6}$ cycloalkyl;

$X_2'''$, $X_3'''$, and $X_4'''$ are, independently, selected from the group consisting of CN, $NO_2$, Cl, F, Br, I, H, R', OR', $CF_3$, $OCF_3$ and $OSO_2R'$, wherein R' is $C_{1-4}$ alkyl or haloalkyl; provided that when there are multiple halo substitutions in the haloalkyl, halo represents F; or $X_1'''$ and $X_2'''$ together form an aryl or heteroaryl ring, substituted or unsubstituted; wherein the heteroatom is selected from N, S and O and the substituents are selected from the group consisting of halo, $C_{1-4}$ alkyl, $OCF_3$, $CF_3$, OMe, CN, $OSO_2$-$C_{1-4}$ alkyl, $OSO_2$-$C_{3-6}$ cycloalkyl and $NO_2$; or $X_3'''$ and $X_4'''$ independently represent $C(O)R_1$; provided that either $X_1'''$ or $X_3'''$ represents hydrogen; and $R_1'''$ and $R_2'''$ are, independently, selected from the group consisting of hydrogen, $C_{1-4}$ alkyl, $C_{3-6}$ cycloalkyl, $C_{2-5}$ alkenyl, $C_{2-5}$ alkynyl, heterocycloalkyl and aryl; or $R_1'''$ and $R_2'''$ together form a 3 to 7 membered optionally substituted heterocyclic ring, optionally containing an additional heteroatom selected from O, S and N; wherein the substituents are selected from the group consisting of CN, aryl, $CO_2R''$, $CO_2NHR''$, OH, $OR''$, $NH_2$, halo, $CF_3$, $OCF_3$ pand $NO_2$;

wherein R" represents $C_{1-4}$ alkyl, or $C_{3-6}$ cycloalkyl;

in sub-formula (Id):

D is selected from the group consisting of CN, $NO_2$, Cl, F, Br, I, R, OR, SR, $CF_3$, $OCF_3$ and $OSO_2R$, wherein R represents $C_{1-4}$ alkyl, $C_{3-6}$ cycloalkyl, or $C_{1-10}$ aryl or heteroaryl wherein the heteroatom is selected from N, S and O and substituents are selected from the group consisting of halo, $C_{1-4}$ alkyl, $OCF_3$, $CF_3$, OMe, CN, $OSO_2$-$C_{1-4}$ alkyl, $OSO_2$-$C_{3-6}$ cycloalkyl and $NO_2$;

n is the integer 1 or 2;

each E is independently C or N, provided that no more than two E moieties are N; further provided that when n is 2, each E is C;

a and b are optionally present bonds;

$R_1^{IV}$ is selected from the group consisting of $(CH_2)_nCO_2R'$, $(CH_2)_nCO_2H$, $(CH_2)_nCONR'_2$, $(CH_2)_nCH_2OR'$, OR', SR', CN, $NO_2$, Cl, F, Br, I, $CF_3$, $OCF_3$, $OSO_2R'$, R' and H; wherein R' represents $C_{1-4}$ alkyl, or $C_{3-6}$ cycloalkyl;

or $R_1^{IV}$ is O, forming a ketone such that Y $R_1^{IV}$ represents —C=O;

$R_2^{IV}$ is selected from the group consisting of hydrogen, CN, $NO_2$ Cl, F, Br, I, H, R", OR", $CF_3$, $OCF_3$, and $OSO_2R''$; wherein R" represents $C_{1-4}$ alkyl, or $C_{3-6}$ cycloalkyl;

Y is selected from the group consisting of C, CH, O, N and S; provided that when Y is S, $R_1^{IV}$ is O; further provided that when Y is O, $R_1^{IV}$ is not present;

X' is selected from the group consisting of $CH_2$, NH, O and S; and attachment is at the carbon atom marked 3;

in sub-formula (Ie):

$X_1''''$ is selected from the group consisting of CN, $NO_2$, Cl, F, Br, I, H, R', OR', $CF_3$, $OCF_3$ and $OSO_2R'$, wherein R' represents $C_{1-4}$ alkyl, or $C_{3-6}$ cycloalkyl;

$X_2''''$, $X_3''''$ and $X_4''''$ are, independently, selected from the group consisting of CN, $NO_2$, Cl, F, Br, I, H, R", OR", $CF_3$, $OCF_3$ and $OSO_2R''$, wherein R" is $C_{1-4}$ alkyl or haloalkyl; or $X_1''''$ and $X_2''''$ together form an aryl or heteroaryl ring, substituted or unsubstituted; wherein the heteroatom is selected from N, S and O; and any substituents are selected from the group consisting of halo, $C_{1-4}$ alkyl, $OCF_3$, $CF_3$, OMe, CN, $OSO_2R'$ and $NO_2$; or $X_3''''$ and $X_4''''$ independently represent $C(O)R_1$; provided that when there are multiple halo substitutions in the haloalkyl, halo represents F; also provided that either $X_1''''$ or $X_3''''$ is hydrogen; and $R_9$ is selected from the group consisting of O—$CH_2$-alkyl, O—$CH_2$-aryl and O-aryl.

Preferably, the compounds of the present invention are represented by Formula (II) hereinbelow:

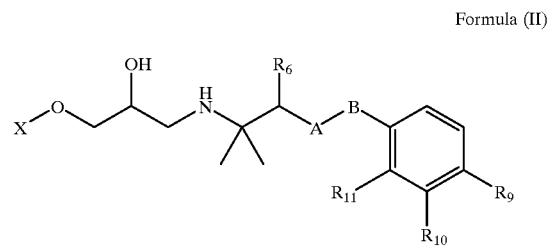

Formula (II)

wherein:

$R_9$ is selected from the group consisting of H, OH, $OCH_3$, Cl, F, $CH_3$, $CH_2CH_3$ and $CH(CH_3)_2$;

$R_{10}$ is selected from the group consisting of H, Cl, F, $CF_3$ and $CH_3$;

or $R_9$ and $R_{10}$ form an optionally substituted fused phenyl ring; and $R_{11}$ is selected from methyl, H or F.

More preferably, $R_6$ is H, or OH. More preferably, $R_9$ is selected from the group consisting of $OCH_3$, Cl, F, $CH_3$, $CH_2CH_3$ and $CH(CH_3)_2$. More preferably, $R_{10}$ is selected from the group consisting of H, Cl, F, and $CH_3$; or $R_9$ and $R_{10}$ form a fused aryl ring. More preferably, $R_{11}$ is H or F. More preferably, the —A—B— moiety represents —CH=CH—.

More preferably still, $R_6$ is H. More preferably still, $R_9$ is selected from the group consisting of $OCH_3$, Cl, $CH_3$, $CH_2CH_3$, and $CH(CH_3)_2$. More preferably still, $R_{10}$ is H; $R_{11}$ is H; or $R_9$ and $R_{10}$ together form a fused aryl ring.

Most preferably, $R_9$ is $OCH_3$ or $CH_2CH_3$.

In sub-formula (Ia), preferably, $X_1$ is selected from the group consisting of CN, $NO_2$, Cl, F, Br, I and H. Preferably, $X_2$, $X_3$ and $X_4$ are, independently, selected from the group consisting of Cl, F, Br, I and H. Preferably, $R_1$, $R_1'$ and $R_2$ are, independently, selected from the group consisting of $C_{1-4}$ alkyl, $C_{3-6}$ cycloalkyl, heterocycloalkyl, aryl or aryl$C_{1-4}$alkyl.

In sub-formula (Ia), more preferably, $R_1$, $R_1'$ and $R_2$ are, independently, H, alkyl, or aryl. More preferably, $X_1$ is selected from the group consisting of CN, $NO_2$, Cl, F, Br, I and H. More preferably, $X_2$, $X_3$ and $X_4$ are, independently, selected from the group consisting of Cl, F, Br, I and H.

In sub-formula (Ia), more preferably still, $R_1$, $R_1'$ and $R_2$ are, independently, $C_{1-4}$ alkyl, or aryl. More preferably still, $X_1$ is CN, $NO_2$, or Cl. More preferably still, $X_2$ is Cl, or H. More preferably still, $X_3$ and $X_4$ are H.

In sub-formula (Ia), most preferably, $X_1$ is CN, or $NO_2$. Most preferably, $X_2$ is Cl.

In sub-formula (Ib), preferably, $X_1''$ is selected from the group consisting of CN, $NO_2$, Cl, F, Br, I and H. Preferably, $X_2''$, $X_3''$ and $X_4''$ are, independently, selected from the group consisting of Cl, F, Br, I and H. Preferably, $R_1''$ and $R_2''$ are, independently, selected from the group consisting of $C_{1-4}$ alkyl, $C_{3-6}$ cycloalkyl, heterocycloalkyl or aryl; or $R_1''$ and $R_2''$ together form an optionally substituted 3–7 membered ring.

In sub-formula (Ib), more preferably, $R_1''$ and $R_2''$ are, independently, H, $C_{1-4}$ alkyl, or aryl; or $R_1''$ and $R_2''$ together form an optionally substituted 4–7 membered ring. More preferred substituents when the heteroatom is N include acyl, $C_{1-4}$ alkyl, and aryl. More preferably, $X_1''$ is selected from the group consisting of CN, $NO_2$, Cl, F, Br, I and H. More preferably, $X_2''$ is selected from the group consisting of Cl, F, Br, I and H.

In sub-formula (Ib), more preferably still, $R_1''$ and $R_2''$ are, independently, $C_{1-4}$ alkyl, or aryl; or $R_1''$ and $R_2''$ together form a 4–7 membered ring as described hereinabove. More preferably still, $X_1''$ is CN, $NO_2$, or Cl. More preferably still, $X_2''$ is Cl, or H.

In sub-formula (Ib), most preferably, $R_1''$ and $R_2''$ together form a 4–7 membered ring as described hereinabove. Most preferably, $X_1''$ is CN, or $NO_2$. Most preferably, $X_2''$ is Cl.

In sub-formula (Ic), preferably, $X_1'''$ is selected from the group consisting of CN, $NO_2$, Cl, F, Br, I and H. Preferably, $X_2'''$, $X_3'''$ and $X_4'''$ are, independently, selected from the group consisting of Cl, F, Br, I and H. Preferably, $R_1'''$ and $R_2'''$ are, independently, selected from the group consisting of $C_{1-4}$ alkyl, $C_{3-6}$ cycloalkyl, heterocycloalkyl or aryl; or $R_1'''$ and $R_2'''$ together form an optionally substituted 3–7 membered ring.

In sub-formula (Ic), more preferably, $R_1'''$, and $R_2'''$ are, independently, H, $C_{1-4}$ alkyl, or aryl; or $R_1'''$ and $R_2'''$ together form an optionally substituted 4–7 membered ring, optionally containing a heteroatom selected from O, S, and N. More preferred substituents when the heteroatom is N include acyl, $C_{1-4}$ alkyl, and aryl. More preferably, $X_1'''$ is selected from the group consisting of CN, $NO_2$, Cl, F, Br, I and H. More preferably, $X_2'''$, $X_3'''$ and $X_4'''$ are, independently, selected from the group consisting of Cl, F, Br, I and H.

In sub-formula (Ic), more preferably still, $R_1'''$ and $R_2'''$ are, independently, $C_{1-4}$ alkyl, or aryl; or $R_1'''$ and $R_2'''$ together form a 4–7 membered ring as described hereinabove. More preferably still, $X_1'''$ is CN, $NO_2$, or Cl. More preferably still, $X_2'''$ is Cl or H. More preferably still, $X_3'''$ and $X_4'''$ are H.

In sub-formula (Ic), most preferably, $R_1'''$ and $R_2'''$ together form a 4–7 membered ring as described hereinabove. Most preferably, $X_1'''$ is CN or $NO_2$. Most preferably, $X_2'''$ is Cl.

In sub-formula (Id), preferably, D is selected from the group consisting of Br, I, Cl and F, R, OR, SR, and H. Preferably, $R_1^{IV}$ is selected from the group consisting of $(CH_2)_nCO_2R'$, $(CH_2)_nCO_2H$, $(CH_2)_nCONR'_2$, $(CH_2)_nCH_2OR'$, OR', SR', R' and H; wherein R' is $C_{1-4}$ alkyl or $C_{3-6}$ cycloalkyl; or $R_1^{IV}$ is O, forming a ketone such that Y $R_1^{IV}$ represents —C=O. Preferably, $R_2^{IV}$ is selected from the group consisting of hydrogen, CN, $NO_2$, Cl, Br, F and I;

In sub-formula (Id), more preferably, D is H. More preferably, each E is C. More preferably, X' is $CH_2$, O, or NH. More preferably, Y is C or N. More preferably, $R_1^{IV}$ is $CH_2CO_2R'$, SR', or O, forming a ketone. More preferably, $R_2^{IV}$ is selected from the group consisting of CN, $NO_2$, Cl, and H.

In Formula (Id), more preferably still, X' is $CH_2$ or O. More preferably still, $R_1^{IV}$ is $CH_2CO_2R'$ or SR'. More preferably still, $R_2^{IV}$ is H, CN, or $NO_2$.

In Formula (Id), most preferably, X' is $CH_2$. Most preferably, Y is C. Most preferably, $R_2^{IV}$ is CN or $NO_2$.

As used herein, "alkyl" refers to an optionally substituted hydrocarbon group joined by single carbon-carbon bonds. The alkyl hydrocarbon group may be linear, branched or cyclic, saturated or unsaturated cyclic, saturated or unsaturated. The substituents are selected from aryl, F, Cl, Br, I, $N(R)_2$, SR and OR, wherein R represents $C_{1-4}$ alkyl or $C_{3-6}$ cycloalkyl, unless otherwise indicated. Preferably, no more than three substituents are present. Preferably, the alkyl group is unsubstituted. Preferably, the alkyl group is linear. Preferably, the alkyl group is saturated. Preferably, the alkyl group is unsubstituted.

As used herein "cycloalkyl" refers to optionally substituted 3–7 membered carbocyclic rings wherein any substituents are selected from the group consisting of, F, Cl, Br, I, $N(R)_2$, SR and OR, wherein R represents $C_{1-4}$ alkyl or $C_{3-6}$ cycloalkyl, unless otherwise indicated.

As used herein "heterocycloalkyl" refers to optionally substituted 4, 5, 6 or 7 membered heterocyclic rings containing 1 to 2 heteroatoms selected from N, O, and S.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Preferred aryl include phenyl and naphthyl. More preferred aryl include phenyl. Preferred substituents are selected from the group consisting of halo, $C_{1-4}$ alkyl, $OCF_3$, $CF_3$ OMe, CN, $OSO_2$ R and $NO_2$, wherein R represents $C_{1-4}$ alkyl or $C_{3-6}$ cycloalkyl.

As used herein, "acyl" refers to $C_{1-4}$ alkylcarbonyl.

As used herein, "alkenyl" refers to an optionally substituted hydrocarbon group containing at least one carbon-carbon double bond and containing up to 5 carbon atoms joined together. The alkenyl hydrocarbon chain may be straight, branched or cyclic. Any substituents are selected from the group consisting of halo, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl. Preferably, the alkenyl group is unsubstituted.

As used herein, "alkynyl" refers to an optionally substituted hydrocarbon group containing at least one carbon-carbon triple bond between the carbon atoms and containing up to 5 carbon atoms joined together The alkynyl hydrocarbon group may be straight-chained, branched or cyclic. Any substituents are selected from the group consisting of halo, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl. Preferably, the alkynyl group is unsubstituted.

The compounds of the present invention may contain one or more asymmetric carbon atoms and may exist in racemic and optically active forms. All of these compounds and diastereomers are contemplated to be within the scope of the present invention.

Preferred compounds of the present invention include the following compounds:

(R)-3-[2-cyano-4-[N-benzyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[methylsulfonyl]amino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(4-methoxyphenyl)ethylamino]-propan-2-ol;

(R)-3-[2-cyano-4-[N-methylsulfonylamino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(2-naphthyl)ethylamino]-propan-2-ol;

(R)-3-[2-cyano-4-[N-[methylsulfonyl]amino]phenoxy]-1-[1,1-dimethyl-2-(2-naphthyl)ethylamino]-propan-2-ol;

(R)-3-[2-cyano-4-[N-benzyl-N-[4-methylphenylsulfonyl]amino]phenoxy]-1-[1,1-dimethyl-2-(2-naphthyl)ethylamino]-propan-2-ol;

(R)-3-[2-cyano-4-[N-benzyl-N-[4-methylphenylsulfonyl]
amino]phenoxy]-1-[1,1-dimethyl-2-(benzyloxy)
ethylamino]-propan-2-ol;
(R)-3-[2-cyano-4-[N-benzyl-N-[4-methylphenylsulfonyl]
amino]phenoxy]-1-[1,1-dimethyl-3-phenylpropylamino]-
propan-2-ol;
(R)-3-[2-cyano-4-[N-benzyl-N-[4-methylphenylsulfonyl]
amino]phenoxy]-1-[1,1-dimethyl-4-phenylbutylamino]-
propan-2-ol;
(R)-3-[2-cyano-4-[N-benzyl-N-ethylcarbonyl]phenoxy]-1-
[1,1-dimethyl-2-(2-naphthyl)ethylamino]-propan-2-ol;
(R)-3-[2-cyano-4-[N-benzyl-N'-morpholino]ureido]
phenoxy]-1-[1,1-dimethyl-2-(2-naphthyl)ethylamino]-
propan-2-ol;
(R)-3-[2-cyano-4-[N-benzyl-N'-morpholino]ureido]
phenoxy]-1-[1,1-dimethyl-2-(4-methoxyphenyl)
ethylamino]-propan-2-ol;
(R)-3-[2-cyano-4-[N-methyl-N'-morpholino]ureido]
phenoxy]-1-[1,1-dimethyl-2-(2-naphthyl)ethylamino]-
propan-2-ol;
(R)-3-[2-cyano-4-[N-methyl-N'-morpholino]ureido]
phenoxy]-1-[1,1-dimethyl-2-(4-methoxyphenyl)
ethylamino]-propan-2-ol;
(R)-1-[1,1-dimethyl-2-(4-methoxyphenyl)ethylamino]-3-
[2-cyano-4-(N,N-dipropylaminocarbonyl)phenoxy]-
propan-2-ol;
(R)-1-[1,1-dimethyl-2-(4-methoxyphenyl)ethylamino]-3-
[2-cyano-4-(N-propylaminocarbonyl)phenoxy]-propan-
2-ol;
(R)-1-[1,1-dimethyl-2-(4-methoxyphenyl)ethylamino]-3-
[2-cyano-4-(N-piperidinylcarbonyl)phenoxy]-propan-2-
ol;
(R)-1-[1,1-dimethyl-2-(4-methoxyphenyl)ethylamino]-3-
[2-cyano-4-(N-morpholinylcarbonyl)phenoxy]-propan-2-
ol;
(R)-1-[1,1-dimethyl-2-(4-methoxyphenyl)ethylamino]-3-[2,
3-dichloro-4-(N-morpholinylcarbonyl)phenoxy]-propan-
2-ol;
(R)-1-[1,1-dimethyl-2-(2-naphthyl)ethylamino]-3-[2,3-
dichloro-4-(N-morpholinylcarbonyl)phenoxy]-propan-2-
ol;
(R)-1-[1,1-dimethyl-2-(4-methoxyphenyl)ethylamino]-3-[2,
3-dichloro-4-(N,N-dipropylaminocarbonyl)phenoxy]-
propan-2-ol;
(R)-1-[1,1-dimethyl-2-(2-naphthyl)ethylamino]-3-[2,3-
dichloro-4-(N,N-dipropylaminocarbonyl)phenoxy]-
propan-2-ol;
(R)-1-[1,1-dimethyl-2-(4-methoxyphenyl)ethylamino]-3-
[2-cyano, 3-chloro-4-(N-morpholinylcarbonyl)phenoxy]-
propan-2-ol;
(R)-1-[1,1-dimethyl-2-(2-naphthyl)ethylamino]-3-[2-cyano,
3-chloro-4-(N-morpholinylcarbonyl)phenoxy]-propan-2-
ol;
(R)-1-[1,1-dimethyl-2-(4-methoxyphenyl)ethylamino]-3-
[2-cyano, 3-chloro-4-(N,N-dipropylaminocarbonyl)
phenoxy]-propan-2-ol;
(R)-1-[1,1-dimethyl-2-(2-naphthyl)ethylamino]-3-[2-cyano,
3-chloro-4-(N,N-dipropylaminocarbonyl)phenoxy]-
propan-2-ol;
(R)-1-[1,1-dimethyl-2-(4-methoxyphenyl)ethylamino]-3-
[2-cyano-4-(N-pyrrolidinylcarbonyl)phenoxy]-propan-2-
ol;
(R)-1-[1,1-dimethyl-2-(4-methoxyphenyl)ethylamino]-3-
[2-cyano-4-(N-piperazinylcarbonyl)phenoxy]-propan-2-
ol;
(R)-1-[1,1-dimethyl-2-(2-naphthyl)ethylamino]-3-[2-
cyano-4-(N,N-dipropylaminocarbonyl)phenoxy]-propan-
2-ol;
(R)-1-[1,1-dimethyl-2-(2-naphthyl)ethylamino]-3-[2-
cyano-4-(N-piperidinylcarbonyl)phenoxy]-propan-2-ol;
(R)-1-[1,1-dimethyl-2-(2-naphthyl)ethylamino]-3-[2-
cyano-4-(N-morpholinylcarbonyl)phenoxy]-propan-2-ol;
(R)-1-[1,1-dimethyl-2-(2-naphthyl)ethylamino]-3-[2-
cyano-4-(N-piperazinylcarbonyl)phenoxy]-propan-2-ol;
(R)-1-1,1-dimethyl-2-(2-naphthyl)ethylamino]-3-[2-cyano-
4-(N-pyrrolidinylcarbonyl)phenoxy]-propan-2-ol;
(R)-1-[1,1-dimethyl-3-(phenyl)propylamino]-3-[2-cyano-4-
(N,N-dipropylaminocarbonyl)phenoxy]-propan-2-ol;
(R)-1-[1,1-dimethyl-4-(phenyl)butylamino]-3-[2-cyano-4-
(N,N-dipropylaminocarbonyl)phenoxy]-propan-2-ol;
(R)-1-[1,1-dimethyl-3-(phenoxy)propylamino]-3-[2-cyano-
4-(N,N-dipropylaminocarbonyl)phenoxy]-propan-2-ol;
and
(R)-1-[1,1-dimethyl-2-(oxybenzyl)ethylamino]-3-[2-cyano-
4-(N,N-dipropylaminocarbonyl)phenoxy]-propan-2-ol.
N-[3-(3-chloro-2-cyano-4-dipropylsulfamoyl)phenoxy-2
(R)-hydroxypropyl]-2-(4-methoxyphenyl)-1,1-
dimethylethylamine;
N-[3-(2,3-dichloro-4-dipropylsulfamoyl)phenoxy-2(R)-
hydroxypropyl]-2-(2,3-dichlorophenyl)-1,1-
dimethylethylamine;
N-[3-(3-chloro-2-cyano-4-dimethylsulfamoyl)phenoxy-2
(R)-hydroxypropyl]-2-(4-methoxyphenyl)-1,1-
dimethylethylamine;
N-[3-(2,3-dichloro-4-morpholinosulfamyl)phenoxy-2(R)-
hydroxypropyl]-2-(4-methoxyphenyl)-1,1-
dimethylethylamine;
N-[3-(3-chloro-2-cyano-4-morpholinosulfamyl)phenoxy-2
(R)-hydroxypropyl]-2-(4-methoxyphenyl)-1,1-
dimethylethylamine;
N-[3-(3-chloro-2-cyano-4-pyrrolidinosulfamyl)phenoxy-2
(R)-hydroxypropyl]-2-(4-methoxyphenyl)-1,1-
dimethylethylamine;
N-[3-(3-chloro-2-cyano-4-pyrrolidinosulfamyl)phenoxy-2
(R)-hydroxypropyl]-2-(2-naphthyl)-1,1-
dimethylethylamine;
N-[3-(3-chloro-2-cyano-4-morpholinosulfamyl)phenoxy-2
(R)-hydroxypropyl]-2-(2-naphthyl)-1,1-
dimethylethylamine;
N-[3-(3-chloro-2-cyano-4-thiomorpholinosulfamyl)
phenoxy-2(R)-hydroxypropyl]-2-(2-naphthyl)-1,1-
dimethylethylamine;
N-[3-(3-chloro-2-cyano-4-thiomorpholinosulfamyl)
phenoxy-2(R)-hydroxypropyl]-2-(4-methoxyphenyl)-1,
1-dimethylethylamine;
N-[3-[3-chloro-2-cyano-4-(2'-cyanoeth-1-yl)-
cyclopropylsulfamoyl]phenoxy-2(R)-hydroxypropyl]-2-
(4-methoxyphenyl)-1,1-dimethylethylamine;
N-[3-[3-chloro-2-cyano-4-(2'-cyanoeth-1-yl)-
cyclopropylsulfamoyl]phenoxy-2(R)-hydroxypropyl]-2-
(2-napthyl)-1,1-dimethylethylamine;
N-[3-[3-chloro-2-cyano-4-(benzyl-cyclopropyl)sulfamoyl]
phenoxy-2(R)-hydroxypropyl]-2-(2-napthyl)-1,1-
dimethylethylamine;
N-[3-[3-chloro-2-cyano-4-(benzyl-cyclopropyl)sulfamoyl]
phenoxy-2(R)-hydroxypropyl]-2-(4-methoxyphenyl)-1,
1-dimethylethylamine;
N-[3-[3-chloro-2-cyano-4-(4'-N-t-
butoxycarbonylpiperazino)sulfamyl]phenoxy-2(R)-
hydroxypropyl]-2-(4-methoxyphenyl)-1,1-
dimethylethylamine;
N-[3-[3-chloro-2-cyano-4-(4'-N-t-
butoxycarbonylpiperazino)sulfamyl]phenoxy)-2(R)-
hydroxypropyl]-2-(2-naphthyl)-1,1-dimethylethylamine;
N-[3-(2,3-dichloro-4-dipropylsulfamoyl)phenoxy-2(R)-
hydroxypropyl]-2-(2-naphthyl)-1,1-dimethylethylamine;

N-[3-(2,3-dichloro-4-pyrrolidinolsulfamoyl)phenoxy-2(R)-hydroxypropyl]-2-(4-methoxyphenyl)-1,1-dimethylethylamine;

N-[3-(2,3-dichloro-4-pyperidinolsulfamoyl)phenoxy-2(R)-hydroxypropyl]-2-(4-methoxyphenyl)-1,1-dimethylethylamine;

N-[3-(2,3-dichloro-4-cyclopropylsuffamoyl)phenoxy-2(R)-hydroxypropyl]-2-(4-methoxyphenyl)-1,1-dimethylethylamine;

N-[3-(2,3-dichloro-4-dipropylsulfamoyl)phenoxy-2(R)-hydroxypropyl]-2-(4-methoxyphenyl)-1,1-dimethylethylamine;

N-[3-(2,3-dichloro-4-propylsulfamoyl)phenoxy-2(R)-hydroxypropyl]-2-(4-methoxyphenyl)-1,1-dimethylethylamine;

N-[3-(2,3-dichloro-4-sulfamoyl)phenoxy-2(R)-hydroxypropyl]-2-(4-methoxyphenyl)-1,1-dimethylethylamine;

N-[3-(2,3-dichloro-4-methylsulfamoyl)phenoxy-2(R)-hydroxypropyl]-2-(4-methoxyphenyl)-1,1-dimethylethylamine;

N-[3-(3-chloro-2-cyano-4-pyrrolidinosulfamyl)phenoxy-2(R)-hydroxypropyl]-2-(4-fluorophenyl)-1,1-dimethylethylamine;

N-[3-(3-chloro-2-cyano-4-morpholinosulfamyl)phenoxy-2(R)-hydroxypropyl]-2-(benzyloxy)-1,1-dimethylethylamine;

N-[3-(2,3-dichloro-4-morpholinosulfamyl)phenoxy-2(R)-hydroxypropyl]-3-phenyl-1,1-dimethylpropylamine; and N-[3-(2,3-dichloro-4-morpholinosulfamyl)phenoxy-2(R)-hydroxypropyl]-4-phenyl-1,1-dimethylbutylamine;

(R)-1-[1,1-dimethyl-2-(4-methoxyphenyl)ethylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-(4-methoxyphenyl)ethylamino]-3-[10,11-dihydro-2-cyano-3-oxy-5H-dibenzo[a,d]cycloheptene-10-(S)-acetic acid]-propan-2-ol;

(R)-1-[1,1-dimethyl-2-(2-naphthyl)ethylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-(2-naphthyl)ethylamino]-3-[10,11-dihydro-2-cyano-3-oxy-5H-dibenzo[a,d]cycloheptene-10-(S)-acetic acid]-propan-2-ol;

(R)-1-[1,1-dimethyl-2-(methoxyphenyl)ethylamino]-3-[10-ethylthio-2-cyano-3-oxy-5H-dibenzo[a,d]cycloheptene]-propan-2-ol;

(R)-1-[1,1-dimethyl-2-(2-naphthyl)ethylamino]-3-[10-ethylthio-2-cyano-3-oxy-5H-dibenzo[a,d]cycloheptene]-propan-2-ol;

(R)-1-[1,1-dimethyl-2-(4-methoxyphenyl)ethylamino]-3-[10,11-dihydro-3-oxy-5H-dibenzo[a,d]cycloheptene-10-(R)-acetic acid]-propan-2-ol;

(R)-1-[1,1-dimethyl-2-(4-methoxyphenyl)ethylamino]-3-[10,11-dihydro-3-oxy-5H-dibenzo[a,d]cycloheptene-10-(S)-acetic acid]-propan-2-ol;

(R)-1-[1,1-dimethyl-2-(2-naphthyl)ethylamino]-3-[10,11-dihydro-3-oxy-5H-dibenzo[a,d]cycloheptene-10-(R)-acetic acid]-propan-2-ol;

(R)-1-[1,1-dimethyl-2-(2-naphthyl)ethylamino]-3-[10,11-dihydro-3-oxy-5H-dibenzo[a,d]cycloheptene-10-(S)-acetic acid]-propan-2-ol;

(R)-1-[1,1-dimethyl-2-(4-methoxyphenyl)ethylamino]-3-[10-ethylthio-3-oxy-5H-dibenzo[a,d]cycloheptene]-propan-2-ol;

(R)-1-[1,1-dimethyl-2-(2-naphthyl)ethylamino]-3-[10-ethylthio-3-oxy-5H-dibenzo[a,d]cycloheptene]-propan-2-ol;

(R)-1-[1,1-dimethyl-2-(4-methoxyphenyl)ethylamino]-3-[10-ethylthio-3-oxy-5H-dibenzo[a,d]cycloheptene]-propan-2-ol;

(R)-1-[1,1-dimethyl-2-(2-naphthyl)ethylamino]-3-[10-ethylthio-3-oxy-5H-dibenzo[a,d]cycloheptene]-propan-2-ol;

(R)-1-[1,1-dimethyl-2-(4-methoxyphenyl)ethylamino]-3-[3-oxy-10-oxo-5H-dibenzo[a,d]cycloheptene]-propan-2-ol;

(R)-1-[1,1-dimethyl-2-(2-naphthyl)ethylamino]-3-[3-oxy-10-oxo-5H-dibenzo[a,d]cycloheptene]-propan-2-ol;

(R)-1-[1,1-dimethyl-3-phenyl-propylamino]-3-[10,11-dihydro-2-cyano-3-oxy-5H-dibenzo[a,d]cycloheptene-10-(R)-acetic acid]-propan-2-ol;

(R)-1-[1,1-dimethyl-4-phenyl-butylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-phenoxy-ethylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-oxybenzyl-ethylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-(2-naphthalenyl)ethylamino]-3-[3-oxy-dibenz[b,f][1,4]oxazepin-11(10H)-one]-propan-2-ol monohydrochloride;

(R)-1-[1,1-dimethyl-2-(4-methoxyphenyl)-3-[3-oxy-dibenz[b,f][1,4]oxazepin-11(10H)-one]-propan-2-ol monohydrochloride;

(R)-1-[1,1-dimethyl-2-(1,1-dimethyl-4-phenyl)-butylamino]-3-[3-oxy-dibenz[b,f][1,4]oxazepin-11(10H)-one]-propan-2-ol monohydrochloride;

(R)-1-[1,1-dimethyl-2-(1,1-dimethyl-2-oxybenzyl)-ethylamino]-3-[3-oxy-dibenz[b,f][1,4]oxazepin-11(10H)-one]-propan-2-ol monohydrochloride;

(R)-1-[1,1-dimethyl-2-[(2-naphthalenyl)ethylamino]-3-[3-oxy-9,10-dihydrodibenz[b,f][1,4]oxazepin]-2-propanol monohydrochloride;

(R)-1-[1,1-dimethyl-2-(4-methoxyphenyl)ethylamino]-3-[3-oxy-9,10-dihydrodibenz[b,f][1,4]oxazepin]-2-propanol monohydrochloride;

(R)-1-[1,1-dimethyl-2-(1,1-dimethyl-4-phenyl)-butylamino]-3-[3-oxy-9,10-dihydrodibenz[b,f][1,4]oxazepin]-2-propanol monohydrochloride;

(R)-1-[1,1-dimethyl-2-(1,1-dimethyl-2-oxybenzyl)ethylamino]-3-[3-oxy-9,10dihydrodibenz[b,f][1,4]oxazepin]-2-propanol monohydrochloride;

(R)-1-[1,1-dimethyl-2-(2-naphthalenyl)ethylamino]-3-[3-oxy-9,10-dihydrodibenz[b,f][1,4]oxazepin-11(10H)-carboxymethyl]-propan-2-ol monohydrochloride;

(R)-1-[1,1-dimethyl-2-(4-methoxyphenyl)ethylamino]-3-[3-oxy-9,10-dihydrodibenz[b,f][1,4]oxazepin-11(10H)-carboxymethyl]-propan-2-ol monohydrochloride;

(R)-1-[1,1-dimethyl-2-(1,1-dimethyl-4-phenyl)-butylamino]-3-[3-oxy-9,10-dihydrodibenz[b,f][1,4]oxazepin-11(10H)-carboxymethyl]-propan-2-ol monohydrochloride;

(R)-1-[1,1-dimethyl-2-(1,1-dimethyl-2-oxybenzyl)ethylamino]-3-[3-oxy-9,10-dihydrodibenz[b,f][1,4]oxazepin-11(10H)-carboxymethyl]-propan-2-ol monohydrochloride; and pharmaceutically acceptable salts thereof. Trifluoroacetate and hydrochloride salts are preferred. Hydrochloride salts are more preferred.

More preferred compounds of the present invention include:

(R)-3-[2-cyano-4-[N-benzyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-[4-methylphenylsulfonyl]amino] phenoxy]-1-[1,1-dimethyl-2-(4-methoxyphenyl) ethylamino]-propan-2-ol;

(R)-3-[2-cyano-4-[N-methyl-N-[4-methylphenylsulfonyl] amino]phenoxy]-1-[1,1-dimethyl-2-(4-methoxyphenyl)ethylamino]-propan-2-ol;

(R)-3-[2-cyano-4-[N-methyl-N-[methylsulfonyl]amino] phenoxy]-1-[1,1-dimethyl-2-(4-methoxyphenyl) ethylamino]-propan-2-ol;

(R)-3-[2-cyano-4-[N-benzyl-N-[methylsulfonyl]amino] phenoxy]-1-[1,1-dimethyl-2-(4-methoxyphenyl) ethylamino]-propan-2-ol;

(R)-3-[2-cyano-4-[N-methylsulfonylamino]phenoxy]-1-[1,1-dimethyl-2-(4-methoxyphenyl)ethylamino]-propan-2-ol;

(R)-3-[2-cyano-4-[N-benzyl-N-[methylsulfonyl]amino] phenoxy]-1-[1,1-dimethyl-2-(2-naphthyl)ethylamino]-propan-2-ol;

(R)-3-[2-cyano-4-[N-[methylsulfonyl]amino]phenoxy]-1-[1,1-dimethyl-2-(2-naphthyl)ethylamino]-propan-2-ol; and (R)-3-[2-cyano-4-[N-benzyl-N-[4-methylphenylsulfonyl] amino]phenoxy]-1-[1,1-dimethyl-2-(2-naphthyl) ethylamino]-propan-2-ol;

(R)-3-[2-cyano-4-[N-benzyl-N'-morpholino]ureido] phenoxy]-1-[1,1-dimethyl-2-(2-naphthyl)ethylamino]-propan-2-ol;

(R)-3-[2-cyano-4-[N-benzyl-N'-morpholino]ureido] phenoxy]-[1,1-dimethyl-2-(4-methoxyphenyl) ethylamino]-propan-2-ol;

(R)-3-[2-cyano-4-[N-methyl-N'-morpholino]ureido] phenoxy]-1-[1,1-dimethyl-2-(2-naphthyl)ethylamino]-propan-2-ol;

(R)-3-[2-cyano-4-[N-methyl-N'-morpholino]ureido] phenoxy]-1-[1,1-dimethyl-2-(4-methoxyphenyl) ethylamino]-propan-2-ol;

(R)-1-[1,1-dimethyl-2-(4-methoxyphenyl)ethylamino]-3-[2-cyano-4-(N,N-dipropylaminocarbonyl)phenoxy]-propan-2-ol;

(R)-1-[1,1-dimethyl-2-(4-methoxyphenyl)ethylamino]-3-[2-cyano-4-(N-piperidinylcarbonyl)phenoxy]-propan-2-ol;

(R)-1-[1,1-dimethyl-2-(4-methoxyphenyl)ethylamino]-3-[2-cyano, 3-chloro-4-(N,N-dipropylaminocarbonyl) phenoxy]-propan-2-ol;

(R)-1-[1,1-dimethyl-2-(2-naphthyl)ethylamino]-3-[2-cyano, 3-chloro-4-(N,N-dipropylaminocarbonyl)phenoxy]-propan-2-ol;

(R)-1-[1,1-dimethyl-2-(4-methoxyphenyl)ethylamino]-3-[2-cyano-4-(N-pyrrolidinylcarbonyl)phenoxy]-propan-2-ol;

(R)-1-(1,1-dimethyl-2-(2-naphthyl)ethylamino)-3-[2-cyano-4-(N,N-dipropylaminocarbonyl)phenoxy]-propan-2-ol;

(R)-1-[1,1-dimethyl-2-(2-naphthyl)ethylamino]-3-[2-cyano-4-(N-piperidinylcarbonyl)phenoxy]-propan-2-ol; and (R)-1-[1,1-dimethyl-2-(2-naphthyl)ethylamino]-3-[2-cyano-4-(N-pyrrolidinylcarbonyl)phenoxy]-propan-2-ol.

N-[3-(3-chloro-2-cyano-4-dimethylsulfamoyl)phenoxy-2 (R)-hydroxypropyl]-2-(4-methoxyphenyl)-1,1-dimethylethylamine;

N-[3-(2,3-dichloro-4-morpholinosulfamyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2 (R)-hydroxypropyl]-2-(4-methoxyphenyl)-1,1-dimethylethylamine;

N-[3-(3-chloro-2-cyano-4-pyrrolidinosulfamyl)phenoxy-2 (R)-hydroxypropyl]-2-(4-methoxyphenyl)-1,1-dimethylethylamine;

N-[3-(3-chloro-2-cyano-4-pyrrolidinosulfamyl)phenoxy-2 (R)-hydroxypropyl]-2-(2-naphthyl)-1,1-dimethylethylamine;

N-[3-(3-chloro-2-cyano-4-morpholinosulfamyl)phenoxy-2 (R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]-2-(4-methoxyphenyl)-1,1-dimethylethylamine;

N-[3-[3-chloro-2-cyano-4-(benzyl-cyclopropyl)sulfamoyl] phenoxy-2(R)-hydroxypropyl]-2-(2-napthyl)-1,1-dimethylethylamine;

N-[3-[3-chloro-2-cyano-4-(benzyl-cyclopropyl)sulfamoyl] phenoxy-2(R)-hydroxypropyl]-2-(4-methoxyphenyl)-1,1-dimethylethylamine;

N-[3-(2,3-dichloro-4-dipropylsulfamoyl)phenoxy-2(R)-hydroxypropyl]-2-(2-naphthyl)-1,1-dimethylethylamine;

N-[3-(2,3-dichloro-4-pyrrolidinolsulfamyl)phenoxy-2(R)-hydroxypropyl]-2-(4-methoxyphenyl)-1,1-dimethylethylamine;

N-[3-(2,3-dichloro-4-piperidinolsulfamyl)phenoxy-2(R)-hydroxypropyl][2-(4-methoxyphenyl)-1,1-dimethyl] ethylamine;

N-[3-[3-chloro-2-cyano-4-(2'-cyanoeth-1-yl)-cyclopropylsulfamoyl]phenoxy-2(R)-hydroxypropyl]-2-(4-methoxyphenyl)-1,1-dimethylethylamine;

N-[3-[3-chloro-2-cyanos(2'-cyanoeth-1-yl)-cyclopropylsulfamoyl]phenoxy-2(R)-hydroxypropyl]-2-(2-napthyl)-1,1-dimethylethylamine;

N-[3-(3-chloro-2-cyano-4-morpholinosulfamyl)phenoxy-2 (R)-hydroxypropyl]-2-(benzyloxy)-1,1-dimethylethylamine;

N-[3-(2,3-dichloro-4-dipropylsulfamoyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2 (R)-hydroxypropyl]-2-(benzyloxy)-1,1-dimethylethylamine;

N-[3-(2,3-dichloro-4-morpholinosulfamyl)phenoxy-2(R)-hydroxypropyl]-3-phenyl-1,1-dimethylpropylamine; and N-[3-(2,3-dichloro-4-morpholinosulfamyl)phenoxy-2(R)-hydroxypropyl]-4-phenyl-1,1-dimethylbutylamine;

(R)-1-[1,1-dimethyl-2-(4-methoxyphenyl)ethylamino]-3-[10,11-dihydro-2-cyano-3-oxy-5H-dibenzo[a,d] cycloheptene-10-(R)-acetic acid]-propan-2-ol;

(R)-1-[1,1-dimethyl-2-(4-methoxyphenyl)ethylamino]-3-[10,11-dihydro-2-cyano-3-oxy-5H-dibenzo[a,d] cycloheptene-10-(S)-acetic acid]-propan-2-ol;

(R)-1-[1,1-dimethyl-2-(2-naphthyl)ethylamino]-3-[10,11-dihydro-2-cyano-3-oxy-5H-dibenzo[a,d]cycloheptene-10-(R)-acetic acid]-propan-2-ol;

(R)-1-[1,1-dimethyl-2-(2-naphthyl)ethylamino]-3-[10,11-dihydro-2-cyano-3-oxy-5H-dibenzo[a,d]cycloheptene-10-(S)-acetic acid]-propan-2-ol;

(R)-1-[1,1-dimethyl-2-(4-methoxyphenyl)ethylamino]-310-ethylthio-2-cyano-3-oxy-5H-dibenzo[a,d]cycloheptene]-propan-2-ol;

(R)-1-[1,1-dimethyl-2-(4-methoxyphenyl)ethylamino]-310-ethylthio-2-cyano-3-oxy-5H-dibenzo[a,d]cycloheptene]-propan-2-ol;

(R)-1-[1,1-dimethyl-2-(4-methoxyphenyl)ethylamino]-3-[10,11-dihydro-3-oxy-5H-dibenzo[a,d]cycloheptene-10-(R)-acetic acid]-propan-2-ol;

(R)-1-[1,1-dimethyl-2-(4-methoxyphenyl)ethylamino]-3-[10,11-dihydro-3-oxy-5H-dibenzo[a,d]cycloheptene-10(S)-acetic acid]-propan-2-ol;

(R)-1-[1,1-dimethyl-2-(2-naphthyl)ethylamino]-3-[10,11-dihydro-3-oxy-5H-dibenzo[a,d]cycloheptene-10-(R)-acetic acid]-propan-2-ol;

(R)-1-[1,1-dimethyl-2-(2-naphthyl)ethylamino]-3-[10,11-dihydro-3-oxy-5H-dibenzo[a,d]cycloheptene-10-(S)-acetic acid]-propan-2-ol;

(R)-1-[1,1-dimethyl-2-(4-methoxyphenyl)ethylamino]-3-[10-ethylthio-3-oxy-5H-dibenzo[a,d]cycloheptene]-propan-2-ol;

(R)-1-[1,1-dimethyl-2-(2-naphthyl)ethylamino]-3-[10-ethylthio-3-oxy-5H-dibenzo[a,d]cyclobeptene]-propan-2-ol;

(R)-1-[1,1-dimethyl-3-phenyl-propylamino]-3-[10,11-dihydro-2-cyano-3-oxy-5H-dibenzo[a,d]cycloheptene-10-(R)-acetic acid]-propan-2-ol;

(R)-1-[1,1-dimethyl-4-phenyl-butylamino]-3-[10,11-dihydro2-cyano-3-oxy-5H-dibenzo[a,d]cycloheptene-10-(R)-acetic acid]-propan-2-ol;

(R)-1-[1,1-dimethyl-2-phenoxy-ethylamino]-3-[10,11-dihydro-2-cyano-3-oxy-5H-dibenzo[a,d]cycloheptene-10-(R)-acetic acid]-propan-2-ol; and (R)-1l-[1,1-dirmethyl-2-oxybenzyl-ethylamino]-3-[10,11-dihydro-2-cyano-3-oxy-5H-5D dibenzo[a,d]cycloheptene-10-(R)-acetic acid]-propan-2-ol;

(R)-1-[1,1-dimethyl-2-(2-naphthalenyl)ethylamino]-3-[3-oxy-dibenz[b,f][1,4]oxazepin-11(10H)-one]-propan-2-ol monohydrochloride;

(R)-1-[1,1-dimethyl-2-(4-methoxyphenyl]-3-[3-oxy-dibenz[b,f][1,4]oxazepin-11(10H)-one-]-propan-2-ol monohydrochloride;

(R)-1-[1,1-dimethyl-2-(1,1-dimethyl-4-phenyl)-butylamino]-3-[3-oxy-dibenz[b,f][1,4]oxazepin-11(10H)-one]-propan-2-ol monohydrochloride;

(R)-1-[1,1-dimethyl-2-(1,1-dimethyl-2-oxybenzyl)-ethylamino]-3-[3-oxy-dibenz[b,f]1,4]oxazepin-11(10H)-one]-propan-2-ol monohydrochloride;

(R)-[1,1-dimethyl-2-[(2-naphthalenyl)ethylamino]-3-[3-oxy-9,10-dihydrodibenz[b,f][1,4]oxazepin]-2-propanol monohydrochloride;

(R)-1-[1,1-dimethyl-2-(4-methoxyphenyl)ethylamino]-3-(3-oxy-9,10-dihydrodibenz[b,f][1,4]oxazepin]-2-propanol monohydrochloride;

(R)-1-[1,1-dimethyl-2-(1,1-dimethyl-4-phenyl)-butylamino]-3-[3-oxy-9,10-dihydrodibe[b,f][1,4]oxazepin]-2-propanol monohydrochloride;

(R)-1-[1,1-dimethyl-2-(1,1-dimethyl-2-oxybenzyl)ethylamino]-3-[3-oxy-9,10-dihydrodibenz[b,f][1,4]oxazepin]-2-propanol monohydrochloride;

(R)-1-[1,1-dimethyl-2-(2-naphthalenyl)ethylamino]-3-[3-oxy-9,10-dihydrodibenz[b,f][1,4]oxazepin-11(10H)-carboxymethyl]-propan-2-ol monohydrochloride;

(R)-1-[1,1-dimethyl-2-(4-methoxyphenyl)ethylamino]-3-[3-oxy-9,10-dihydrodibenz[b,f][1,4]oxazepin-11(10H)-carboxymethyl]-propan-2-ol monohydrochloride;

(R)-1-[1,1-dimethyl-2-(1,1-dimethyl-4-phenyl)-butylamino]-3-[3-oxy-9,10-dihydrodibenz[b,f][1,4]oxazepin-11(10H)-carboxymethyl-propan-2-ol monohydrochloride;

(R)-1-[1,1-dimethyl-2-(1,1-dimethyl-2-oxybenzyl)ethylamino]-3-[3-oxy-9,10-dihydrodibenz[b,f][1,4]oxazepin-11(10H)-carboxymethyl]-propan-2-ol monohydrochloride; and pharmaceutically acceptable salts thereof.

The most preferred compounds of the present invention include:

(R)-3-[2-cyano-4-[N-benzyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[methylsulfonyl]amino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(4-methoxyphenyl)ethylamino]-propan-2-olt;

(R)-3-[2-cyano-4-[N-benzyl-N-[methylsulfonyl]amino]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(4-methoxyphenyl)ethylamino]-propan-2-ol;

(R)-3-[2-cyano-4-[N-methyl-N'-morpholino]ureido]phenoxy]-1-[1,1-dimethyl-2-(2-naphthyl)ethylamino]-propan-2-ol;

(R)-3-[2-cyano-4-[N-methyl-N'-morpholino]ureido]phenoxy]-1-[1,1-dimethyl-2-(4-methoxyphenyl)ethylamino]-propan-2-ol and (R)-3-[2-cyano-4-[N-benzyl-N-[4-methylphenylsulfonyl]amino]phenoxy]-1-[1,1-dimethyl-2-(2-naphthyl)ethylamino]-propan-2-ol;

(R)-1-[1,1-dimethyl-2-(4-methoxyphenyl)ethylamino]-3-[2-cyano-4-(N,N-dipropylaminocarbonyl)phenoxy]-propan-2-ol;

(R)-1-[1,1-dimethyl-2-(4-methoxyphenyl)ethylamino]-3-[2-cyano-4-(N-piperidinylcarbonyl)phenoxy]-propan-2-ol;

(R)-1-[1,1-dimethyl-2-(4-methoxyphenyl)ethylamino]-3-[2-cyano-4-(N-pyrrolidinylcarbonyl)phenoxy]-propan-2-ol;

(R)-1-[1,1-dimethyl-2-(2-naphthyl)ethylamino]-3-[2-cyano-4-(N,N-dipropylaminocarbonyl)phenoxy]-propan-2-ol;

(R)-1-[1,1-dimethyl-2-(2-naphthyl)ethylamino]-3-[2-cyano-4-(N-piperidinylcarbonyl)phenoxy]-propan-2-ol; and (R)-1-[1,1-dimethyl-2-(2-naphthyl)ethylamino]-3-[2-cyano-4-(N-pyrrolidinylcarbonyl)phenoxy]-propan-2-ol.

N-[3-(2,3-dichloro-4-morpholinosulfamyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2(R)-hydroxypropyl]-2-(4-methoxyphenyl)-1,1-dimethylethylamine;

N-[3-(3-chloro-2-cyano-4-pyrrolidinsulfamoyl)phenoxy-2(R)-hydroxypropyl]-2-(4-methoxyphenyl)-1,1-dimethylethylamine;

N-[3-(3-chloro-2-cyano-4-pyrrolidinosulfamyl)phenoxy-2(R)-hydroxypropyl]-2-(2-naphthyl)-1,1-dimethylethylamine;

N-[3-(3-chloro-2-cyano-4-morpholinosulfamyl)phenoxy-2(R)-hydroxypropyl]-2-(2-naphthyl)-1,1-dimethylethylamine;

N-[3-(3-chloro-2-cyano-4-thiomorpholinosulfamyl)phenoxy-2(R)-hydroxypropyl]-2-(2-naphthyl)-1,1-dimethylethylamine;

N-[3-(3-chloro-2-cyano-4-thiomorpholinosulfamyl)
phenoxy-2(R)-hydroxypropyl]-2-(4-methoxyphenyl)-1,
1-dimethylethylamine;
N-[3-(2,3-dichloro-4-pyrrolidinolsulfamyl)phenoxy-2(R)-
hydroxypropyl]-2-(4-methoxyphenyl)-1,1-
dimethylethylamine;
N-[3-(2,3-dichloro-4-piperidinolsulfamoyl)phenoxy-2(R)-
hydroxypropyl]-2-(4-methoxyphenyl)-1,1-
dimethylethylamine;
N-[3-(3-chloro-2-cyano-4-morpholinosulfamyl)phenoxy-2
(R)-hydroxypropyl]-2-(benzyloxy)-1,1-
dimethylethylamine;
N-[3-[3-chloro-2-cyano-4-(2'-cyanoeth-1-yl)-
cyclopropylsulfamoyl]phenoxy-2(R)-hydroxypropyl]-2-
(4-methoxyphenyl)-1,1-dimethylethylamine;
N-[3-[3-chloro-2-cyano-4-(2'-cyanoeth-1-yl)-
cyclopropylsulfamoyl]phenoxy-2(R)-hydroxypropyl]-2-
(2-napthyl)-1,1-dimethylethylamine;
N-[3-(3-chloro-2-cyano-4-morpholinosulfamyl)phenoxy-2
(R)-hydroxypropyl]-2-(benzyloxy)-1,1-
dimethylethylamine;
N-[3-(2,3-dichloro-4-morpholinosulfamyl)phenoxy-2(R)-
hydroxypropyl]-4-phenyl-1,1-dimethylbutylamine;
N-[3-(2,3-dichloro-4-morpholinosulfamyl)phenoxy-2(R)-
hydroxypropyl]-3-phenyl-1,1-dimethylpropylamine;
N-[3-(2,3-dichloro-4-morpholinosulfamyl)phenoxy-2(R)-
hydroxypropyl]-4-phenyl-1,1-dimethylbutylamine;
(R)-1-[1,1-dimethyl-2-(4-methoxyphenyl)ethylamino]-3-
[10,11-dibydro-2-cyano-3-oxy-5H-dibenzo[a,d]
cycloheptene-10-(R)-acetic acid]-propan-2-ol;
(R)-1-[1,1-dimethyl-2-(4-methoxyphenyl)ethylamino]-3-
[10,11-dihydro-2-cyano-3-oxy-5H-dibenzo[a,d]
cycloheptene-10-(S)-acetic acid]-propan-2-ol;
(R)-1-[1,1-dimethyl-2-(2-naphthyl)ethylamino]-3-[10,11-
dihydro-2-cyano-3-oxy-5H-dibenzo[a,d]cycloheptene-
10-(R)-acetic acid]-propan-2-ol;
(R)-1-[1,1-dimethyl-2-(2-naphthyl)ethylamino]-3-[10,1
1-dihydro-2-cyano-3-oxy-5H-dibenzo[a,d]cycloheptene-
10-(S)-acetic acid]-propan-2-ol;
(R)-1-[1,1-dimethyl-2-(2-naphthyl)ethylamino]-3-[10-
ethylthio-2-cyano-3-oxy-5H-dibenzo[a,d]cycloheptenel-
propan-2-ol; and
(R)-1-[1,1-dimethyl-2-(2-naphthyl)ethylamino]-3-[10-
ethylthio-2-cyano-3-oxy-5H-dibenzo[a,d]cycloheptene]-
propan-2-ol;
(R)-1-[1,1-dimethyl-2-(2-naphthalenyl)ethylamino]-3-[3-
oxy-dibenz[b,f][1,4]oxazepin-11(10H)-one]-propan-2-ol
monohydrochloride;
(R)-1-[1,1-dimethyl-2-(4-methoxyphenyl]-3-[3-oxy-dibenz
[b,f][1,4]oxazepin-11(10H)-one-]-propan-2-ol monohy-
drochloride;
(R)-1-[1,1-dimethyl-2-[(2-naphthalenyl)ethylamino]-3-[3-
oxy-9,10-dihydrodibenz[b,f][1,4]oxazepin]-2-propanol
monohydrochloride;
(R)-[1,1-dimethyl-2-(4-methoxyphenyl)ethylamino]-3-[3-
oxy-9,10-dihydrodibenz[b,f][1,4]oxazepin]-2-propanol
monohydrochloride;
(R)-1-[1,1-dimethyl-2-(2-naphthalenyl)ethylamino]-3-[3-
oxy-9,10-dihydrodibenz[b,f][1,4]oxazepin-11(10H)-
carboxymethyl]-propan-2-ol monohydrochloride;
(R)-1-[1,1-dimethyl-2-(4-methoxyphenyl)ethylamino]-3-
[3-oxy-9,10-dihydrodibenz[b,f][1,4]oxazepin-11(10H)-
carboxymethyl]-propan-2-ol monohydrochloride;
and pharmaceutically acceptable salts thereof.

The present compounds can be formulated as pharmaceutically acceptable salts and complexes thereof. Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid. methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. Using, the protocols described herein as a model, one of ordinary skill in the art can readily produce other compounds of the present invention.

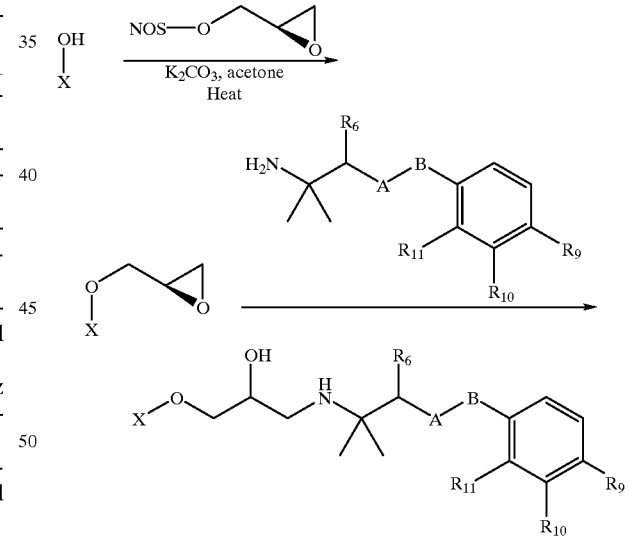

Scheme 1

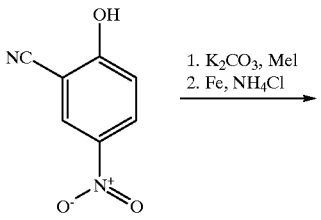

Scheme 2

-continued
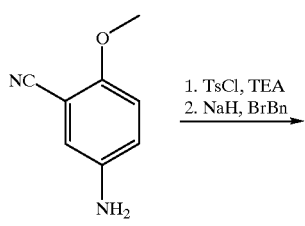
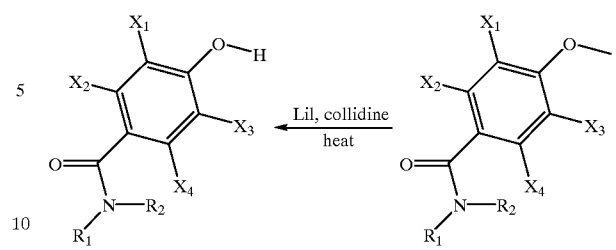
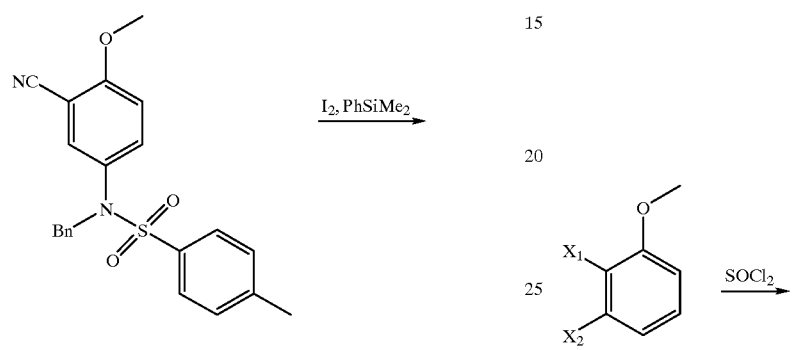
Scheme 4
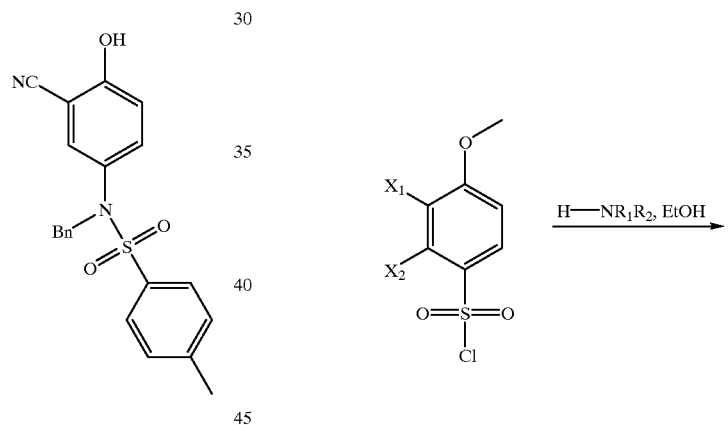
Scheme 3
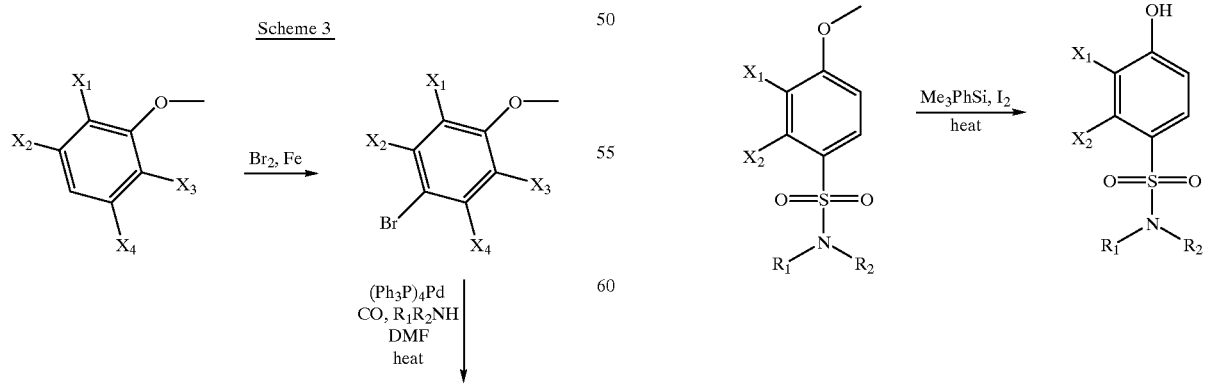

Scheme 5
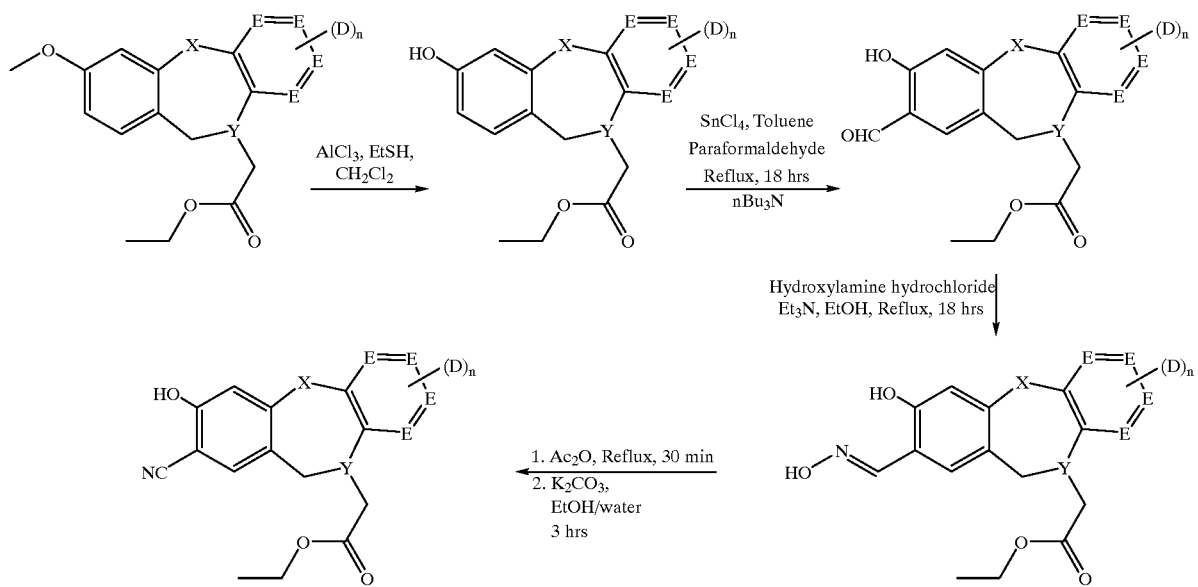
Scheme 6
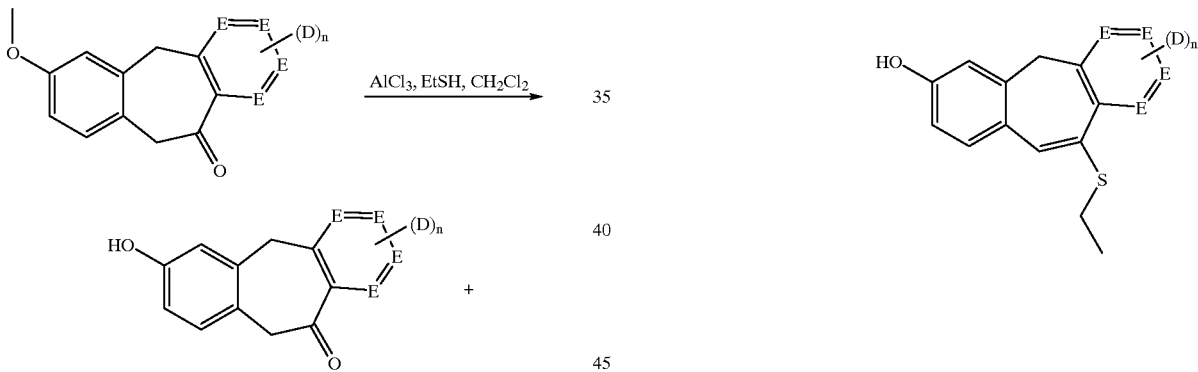
Scheme 7
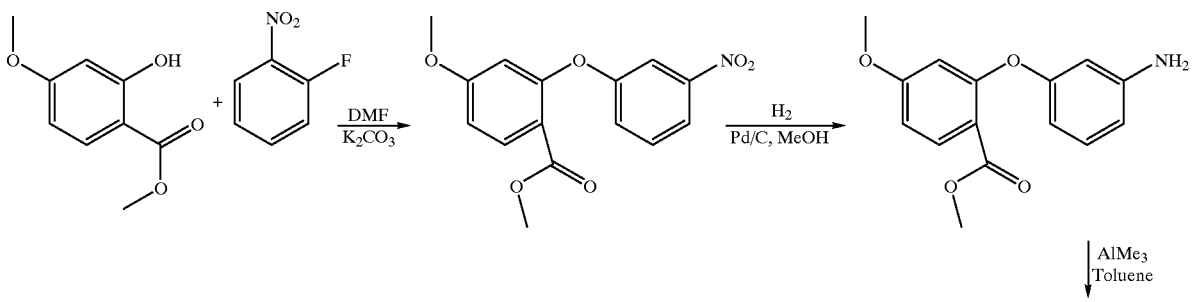

Scheme 8

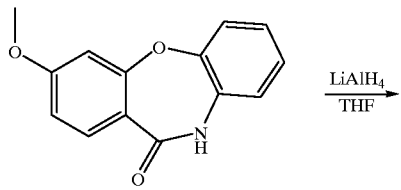

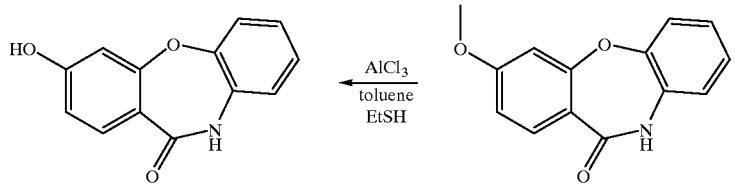

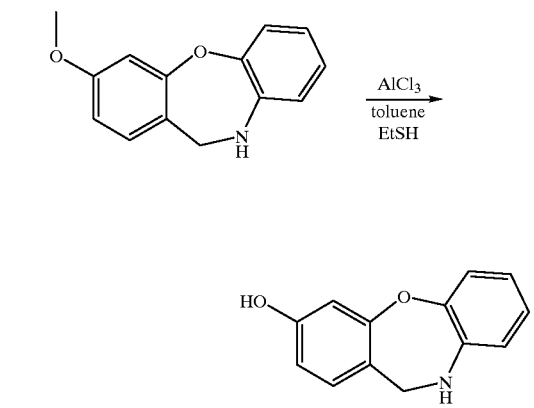

Scheme 9

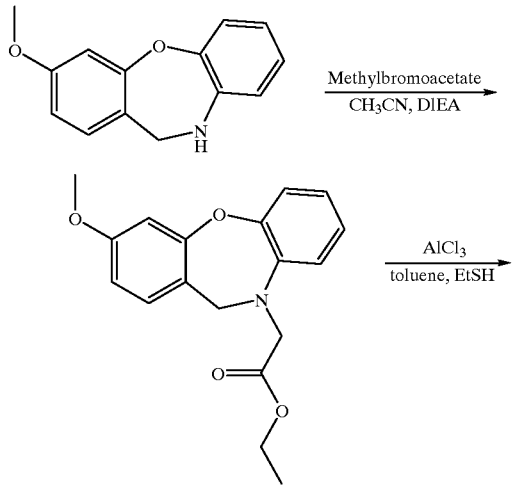

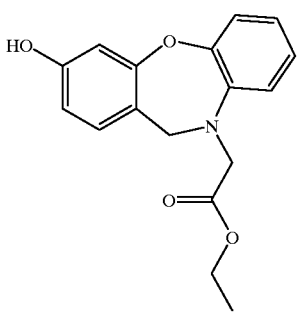

A general procedure used to synthesize many of the compounds can be carried out as described in Scheme 1, above: A solution of aryl alcohol (X—OH) in acetone was treated with an appropriate base such as $K_2CO_3$, heated for 15 min. R-glycidyl nosylate was added and the reaction continued overnight to give the corresponding glycidyl ether (Scheme 1). In the case of an alkyl alcohol, a stronger base, e.g. NaH in DMF was used. This method can also be used for aryl alcohols. A solution of the substituted glycidyl ether and excess amine (typically 1,1-dimethyl-2-(4-methyloxyphenyl)ethylamine) in absolute ethanol, acetonitrile, THF or any other similar solvent in the presence of a suitable catalyst such as $LiClO_4$ is stirred overnight at reflux. The product is purified by normal phase chromatography. Hydrochloride salts are prepared by treatment of the corresponding free base with HCl either in gas phase or 4M dioxane solution, or any other standard method.

The synthesis of the corresponding o-substituted aryl ethers is described in Scheme 2–9. For example, treatment of a 2-cyano-4-nitrophenol (Scheme 2) with $K_2CO_3$ followed by methyl iodide, yields the corresponding aryl methyl ether, treatment with Fe powder or any other reducing agent capable of reducing the aryl nitro group in the presence on the nitrile, gives the corresponding aniline. Reaction of the thus obtained aniline with an appropriate sulfonyl or carbonyl chloride such as tosyl, or mesyl chloride or 4-morpholinecarbonyl chloride, in the presence or triethyl amine produces the corresponding sulfonamide or urea. Alkylation of the sulfonamide nitrogen can be carried out via deprotonation with an appropriate base such as NaH in an appropriate anhydrous solvent such as DMF, followed by treatment with the desired alkyl halide such as benzyl bromide. The methyl ether was then removed with $Me_3PhSi$ and $I_2$ or with LiI in collidine, or any other standard deprotection method known to a chemist skilled in the art. The 2,3-disubstituted methyl ether (Scheme 3) is treated with bromine in the presence of Fe resulting in regiospecific bromination. The resulting bromide can then be treated under carbonylamidation conditions, $(Ph_3)_4Pd$, CO, $R_1R_2NH$, DMF, heat to give the resulting amide which is deprotected with LiI in collidine to give the corresponding aryl alcohol. Treatment of an ortho-substituted aryl ether Scheme 4 with $SOCl_2$ followed by a primary. or secondary amine gives the p-sulfonamide. The methyl ether is then removed with $Me_3PhSi$ and $I_2$ or with LiI in an appropriate solvent such as collidine, or any other deprotection method known to a chemist skilled in the art (Scheme 2), to yield the desired arylalcohol. The methyl aryl ether (Scheme 5) is converted to the corresponding aryl alcohol with $AlCl_3$/EtSH. The cyano group is introduced selectively adjacent to the aryl alcohol by treating the aryl alcohol with paraformaldehyde and $SnCl_4$ to give the formyl derivative. Conversion of the formyl group to the corresponding oxime and dehydration with $Ac_2O$ gives the cyano-aryl ester. Final hydrolysis of the aryl ester gives the desired aryl alcohol. Deprotection of the methyl aryl ether of the ketone(Scheme 6). gives the aryl alcohol as well as the thio enolether. Nucleophilic displacement of the aryl fluoride (Scheme 7) with the potassium salt of the phenol gives a biaryl ether which is reduced and then cyclized to give a cyclic amide which is converted to the corresponding aryl alcohol via deprotection with $AlCl_3$/EtSH. The amide from Scheme 7 is reduced to the tricyclic anilide (Scheme 8) which is converted to the corresponding aryl alcohol via deprotection with $AlCl_3$/EtSH. The tricyclic anilide from Scheme 8 is alkylated with the appropriate electrophile to give the corresponding N-alkylated material (Scheme 9).

With appropriate manipulation and protection of any chemical functionality, synthesis of the remaining compounds of Formula (I) is accomplished by methods analogous to Schemes 1–9.

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered or the number of doses will have to be increased.

Preferably the composition is in unit dosage form. For oral application, for example, a tablet, or capsule may be administered, for nasal application, a metered aerosol dose may be administered, for transdermnal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "modulator" means antagonist.

As used herein, "treatment" of a disease includes, but is not limited to prevention, retardation and prophylaxis of the disease.

The compounds of the present invention preferably exhibit a ratio of β-receptor binding to calcium receptor binding (in $K_i$ values) of 3 or greater, more preferably of 10 or greater, most preferably of 30 or greater.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), diseases involving abnormally low serum parathyroid levels, cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma, and pancreatitis.

In a preferred embodiment of the present invention, the present compounds are used to increase serum parathyroid ("PTH") levels in a pulsatile manner. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia malignancy and osteoporosis. Increasing serum PTH levels can be used to treat various diseases including bone and mineral related diseases.

Various embodiments of the present invention include administering the compound to a patient to cause an increase in serum PTH having a duration up to one hour, one hour to twenty-four hours, one hour to twelve hours, one hour to six hours, one hour to five hours, one hour to four hours, two to five hours, two hours to four hours, or three hours to about six hours.

Various additional embodiments include administering the compound to a patient to cause an increase in serum PTH up to 0.5 fold, 0.5 to 5 fold, 5 fold to 10 fold, and at least 10 fold, greater than the peak serum PTH in the patient. The peak serum level is measured with respect to the patient not undergoing treatment.

Compositions of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil. olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests:

(I) Calcium Receptor Inhibitor Assay

Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., *J. Bone Miner. Res.* 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

The procedure was as follows:

Cells were maintained in T-150 flasks in selection media (DMEM supplemented with 10% fetal bovine serum and 200 ug/mL hygromycin B), under 5% $CO_2$:95% air at 37° C. and were grown up to 90% confluency. The medium was decanted and the cell monolayer was washed twice with phosphate-buffered saline (PBS) kept at 37° C. After the second wash, 6 mL of 0.02% EDTA in PBS was added and incubated for 4 minutes at 37° C. Following the incubation, cells were dispersed by gentle agitation. Cells from 2 or 3 flasks were pooled and pelleted (100×g). The cellular pellet was resuspended in 10–15 mL of SPF-PCB+ and pelleted again by centrifugation. This washing was done twice. Sulfate- and phosphate-free parathyroid cell buffer (SPF-PCB) contains 20 MM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence. The pellet was resuspended in 10 mL of SPF-PCB+ containing 2.2 uM fluo-3 (Molecular Probes) and incubated at room temperature for 35 minutes. Following the incubation period, the cells were pelleted by centrifugation. The resulting pellet was washed with SPF-PCB+. After this washing, cells were resuspended in SPF-PCB+ at a density of $1-2\times10^6$ cells/mL. For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain $F_{max}$, and the apparent $F_{min}$ was determined by adding Tris-EGTA (2.5 M Tris-Base, 0.3 M EGTA). The concentration of intracellular calcium was calculated using the following equation: Intracellular calcium=$(F-F_{min}/F_{max})\times Kd$; where Kd=400 nM.

To determine the potential calcilytic activity of test compounds, cells were incubated with test compound (or vehicle as a control) for 90 seconds before increasing the concentration of extracellular $Ca^{2+}$ from 1 to 2mM. Calcilytic compounds were detected by their ability to block, in a concentration-dependent manner, increases in the concentration of intracellular $Ca^{2+}$ elicited by extracellular $Ca^{2+}$.

In general, those compounds having lower $IC_{50}$ values in the Calcium Receptor Inhibitor Assay are more preferred compounds. Compounds having an $IC_{50}$ greater than 50 uM were considered to be inactive. Preferred compounds are those having an $IC_{50}$ of 10 uM or lower, more preferred compounds have an $IC_{50}$ of 1 uM, and most preferred compounds have an $IC_{50}$ of 0.1 uM or lower.

(II) Calcium Receptor Binding Assay

HEK 293 4.0–7 cells stably transfected with the Human Parathyroid Calcium Receptor("HuPCaR") were scaled up in T180 tissue culture flasks. Plasma membrane is obtained by polytron homogenization or glass douncing, in buffer (50 mM Tris-HCl pH 7.4, 1 mM EDTA, 3 mM $MgCl_2$) in the presence of a protease inhibitor cocktail containing 1 uM Leupeptin, 0.04 uM Pepstatin, and 1 mM PMSF. Aliquoted membrane was snap frozjen and stored at $-80°$ C. $^3$H labeled compound was radiolabeled to a radiospecific activity of 8 l Ci/mmole and was aliquoted and stored in liquid nitroen for radiochemical stability.

A typical reaction mixture contains 2 nM $^3$H compound ((R,R)-N-4'-methoxy-t-3-3'-methyl-1'-ethylphenyl-1-(1-naphthyl)ethylamine), 4–10 ug membrane in homogenization buffer containing 0.1% gelatin and 10% EtOH in a reaction volume of 0.5 mL. Incubation is performed in 12×75 polyethylene tubes in an ice water bath. To each tube 25 uL of test sample in 100% EtOH is added, followed by 400 uL of cold incubation buffer, and 25 uL of 20 nM $^3$H-compound in 100% EtOH. The binding reaction is initiated by the addition of 50 uL of 80–200 ug/mL HEK 293 4.0–7 membrane diluted in incubation buffer, and allowed to incubate at 4° C. for 30 min. Wash buffer is 50 mM Tris-HCl containing 0.1I% PEI. Nonspecific binding is determined by the addition of 100-fold excess of unlabeled homologous ligand, and is generally 30% of total binding. The binding reaction is terminated by rapid filtration onto 1% PEI pretreated GF/C filters using a Brandel Harvestor. Filters are placed in scintillation fluid and radioactivity assessed by liquid scintillation counting.

III β-adrenergic Receptor Binding Assay

The β-Adrenergic Receptor Binding Assay is carried out as follows. Incubations are performed in polypropylene reaction tubes in a 37° C. water bath. To each tube 50 uL of test sample is added, followed by 300 uL of assay buffer (50 mM Tris-HCl, pH 7.5), and 50 uL of 20 nM [$^3$H]-dihydroalprenolol. The binding reaction is initiated by the addition of 100 uL of 3.75 mg/mL well-washed rat cortex membranes in assay buffer, and allowed to incubate at 37° C. for 30 minutes. Non-specific binding is determined in the presence of 10 $\mu$M alprenolol. The final concentration of reactants is: 2 nM [$^3$H]-dihydroalprenolol, and 75 mg/mL rat cortex membrane in a reaction volume of 0.5 mL.

The binding reaction is terminated by rapid filtration with ice-cold assay buffer onto GF/C filters (Brandel, Gaithersburg, Md.) which have been soaked for 15 minutes in assay buffer. The reaction is first diluted with 3 mL of cold assay buffer (4° C.), then aspirated onto the filter followed by 3×3 mL washes. Filter disks are placed in 7-mL polypropylene scintillation vials with 5 mL of ScintiSafe 50% (Fisher Scientific, Pittsburgh, Pa.), and counted overnight.

β-adrenergic activity can be reduced using appropriate functional groups and structural modifications. β-adrenergic receptor activity and binding to the β-adrenergic receptor can be measured using standard techniques. For example, see Riva et al., *Mol. Pharmacol*, 36:201–210, 1989.

In one embodiment of the present invention the calcilytic compounds have a $K_i \geq 0.1$ uM, at the β-adrenergic receptor as measured using the β-Adrenergic Receptor Binding Assay described above. In other embodiments, using the β-Adrenergic Receptor Assay calcilytic compounds have a $K_i \geq 1.0$ uM, and $K_i \geq 10.0$ uM.

The following examples are illustrative, but not limiting of the embodiments of the present invention.

EXAMPLES

Example 1

Preparation of (R)-3-[2-cyano-4-[N-benzyl-N-[4-methylphenylsulfonyl]aminophenoxy]-1-[1,1-dimethyl-2-(4-methoxyphenyl)ethylamino]-propan-2-ol hydrochloride salt a) 5-Nitro-2-methoxybenzonitrile A mixture of 2-cyano-4-nitrophenol (3.5 g, 21 mmol), $K_2CO_3$ (5.9 g, 42 mmol), and MeI (9.08 g, 64 mmol) in acetone (50 mL) was heated at reflux overnight. The mixture was cooled and concentrated, taken up in $H_2O$, stirred, filtered the yellow solid, dried by air (3.0 g, 79%). $^1$H NMR (400 MHz, $CDCl_3$): d 4.08 (s, 3H), 7.12 (d, J=9.2 Hz, 1H), 8.5 (m, 2H).

b) 5-Amino-2-methoxylbenzonitrile

The compound of Example 1(a) (8.5 g, 47.7 mmol) from above, Fe powder (13.3 g, 238.6 mmol), and $NH_4Cl$ (1.3 g, 23.9 mmol) in $EtOH/H_2O$ (100 mL, 9:1) was heated at reflux in 2 h. The mixture was filtered hot. The filtrate was concentrated, taken up in $H_2O$, stirred, filtered and the tan solid thus obtained air dried to obtain 5.0 g (71%) of the of the above named compound. $^1$H NMR (400 MHz, $CDCl_3$): d 4.08 (s, 3H), 5.50 (s, 2H), 7.12 (d, J=9.2 Hz, 1H), 8.50 (m, 2H).

c) 2-Methoxy-5-[[N-4-methylphenyl]sulfonyl]aminobenzonitrile

To a stirred mixture of the compound of Example 1(b) (2.0 g, 13.6 mmol), and $Et_3N$ (1.44 g, 14.7 moles) in $CH_2Cl_2$ (20 mL) was added p-toluenesulfonyl chloride. (2.72 g, 14.7 mmol). After stirring at RT overnight, the mixture was concentrated, taken up in $H_2O$, extracted with EtOAc, washed with brine, dried over $MgSO_4$, filtered, concentrated, triturated with $Et_2O$ to give 2.50 g (60%) of the above named compound as an off-white solid. $^1$H NMR (400 MHz, $CDCl_3$): d 2.48 (s, 3H), 3.95 (s, 3H), 6.80 (d, J=9.1 Hz, 2H), 7.03 (d, J=9.2 Hz, 1H), 7.40 (m, 2H), 7.52 (d, J=9.1 Hz, 2H), 9.55 (s, 1H).

d) 2-Methoxy-5-[[N-4-methylphenyl]sulfonyl-N-benzyl]aminobenzonitrile

To a stirred suspension of NaH (pre-washed with hexane, 60% oil, 0.15 g, 3.6 mmol) in DMF (20 mL) was added the compound of Example 1(c) (1.0 g, 3.3 mmol) in portions. After stirring at RT for 1 h, benzyl bromide (0.6 g, 3.4 mmol) was added, and continued to stir at RT overnight. The mixture was quenched with $H_2O$, extracted with EtOAc. The organic extracts were washed with brine, dried over $MgSO_4$, concentrated to give 0.7 g (58%) of the above named compound as a brown solid. $^1$H NMR (400 MHz, $CDCl_3$): d 2.49 (s, 3H), 3.87 (s, 3H), 4.68 (s, 2H), 6.80 (d, J=9.1 Hz, 2H), 7.01 (d, 2.7 Hz, 1H), 7.25 (m, 7H), 7.50 (d, J=9.1 Hz, 2H).

e) 2-Hydroxyl-5-[[N-4-methylphenyl]sulfonyl-N-benzyl]aminobenzonitrile

A mixture of the compound of Example 1(d) (0.70 g, 1.7 mmol), $PhSiMe_3$ (0.41 g, 2.6 mmol), and iodine (0.67 g, 2.6751 mmol) was heated at 130° C. in 3 h. The mixture was cooled and added saturated aqueous $NaHSO_3$, extracted with EtOAc. The organic extracts were washed with $H_2O$, brine, dried over $MgSO_4$, filtered, concentrated, and purified by flash column chromatography (40% EtOAc/Hexane) to afford the title compound as a light brown solid (0.20 g, 30%). $^1$H NMR (400 MHz, $CDCl_3$): d 2.49 (s, 3H), 4.68 (s, 2H), 6.80 (d, J=9.1 Hz, 2H), 7.01 (d, 2.7 Hz, 1H), 7.25 (m, 7H), 7.50 (d, J=9.1 Hz, 2H).

f) 2-Cyano-4-[N-benzyl-N-[4-methylphenylsulfonyl]amino]phenyl glycidol

A mixture of the compound of Example 1(e) (0.20 g, 0.5 mmol), $K_2CO_3$, and 2R-(-)-glycidyl-3- nitrobenzenesulfonate (0.16 g, 0.6 mmol) in acetone (5 mL) was refluxed in 24 h. The mixture was cooled, concentrated, taken up in H$_2$O, extracted with EtOAc(3×). The organic extracts were washed with saturated NaHCO$_3$, brine, dried over MgSO$_4$, filtered, concentrated, and purified by flash column chromatography (35% EtOAc/Hexane) to afford the title compound (0.148 g, 65%) as an off white foam. $^1$H NMR (400 MHz, CDCl$_3$): d 2.29 (s, 3H), 2.85 (t, J=4.5 Hz, 1H), 2.95 (t, J=4.5 Hz, 1H), 3.40 (m, 1H), 4.10 (dd, J=5.4, 11.4 Hz, 1H), 4.43 (dd, J=2.6, 11.4 Hz, 1H), 4.68 (s, 2H), 6.80 (d, J=9.1 Hz, 2H), 7.01 (d, 2.7 Hz, 1H), 7.25 (m, 7H), 7.50 (d, J=9.1 Hz, 2H).

g) N-[2R-Hydroxy-3-[[2-cyano-4-[N-benzyl-N-[4-methylphenyl sulfonyl]amino]phenoxy]propyl-1,1-dimethyl-2-[4-methoxyphenyl]ethylamine hydrochloride A mixture of the compound of Example 1(f) (0.145 g, 0.3 mmol), LiClO$_4$ (0.10 g, 0.6 mmol), and 4-methoxyphenyl-1,1-dimethyl (0.07 g, 0.4 mmol) in dried acetonitrile (5 mL) was heated at reflux in 24 h. The mixture was cooled and concentrated, taken up in H$_2$O, extracted with EtOAc (3×). The combined organic extracts were washed with brine, dried over MgSO$_4$, filtered, concentrated, and purified by flash column chromatography (3% MeOH/CH$_2$Cl$_2$) to afford a colorless oil which was stirred in methanol and added 4M HCl, concentrated, and triturated in ether to give the title compound (0.120 g, 60%) as an off white solid. $^1$H NMR (400 MHz, DMSO-d$_6$): d 1.09 (s, 3H), 1.11 (s, 3H), 2.42 (s, 3H), 2.64 (s, 2H), 3.10 (dd, J=7.2, 14.4 Hz, 1H), 3.25 (dd, J=7.2, 14.4 Hz, 1H), 3.34 (s, 3H), 3.71 (s, 3H), 4.21 (m, 2H), 4.30 (m, 1H),4.63 (s, 2H), 6.90 (d, J=7.2 Hz, 2H), 7.12 (d, J=7.2 Hz, 2H), 7.22 (d, J=7.3 Hz, 1H), 7.33, (m, 5H), 7.63 (d, J=7.3 Hz, 2H), 8.06 (s, 1H), MS (M+1, m/z): 614.4. Anal. Calculated. for C$_{35}$H$_{39}$N$_3$O$_4$S.HCl.1.25H$_2$O: C, 62.48; H, 6.21; N, 6.24; Found: C, 62.44; H, 6.30; N, 6.25.

Example 2

Preparation of (R)-3-[2-cyano-4-N-[4-methylphenylsulfonyl]aminophenoxy]-1-[1,1-dimethyl-2-(4-methoxyphenyl)ethylamino]-propan-2-ol hydrochloride salt a) 2-Hydroxyl-5-[[N-4-methylphenyl]sulfonyl] aminobenzonitrile A mixture of the compound of Example 1(d) (0.50 g, 1.6542 mmol), PhSiMe$_3$ (0.40 g, 2.5 mmol), and iodine (0.63 g, 2.5 mmol) was heated at 130° C. in 3 h. The mixture was cooled and added saturated aqueous NaHSO$_3$, extracted with EtOAc. The organic extracts were washed with H$_2$O, brine, dried over MgSO$_4$, filtered, concentrated, and purified by flash column chromatography (40% EtOAc/Hexane) to afford the title compound (0.25 g, 51%) as a light yellow solid. $^1$H NMR (400 MHz, CDCl$_3$): d 2.49 (s, 3H), 4.68 (s, 2H), 6.80 (d, J=9.1 Hz, 2H), 7.01 (d, 2.7 Hz, 1H), 7.25 (m, 7H), 7.50 (d, J=9.1 Hz, 2H), 9.55 (s, 1H).

b) 2-Cyano-4-N-[4-methylphenyl]sulfonyl]amino]phenyl glycidol

A mixture of the compound of Example 2(a) (0.25 g, 0.8 mmol), K$_2$CO$_3$ (0.12 g, 0.9 mmol), and 2R-(−)-glycidyl-3-nitrobenzenesulfonate (0.2 g, 0.9 mmol) in acetone (5 mL) was refluxed in 24 h. The mixture was cooled, concentrated, taken up in H$_2$O, extracted with EtOAc(3×). The organic extracts were washed with saturated NaHCO$_3$, brine, dried over MgSO$_4$, filtered, concentrated, and purified by flash column chromatography (60% EtOAc/Hexane) to afford the title compound (0.15 g, 65%) as an off white foam. $^1$H NMR (400 MHz, CDCl$_3$): d 2.29 (s, 3H), 2.85 (t, J=4.5 Hz, 1H), 2.95 (t, J=4.5 Hz, 1H), 3.40 (m, 1H), 4.10 (dd, J=5.4, 11.4 Hz, 1H), 4.43 (dd, J=2.6, 11.4 Hz, 1H), 4.68 (s, 2H), 6.80 (d, J=9.1 Hz, 2H), 7.01 (d, J=9.3 Hz, 1H), 7.25 (m, 2H), 7.50 (d, J=9.1 Hz, 2H), 9.55 (s, 1H).

c) N-[2R-Hydroxy-3-[[2-cyano-4-[N-benzyl-N-[4-methylphenyl]sulfonyl]amino]phenoxy]propyl-1,1-dimethyl-2-[4-methoxyphenyl]ethylamine hydrochloride A mixture of the compound of Example 2(b) (0.22 g, 0.8 mmol), LiClO$_4$ (0.21 g, 0.1.5 mmol), and 4-methoxyphenyl-1,1-dimethyl ethylamine(0. 16 g, 0.9 mmol) in dried acetonitrile (5 mL) was heated at reflux in 24 h. The mixture was cooled and concentrated, taken up in H$_2$O, extracted with EtOAc (3×). The combined organic extracts were washed with brine, dried over MgSO$_4$, filtered, concentrated, and purified by flash column chromatography (3% MeOH/CH$_2$Cl$_2$) to afford as a colorless oil which was stirred in methanol and added 4M HCl, concentrated, and triturated in ether to give the title compound (64 mg, 16%) as a yellow foam. $^1$H NMR (400 MHz, DMSO-D$_6$): d 1.09 (s, 3H), 1.1(s, 3H), 2.64 (s, 2H), 3.10 (dd, J=7.2, 14.4 Hz, 1H), 3.25 (dd, J=7.2, 14.4 Hz, 1H), 3.34 (s, 3H), 3.71 (s, 3H),4.21 (m, 2H), 4.30 (m, 1H),5.90 (d, J=7.6 Hz, 1H), 6.90 (d, J=7.2 Hz, 2H), 7.12 (d, J=7.2 Hz, 2H), 7.22 (d, J=7.3 Hz, 1H), 7.33, (m, 5H), 7.63 (d, J=7.3 Hz, 2H), 8.06 (s, 1H), 10.47 (s, 1H). MS (M+1, n/z): 524.4. Anal. Calcd. for C$_{28}$H$_{33}$N$_3$O$_5$S.HCl: C, 60.05; H, 6.1 1; N, 7.50; Found: C, 60.40; H, 6.30; N, 7.25.

Example 3

Preparation of (R)-3-[2-cyano-4-[N-methyl-N-[4-methylphenylsulfonyl]amino]phenoxy]-1-[1,1-dimethyl-2-(4-methoxyphenyl)ethylamino]-propan-2-ol hydrochloride salt a) 2-Methoxy-5-[[N-4-methylphenyl]sulfonyl-N-benzyl] aminobenzonitrile To a stirred suspension of NaH (pre-washed with hexane, 60% oil, 0.080 g, 1.9 mmol)) in THF (15 mL) was added compound from Example 1(c) (0.50 g, 1.6 mmol) in portions. After stirring at RT for 1 h, methyl iodide (0.28 g, 1.9 mmol) was added, and refluxed in 4 h. The mixture was cooled, taken up in H$_2$O, extracted with EtOAc. The organic extracts were washed with brine, dried over MgSO$_4$ and concentrated to give the title compound (0.45 g, 86%) as a yellow solid. $^1$H NMR (400 MHz, CDCl$_3$): d 2.49 (s, 3H), 3.10 (s, 3H), 3.87 (s, 3H), 6.92 (d, J=9.1 Hz, 1H), 7.11 (d, 2.7 Hz, 1H), 7.25 (d, J=8.1 Hz, 2H), 7.45 (m, 3H).

b) 2-Hydroxyl-5-[N-methyl-N-[4-methylphenylsulfonyl] amino]benzonitrile

A mixture of the compound of Example 3(a) (0.45 g, 1.4 mmol), PhSiMe$_3$ (0.42 g, 2.8 mmol), and iodine (0.72 g, 2.8 mmol) was heated at 130° C. in 3 h. The mixture was cooled and added saturated aqueous NaHSO$_3$, extracted with EtOAc. The organic extracts were washed with H$_2$O, brine, dried over MgSO$_4$, filtered, concentrated, and purified by flash column chromatography (40% EtOAc/Hexane) to afford the title compound (0.214 g, 50%) as a light yellow oil. $^1$H NMR (400 MHz, CDCl$_3$): d 2.49 (s, 3H), 3.10 (s, 3H), 6.92 (d, J=9.1 Hz, 1H), 7.11 (d, 2.7 Hz, 1H), 7.25 (d, J=8.1 Hz, 2H), 7.45 (m, 3H).

c) 2-Cyano-4-[N-benzyl-N-[4-methylphenylsulfonyl] amino]phenyl glycidol

A mixture of the compound of Example 3(b) (0.2 g, 0.7 mmol), K$_2$CO$_3$ (0.20 g, 1.4 mmol), and 2R-(−)-glycidyl-3-nitrobenzenesulfonate (0.2 g, 0.7 mmol) in acetone (5 mL) was refluxed in 24 h. The mixture was cooled, concentrated, taken up in H$_2$O, extracted with EtOAc (3×). The organic extracts were washed with saturated NaHCO$_3$, brine, dried over MgSO$_4$, filtered, concentrated to afford the title compound as a tan solid (0.24 g, 95%). $^1$H-NMR (400 MHz, CDCl$_3$): d 2.44 (s, 3H), 2.85 (t, J=4.5 Hz, 1H), 2.97 (t, J=4.5 Hz, 1H), 3.15 (s, 3H), 3.42 (m, 1H), 4.12 (dd, J=5.4, 11.4 Hz, 1H), 4.42 (dd, J=2.6, 11.4 Hz, 1H), 6.97 (d, J=9.1 Hz, 1H), 7.13 (d, J=2.7 Hz, 1H), 7.27 (d, J=8.1 Hz, 2H), 7.41 (m, 3H).

d) (R)-3-[2-cyano-4-[N-methyl-N-[4-methylphenylsulfonyl]amino]phenoxy]-1-[1,1-dimethyl-2-(4-methoxyphenyl)ethylamino]-propan-2-ol hydrochloride salt A mixture of th e compound of Example 3(c) (0.24 0.7 mmol), LiClO$_4$ (0.092 g, 0.7 mmol), and 4-methoxyphenyl-1,1-dimethyl ethylamine (0.12 g, 0.7 mmol) in dried acetonitrile (5 mL) was heated at reflux in 24 h. The mixture was cooled and concentrated, taken up in H$_2$O, extracted with EtOAc (3×). The combined organic extracts were washed with brine, dried over MgSO$_4$, filtered, concentrated, and purified by flash column chromatography (5% MeOH/CH$_2$Cl$_2$) to afford an off white foam which was stiffed in methanol and added 4M HCl, concentrated, and triturated in ether to aive the title compound as an off white solid (0.20 g, 55%). $^1$H NMR (400 MHz, DMSO-d$_6$): d 1.09 (s, 3H), 1.11(s, 3H), 2.41 (s, 3H), 2.64 (s, 2H), 3.10 (dd, J=7.2, 14.4 Hz, 3H), 3.25 (dd, J=7.2, 14.4 Hz, 1H), 3.08 (s, 3H), 3.78 (s, 3H), 3.98 (m, 1H), 4.20 (t, J=7.2 Hz, 2H), 4.60 (s, 1H), 6.80 (d, J=10.8 Hz, 2H), 6.95 (d, J=10.8 Hz, 1H), 7.06 (d, J=10.8 Hz, 1H), 7.11 (d, J=3.6 Hz, 1H), 7.27 (d, J=10.8 Hz, 2H), 7.36 (d, J 10.8 Hz, 1H), 7.41 (d, J=10.8 Hz, 2H). MS (M+1, m/z): 524.4. Anal. Calcd. for C$_{29}$H$_{35}$N$_3$O$_5$S.HCl:C, 60.67; H, 6.32; N, 7.32; Found: C, 60.40; H, 6.30; N, 7.50.

Example 4
Pretparation of (R)-3-[2-cyano-4-[N-benzyl-N-[methylsulfonyl]amino]phenoxy]-1-[1,1-dimethyl-2-(4-methoxyphenyl)ethylamino]-propan-2-ol hydrochloride salt a) 5-Amino-2-fluorobenzonitrile A mixture of 5-nitro-2-fluorobenzonitrile (10 g, 60.2 mmol), Fe powder (17 g, 0.3 mol), and NH$_4$Cl (1.7 g, 30 mmol) in EtOH/H$_2$O (100 mL, 9:1) was heated at reflux in 2 h. The mixture was filtered at hot. The filtrate was concentrated, taken up in H$_2$O, stirred, filtered air-dried to obtain the title solid as a tan solid, (5.0 g, 71%). $^1$H NMR (400 MHz, DMSO-d$_6$): d 5.54 (s, 2H), 6.85 (m, 2H), 7.16 (t, J=8.1 Hz, 1H).

b) $^2$-Fluoro-5-[N-methylsulfonyl]aminobenzonitrile

To a stirred, cooled (0° C.) mixture of the compound of Example 4(a) (5.0 g, 36.7 mmol), and Et$_3$N (3.9 g, 38.5 mol) in CH$_2$Cl$_2$ (20 mL) was added methanesulfonyl chloride (4.42 g, 38.5 mmol). After stirring at RT overnight, the mixture was quenched with H$_2$O, extracted with ether. The combined organic extracts were washed with brine, dried over MgSO$_4$, filtered, concentrated to afford the title compound as a brown solid (6.8 g, 87%). $^1$H NMR (400 MHz, DMSO-d$_6$): d 3.10 (s, 3H), 7.50 (m, 2H), 7.76 (t, J=8.1 Hz, 1H), 10.4 (s, 1H).

c) 2-Fluoro-5-[[-N-methyl]sulfonyl-N-benzyl]aminobenzonitrile

To a stirred suspension of NaH (pre-washed with hexane, 60% oil, 0.20 g, 4.7 mmol) in DMF (15 mL) was added the compound from Example 4(b) (1.0 g, 4.7 mmol) in fluorobenzonitrile portions. After stirring at RT for 1 h, benzyl bromide (0.80 g, 4.7 mmol) was added, and stirred overnight, quenched with H$_2$O, extracted with ether, washed with brine, dried over MgSO$_4$, concentrated, and purified by flash column chromatography (50% EtOAc/Hexane) to afford the title compound as an orange oil (1.03 g, 73%). $^1$H NMR (400 MHz, CDCl$_3$): d 3.05 (s, 3H), 4.80 (s, 2H), 7.20 (m, 6H), 7.50 (m, 2H).

d) 2-Hydroxy-5-[N-benzyl-N-methylsulfonyl]aminobenzonitrile

A mixture of the compound from Example 4(c) (2 g, 6.7 mmol), KOAc (1 g, 10.1 mmol), and 18-crown-6 ether (2.7 g 10.17 mmol) in MeCN (30 mL) was heated at reflux for 24 h. The mixture was cooled and 20 mL of 1N NaOH were added, stirred at RT for 48 h, concentrated, extracted with ether (discarded). The aqueous layer was acidified, and extracted with EtOAc, dried over MgSO$_4$, and concentrated to give the title compound as an orange foam (1.2 g, 57%). $^1$H NMR (400 MHz, CDCl$_3$): d 3.05 (s, 3H), 4.75 (s, 2H), 6.90 (d, J=9.1 Hz, 1H), 7.31 (m, 7H).

e) 2-Cyano-4-[[N-benzyl-N-methylsulfonyl]amino]phenyl glycidol

A mixture of the compound of Example 4(d) (1.1 g, 3.8 mmol), K$_2$CO$_3$ (1.06 g, 7.6 mmol), and 2R-(-)-glycidyl-3-nitrobenzenesulfonate (1.0 g, 3.8 mmol) in acetone (20 mL) was heated at reflux in 24 h. The mixture was cooled, concentrated, taken up in H$_2$O, extracted with EtOAc(3×). The organic extracts were washed with saturated NaHCO$_3$, brine, dried over MgSO$_4$, filtered, and concentrated to afford the title compound as a yellow solid (1.4 g, 99%). $^1$H NMR (400 MHz, CDCl$_3$): d 2.85 (t, J=4.5 Hz, 1H), 2.97 (t, J=4.5 Hz, 1H), 3.00 (s, 3H), 3.40 (m, 1H), 4.05 (dd, J=5.4, 11.4 Hz, 1H), 4.42 (dd, J=2.6, 11.4 Hz, 1H), 4.79 (s, 2H), 6.97 (d, J=9.1 Hz, 1H), 7.24 (m, 5H), 7.37(dd, J=2.6, 9.1 Hz, 1H), 7.41 (d, J=2.6, 1H).

f) (R)-3-[2-cyano-4-[N-benzyl-N-[methylsulfonyl]amino]phenoxy]-1-[1,1-dimethyl-2-(4-methoxyphenyl)ethylamino]-propan-2-ol hydrochloride salt A mixture of the compound from Example 4(e) (0.50 g, 1.4 mmol), LiClO$_4$ (0.19 g, 1.4 mmol), and 4-methoxyphenyl-1,1-dimethyl ethylamine(0.25 g, 1.4 mmol) in dried acetonitrile (5 mL) was heated at reflux in 24 h. The mixture was cooled and concentrated, taken up in H$_2$O, extracted with EtOAc (3×). The combined organic extracts were washed with brine, dried over MgSO$_4$, filtered, concentrated, and purified by flash column chromatography (4% MeOH/CH$_2$Cl$_2$) to afford a yellow foam which was stirred in methanol and added 4M HCl, concentrated, and triturated in ether to give the title compound as a yellow foam (0.70 g, 87%). $^1$H NMR (400 MHz, DMSO-d$_6$): d 1.09 (s, 3H), 1.11(s, 3H), 2.41 (s, 3H), 2.64 (s, 2H), 3.10 (dd, J=7.2, 14.4 Hz, 1H), 3.25 (dd, J=7.2, 14.4 Hz, 1H), 3.08 (s, 3H), 3.78 (s, 3H), 3.98 (m, 1H), 4.20 (t, J=7.2 Hz, 2H), 4.60 (s, 1H), 6.80 (d, J=10.8 Hz, 2H), 6.95 (d, J=10.8 Hz, 1H), 7.06 (d, J=10.8 Hz, 1H), 7.11 (d, J=3.6 Hz, 1H), 7.27 (d, J=10.8 Hz, 2H), 7.36 (d, J 10.8 Hz, 1H), 7.41 (d, J=10.8 Hz, 2H). MS (M+1, m/z): 524.4. Anal. Calcd. for C$_{29}$H$_{35}$N$_3$O$_5$S.HCl: C, 60.67; H, 6.32; N, 7.32; Found: C, 60.40; H, 6.30; N,7.50.

Example 5
Preparation of (R)-3-[2-cyano-4-[N-methyl-N-[methylsulfonyl]amino]phenoxy]-1-1,1-dimethyl-2-(4-methoxyphenyl)ethylamino]-propan-2-ol hydrochloride salt a) 2-Methoxy-5-[[N-methyl]sulfonyl]aminobenzonitrile Following the procedure in Example 4(b), the title compound was prepared as a tan solid (2.50 g, 82%). $^1$H NMR (400 MHz, CDCl$_3$): d 3.02 (s, 3H), 3.95 (s, 3H), 7.25 (d, J=9.1 Hz, 1H), 7.72 (d, J=9.1 Hz, 1H), 7.85 (s, 1H), 9.60 (s, 1H).

b) 2-Methoxy-5-[N-methyl-N-methylsulfonyl]aminobenzonitrile

Following the procedure in Example 3(a), the title compound was prepared as a yellow solid (0.44 g, 83%). $^1$H NMR (400 MHz, DMSO-d$_6$): d 3.02 (s, 3H), 3.25(s, 3H), 3.95 (s, 3H), 7.25 (d, J=9.1 Hz, 1H), 7.72 (d, J=9.1 Hz, 1H), 7.85 (s, 1H).

c) 2-Hydroxy-5-[N-methyl-N-methylsulfonyl]aminobenzonitrile

Following the Example 3(b) the title compound was prepared as a tan solid (0.068 g, 16%). $^1$H NMR (400 MHz, DMSO-d$_6$): d 3.02 (s, 3H), 3.25(s, 3H), 7.25 (d, J=9.1 (Hz, 1H), 7.72 (d, J=9.1 Hz, 1H), 7.85 (s, 1H).

d) 2-Cyano-4-[[N-methyl-N-methylsulfonyl]amino] phenyl glycidol

Following the procedure in Example 3(c), the title compound was prepared as a brown oil (0.083, 99%). $^1$H NMR (490 MHz, CDCl$_3$): d 2.45 (s, 3H), 2.85 (t, J=4.5 Hz, 1H), 2.97 (t, J=4.5 Hz, 1H), 3.00 (s, 3H), 3.40 (m, 1H), 4.05 (dd, J=5.4, 11.4 Hz, 1H), 4.42 (dd, J=2.6, 11.4 Hz, 1H), 6.97 (d, J=9.1 Hz, 1H), 7.45 (m, 2H).

e) (R)-3-[2-cyano-4-[N-methyl-N-[methylsulfonyl] amino]phenoxy]-1-[1,1-dimethyl-2-(4-methoxyphenyl) ethylamino]-propan-2-ol hydrochloride salt Following the procedure in Example 3(d), the title compound was prepared as a tan solid (0.07 g, 48%). MS (M+1, m/z): 462.2 Anal. Calcd. for C$_{23}$H$_{31}$N$_3$O$_5$S.HCl H$_2$O: C, 53.52; H, 6.64; N, 8.13; Found: C, 53.39; H, 6.38; N,7.94.

Example 6

Preparation of (R)-3-[2-cyano-4-[N-methylsulfonylamino] phenoxy]-1-[1,1-dimethyl-2-(4-methoxyphenyl) ethylamino]-propan-2-ol hydrochloride salt A solution of the compound of Example 4(f) (0.30, 0.5 mmol) in MeOH (5 mL) was hydrogenated in 10% Pd/C (0.07 g) at RT in overnight. The catalyst was filtered, and the filtrate was concentrated, and purified by flash column chromatography (7% MeOH/CH$_2$Cl$_2$) to afford a yellow oil which was dissolved in MeOH and added 4M HCl in p-dioxane, concentrated, triturated in ether to afford the title compound as a yellow foam (0.08 g, 32%). $^1$H NMR (400 MHz, CDCl$_3$): d 1.04 (s, 3H), 1.06 (s, 3H), 2.62 (s, 2H), 2.82 (dd, J=7.2, 14.4 Hz, 1H), 2.92 (dd, J=7.2, 14.4 Hz, 1H), 2.97 (s, 3H), 3.77 (s, 3H), 3.95 (m, 1H), 4.09 (d, J=7.2 H), 6.80 (d, J=10.8 HZ, 2H), 7.05 (d, J=10.8 Hz, 1H), 7.08 (d, J=10.8 Hz, 2H), 7.42 (m, 2H). MS (M+1, m/z): 448.3. Anal. Calcd. for C$_{22}$H$_{29}$N$_3$O$_5$S.HCl.2H$_2$O: C, 51.10; H, 6.62; N, 8.12; Found: C, 50.86; H, 6.42; N,7.90.

Example 7

Preparation of (R)-3-[2-cyano-4-[N-benzyl-N-[methylsulfonyl]amino]phenoxy]-1-[1,1-dimethyl-2-(2-nauhthyl)ethylamino]-propan-2-ol hydrochloride salt A mixture of Experiment 4e (0.36 g, 1 mmol), LiClO$_4$ (0.14 g, 1 mmol), and 1,1-dimethyl-2-[2-naphthyl] ethylamine (0.2 g, 1 mmol) in dried acetonitrile (8 mL) was heated at reflux in 24 h. The mixture was cooled and concentrated, taken up in H$_2$O, extracted with EtOAc (3×). The combined organic extracts were washed with brine, dried over MgSO$_4$, filtered, concentrated, and purified by flash column chromatography (3% MeOH/CH$_2$Cl$_2$) to afford the title compound as a yellow foam (0.40 g, 71%). $^1$H NMR (400 MHz, CDCl$_3$): d 1.09 (s, 3H), 1.11(s, 3H), 2.81 (dd, J=7.2, 14.4 Hz, 1H), 2.85 (d, J=3.6 Hz, 2H), 2.90 (s, 3H), 2.96 (dd, J=7.2, 14.4 Hz, 1H), 3.91 (m, 1H), 4.04 (d, J=7.2 Hz, 2H), 4.76 (s, 2H), 6.95 (d, J=7.2 Hz, 1H), 7.27 (m, 11H), 7.55 (s, 1H), 7.80 (m, 2H). MS (M+1, m/z): 468.2. Anal. Calcd. for C$_{32}$H$_{35}$N$_3$O$_4$S.H$_2$O: C, 66.75; H, 6.47; N, 7.29; Found: C, 66.84; H, 6.20; N, 7.50.

Example 8

Preparation of (R)-3-[2-cyano-4-[N-[methylsulfonyl]amino] phenoxy]-1-[1,1-dimethyl-2-(2-nayhthyl)ethylamino]-propan-2-ol hydrochloride salt A solution of the compound from Example 7(a) (0.20, 0.3 mmol) in MeOH (5 mL) was hydrogenated in 10% Pd/C (0.06 g) at RT in overnight. The catalyst was filtered, and the filtrate was concentrated, and purified by flash column chromatography (5% MeOH/CH$_2$Cl$_2$) to afford a yellow oil which was dissolved in MeOH and added 4M HCl in p-dioxane, concentrated, triturated in ether to afford the title compound as a yellow solid (0.08 g, 44%). $^1$H NMR (400 MHz, CDCl$_3$): d 1.09 (s, 3H), 1.11(s, 3H), 2.81 (dd, J=7.2, 14.4 Hz, 1H), 2.85 (d, J=3.6 Hz, 2H), 2.90 (s, 3H), 2.96 (dd, J=7.2, 14.4 Hz, 1H), 3.91 (m, 1H), 4.04 (d, J=7.2 Hz, 2H), 6.95 (d, J=7.2 Hz, 1H), 7.27 (m, 6H), 7.55 (s, 1H), 7.80 (m, 2H). MS (M+1, m/z): 468.2. Anal. Calcd. for C$_{25}$H$_{29}$N$_3$O$_4$S.HCl.0.25H$_2$O: C, 55.60; H, 6.34; N, 7.70; Found: C, 55.60; H, 6.20; N, 7.50.

Example 9

Preparation of N-[(R)-2-Hydroxy-3-(2-cyano-3-chlorophenoxy)propyl-1,1-dimethyl-2-benzyloxyethylamine To a 0° C. mixture of NaH (0.8 g, 33.7 mmole) in DMF (15 mL) was added slowly 3-amino-3-methylpropanol. After stirring at 0° C. for 3 h, the reaction was allowed to warm to room temperature and benzyl bromide (5.76 g, 33.7 mmole) was added slowly then stirred at room temperature an additional 18 h. H$_2$O (150 mL) was added to quench the reaction then the amine was extracted into diethyl ether (3×100 mL). The organic layers were combined, washed with saturated NaCl(aq) (100 mL), dried over sodium sulfate, and concentrated in vacuo. The residue was purified by short path distillation to afford 2.1 g of the title compound. GC/EI-MS m/z (rel. int.) 179 (M+,0.0), 92 (6), 91 (75), 88 (8), 77 (11), 65 (26), 62 (6), 58 (100), 57 (6), 51 (7), 43 (5), 42 (17), 41 (10).

Example 10

Preparation of (R)-1-[1,1-dimethyl-2-(4-methoxyphenyl) ethylamino]-3-[2-cyano-4-(N,N-dipropylaminocarbonyl) phenoxy]-propan-2-ol hydrochloride salt a) Preparation of 2-cyano-4 (N,N-dipropyl aminocarbonyl)methoxy phenol.

Methyl-3-cyano-4-methoxy benzoate (5 g, 26 mmol Lancaster) was dissolved in 100 mL of methanol and treated with 1M NaOH aqueous (52 mL, 52 mmol) for 5 h. at room temperature. The reaction was evaporated to half volume, acidified with aqueous 3N HCl, extracted with CHCl3, dried over anhydrous MgSO4, filtered and evaporated to give 3.5 g of the corresponding acid which was carried on with out further purification.

The material from above (3 g, 16.9 mmol) was dissolved in 40 mL of benzene and 1 mL of DMF and treated with oxalyl chloride (1.52 mL, 17.4 mmol). The resulting reaction mixture was stirred at room temperature for 1.5 h. The reaction was cooled to 0° C. and treated with DIEA (4.55 mL, 26.1 mmol) and then split into four equal portions. One portion (6.33 mmol) was treated with dipropylamine (880 uL, 6.33 mmol) and then stirred at room temperature for 16 h. The reaction was diluted with EtOAc, washed with brine, dried over anhydrous MgSO4, filtered and evaporated. The residue was purified by flash chromatography (silica gel 5% MeOH in CHCl3) to give 820 mg of the above named compound. $^1$H NMR (CDCl3, 250 MHz) d 7.6–7.3 (2H, m), 7.02 (1H, d), 3.97 (3H, s), 3.4–3.2 (4H, m), 1.6 (4H, br s), 0.9–0.8 (6H, m).

b) Preparation of 2-cyano-4-(N,N-dipropylaminocarbonyl)phenol

The compound of Example 10(a) (820 mg, 3.1 mmol) from above was dissolved in 40 mL of collidine and treated with LiI (845 mg, 6.31 mmol) and stirred at reflux for 16 h. The reaction was taken into 3N HCl, extracted with EtOAc, dried over anhydrous MgSO$_4$, filter and evaporated to give 630 mg (2.04 mmol) of the above named compound contaminated with approximately 20% of unreacted methyl ether. $^1$H NMR (CDCl$_3$, 250 MHz) d 7.6–7.3 (2H, m), 7.02 (1H, d), 3.4–3.2 (4H, m), 1.6 (4H, br s), 0.9–0.8 (6H, m).

c) Preparation of [2-cyano-4-(N,N-dipropylaminocarbonyl)]phenyl R-glycidyl ether The compound of example 10(b) (470 mg, 2.04 mmol), $K_2CO_3$ (563 mg, 4.08 mmol), and (2R)-(-)-glycidyl-3-nitrobenzenesulfonate (528 mg, 2.04 mmol) were heated in acetone (30 mL) at reflux for 18 h. The solvent was concentrated in vacuo to half of the volume, poured into $H_2O$ and extracted with EtOAc. The combined organic extracts were dried ($MgSO_4$), evaporated and the residue purified by column chromatography (silica gel, 80% EtOAc/hexanes) to give the title compound as a clear oil. $^1H$ NMR ($CDCl_3$, 250 MHz) d 7.6–7.3 (2H, m), 7.02 (1H, d), 4.47–4.41 (1H, d of d), 4.13–4.08 (1H, m) 3.4–3.2 (5H, m), 2.86–2.83 (2H, m) 1.6 (4H, br s), 0.9–0.8 (6H, m).

d) Preparation of (R)-1-[1,1-dimethyl-2-(4-methoxyphenyl)ethylamino]-3-[2-cyano-4-(N,N-dipropylaminocarbonyl)phenoxy]-propan-2-ol A solution of the compound of Example 10 (c) (380 mg, 2.1 mmol) and lithium perchlorate (426 mg, 4.02 mmol) in ethanol (25 mL) was heated at reflux for 12 h. The reaction was evaporated and purified by flash chromatography (silica gel 5% MeOH in chloroform) to give the free base of the above name compound. This material was dissolved in dichloromethane and treated with 1 molar equivalent of 1N HCl/methanol. Upon addition of ether, crystals formed and were subsequently collected and dried in a vacuum oven to give 150 mg of the title. ESMS $[M+H]^+=482$; $^1H$ NMR ($CDCl_3$, 360 MHz @ 300 K) d 7.7–7.76 (2H, m), 7.2–7.1 (3H, m), 6.9–6.8 (2H, m), 4.3–4.2 (4H, m), 3.76 (3H, s), 3.5–3.1 (6H, m), 2.95)2H, s), 1.7–1.5 (4H, m), 1.3 (6H, d), 0.9–0.7 (6H, m).

Example 11

Preparation of (R)-1-[1,1-dimethyl-2-(4-methoxyphenyl)ethylamino]-3-[2-cyano-4-(N-propylamino)phenoxy]-propan -2-ol a) Preparation of (R)-1-[1,1-dimethyl-2-(4-methoxyphenyl)ethylamino]-3-[2-cyano-4-(N-propylamino)phenoxy]-propan-2-ol hydrochloride salt Following the procedure outlined in Example 10 but substituting propyl amine for dipropylamine in Example 10(a) 7 mg of the title compound was prepared. ESMS $[M+H]^+=440$; $^1H$ NMR ($CDCl_3$, 360 MHz) @ 300 K d 7.7–7.76 (2H, m), 7.2–7.1 (3H, m), 6.9–6.8 (2H, m), 4.3–4.2 (4H, m), 3.76 (3H, s), 3.5–3.1 (4H, m), 2.95 (2H, s), 1.7–1.5 (2H, m), 1.3 (6H, d), 0.9–0.7 (3H, m).

Example 12

Preparation of (R)-1-[1,1-dimethyl-2-(4-methoxyDhenyl)ethylamino]-3-[2-cyano-4-(N-piperidinylcarbonyl)phenoxy]-propan-2-ol hydrochloride salt a) Preparation of (R)-1-[1,1-dimethyl-2-(4-methoxyphenyi)ethylamino]-3-[2-cyano-4-(N-piperidinylcarbonyl)phenoxy]-propan-2-ol Following the procedure outlined in Example 10 but substituting piperidine for dipropylamine in Example 10(a.) 150 mg of the title compound was prepared. ESMS $[M+H]^+=467$, $^1H$ NMR ($CDCl_3$, 360 MHz, @ 300 K) d 7.6–7.75 (2H, m), 7.1–7.0 (3H, m), 6.8–6.7 (2H, m), 4.13–3.91 (3H, m), 3.76 (3H, s), 2.95–2.8 (2H, m), 2.62 (2H, m), 1.6–1.5 (6H, m), 1.03 (6H, d).

Example 13

Preparation of (R)-1-[1,1-dimethyl-2-(4-methoxyphenyl)ethylamino]-3-[2,3-dichloro-4-(N-morpholynylcarbonyl)phenoxy]-propan-2-ol hydrochloride salt (a) 2,3-Dichloro-4-bromoanisole.

Bromination of 2,3-dichloroanisole (Aldrich, 1.0 g, 5.65 mmol) using the method of Wyrick, S. D.; Smith, F. T.; Kemp, W. E.; Grippo, A. A. *Journal of Medicinal Chemistry*, 1987, Vol. 30, No.10 P. gave 729 mg (50%) of the title compound as a white solid. $^1H$ NMR (250 MHz, $CDCl_3$) d 7.51 (d, J=8.5 Hz, 1H), 6.77 (d, J=8.5 Hz, 1H), 3.92 (s, 3H).

(b) 2,3-Dichloro-4-(morpholinocarbonyl)anisole

The compound of Example 13(a) (150 mg, 0.59 mmol) was dissolved in DMF (8 mL) and morpholine was added (0.52 mL, 5.9 mmol). Argon was bubbled through the solution for 5 min followed by CO for 5 min. Tetrakis (triphenylphosphine)palladium(0) was added (75 mg, 0.065 mmol), CO was bubbled for an additional 5 min, and the mixture was stirred at 110° C. for 4 h under CO (balloon). DMF was evaporated at reduced pressure and then azeotroped with xylenes. The residue was purified by flash chromatography (silica gel, .2.5×20.5 cm, 50% EtOAc/hexanes) to give 90 mg (53%) of the title compound. $^1H$ NMR(400 MHz, $CDCl_3$) d 7.19 (d, J=9.5 Hz, 1H), 6.92 (d, J=9.5 Hz, 1H), 3.94 (s, 3H), 3.93–3.83 (m, 1H), 3.81–3.74 (m, 3H), 3.74–3.56 (m, 2H), 3.34–3.18 (m, 2H).

(c) 2,3-Dichloro-4-(morpholinocarbonyl)phenol

The compound of Example 13(b) (76 mg, 0.26 mmol) was demethylated following the method of I. T. Harrison *J.C.S. Chem Comm.*, 1969, p. 616 to give the title compound as a crude brown oil which was used in the next step without further purification. $^1H$ NMR(400 MHz, $CDCl_3$) d 7.07 (d, J=10.5 Hz, 1H), 7.03 (d, J=10.5 Hz, 1H), 3.92–3.82 (m, 1H), 3.82–3.72 (m, 3H), 3.72–3.55 (m, 2H), 3.36–3.19 (m, 2H).

(d) 2,3-Dichloro-4-(N-morpholinocarbonyl)phenyl glycidyl ether.

The compound of Example 13(c) (72 mg), (2R)-(-)-glycidyl 3-nitrobenzenesulfonate (85 mg, 0.33 mmol), and $K_2CO_3$ (50 mg, 0.36 mmol) were stirred at reflux in acetone for 14 h. The reaction mixture was cooled, filtered, evaporated, and the residue was purified by flash chromatography (silica gel, 2.5×17.5 cm, 50%–70%–100% EtOAc/hexanes) to give 42 mg (49%) of the title compound. $^1H$ NMR(250 MHz, $CDCl_3$) d 7.17 (d, J=8.5 Hz, 1H), 6.95 (dd, J=7.9, 7.2 Hz, 1H), 4.46–4.31 (m, 1H), 4.08–3.98 (m, 1H), 3.95–3.85 (m, 1H), 3.85–3.72 (m, 3H), 3.72–3.53 (m, 2H), 3.46–3.36 (m, 1H), 3.36–3.15 (m, 2H), 3.00–2.78 (m, 2H).

(e) (R)-1-[1,1-diethyl-2-(4-methoxyphenyl)ethylamino]-3-[2,3-dichloro-4-(N-morpholinocarbonyl)phenoxy]-propan-2-ol hydrochloride salt The compound of 13(d) (42 mg, 0.127 mmol) and 1,1-dimethyl-2-(4-methoxyphenyl)ethylamine (28 mg, 0.156 mmol) were dissolved in $CH_3CN$ (10 mL), $LiClO_4$ (21 mg, 0.197 mmol) was added, and the mixture was stirred at reflux for 18 h. The mixture was concentrated in vacuo and purified by flash chromatography (silica gel, 2.5×17.5 cm, 200 mL 5% $MeOH/CHCl_3$, 100 mL 10% $MeOH/CHCl_3$) to give 55 mg (85%) of the title compound as its free base. This material was converted to the corresponding HCl salt by dissolving the free base in $CH_2Cl_2$, treating the resulting solution with 105 uL of HCl in MeOH and then first evaporating the $CH_2Cl_2$ followed by evaporating from hexanes. MS (ES) m/e 511.2 $(M+H]^+$; $^1H$ NMR(360 MHz, DMSO/TFA) d 8.58 (m, 2H), 7.39 (d, J=8.6, 1H), 7.29 (d, J=8.6, 1H), 7.16 (d, J=8.6, 2H), 6.92 (d, J=8.6, 2H), 4.30–4.11 (m, 3H), 3.76 (s, 3H), 3.73–3.61 (m, 4H), 3.58–3.51 (m, 2H), 3.40–3.28 (m, 1H), 3.21–3.07 (m, 3H), 2.92 (s, 2H), 1.23 (s, 6H).

Example 14

Preparation of (R)-3-[2-cyano-4-[N-methyl-N'-morpholinoureido]phenoxy]-1-[1,1-dimethyl-2-(2-naphthyl)ethylamino]-propan-2-ol;

a) 2-Methoxyl-5-N-[[4-morpholino]carbonyl]amino benzonitrile

To a stirred mixture of 2-methoxyl-5-aminobenzonitrile (2 g, 12.34 mmol), and pyridine (1.28 g, 16.2 mmol) in dried $CH_2Cl_2$ (20 mL) was added 4-morpholinecarbonyl chloride (2.42 g, 16.2 mmol). After stirring at RT for 24 h, the mixture was diluted with $CH_2Cl_2$ and washed with $H_2O$, brine, dried over $MgSO_4$, concentrated to give an orange solid (3.04 g, 86%) $^1H$ NMR: (400MHz, DMSO-$d_6$): d 3.23 (t, J=4.9 Hz, 4H), 3.47 (t, J=4.9 Hz, 4H), 3.9 (s, 3H), 6.89 (d, J=9 Hz, 1H), 7.3 (d, J=9 Hz, 1H), 8.01 (s, 1H).

b) 2-Methoxyl-5-[N-methyl-N-[[4-morphlino]carbonyl] amino] benzonitrile.

To a stirred suspension of NaH (60%, pre-washed with hexane, 0.2 g, 4.98 mmol) in dry DMF (10 mL) was added example 14a (1 g, 3.8 mmol). After stirring at RT in 1 h, methyl iodide (1.62 g, 11.5 mmol) was added and stirred overnight, taken up in $H_2O$, extracted with EtOAc. The organic extracts were washed with brine, dried over $MgSO_4$, concentrated to give a brown oil (1.0 g, 98%). $^1H$ NMR: (400MHz, DMSO-$d_6$): d 2.95 (s, 3H), 3.23 (t, J=4.9 Hz, 4H), 3.47 (t, J=4.9 Hz, 4H), 3.9 (s, 3H), 6.89 (d, J=9 Hz, 1H), 7.3 (d, J=9 Hz, 1H), 8.01 (s, 1H).

c) 2-Hydroxy-5-[N-methyl-N-[[4-morpholino]carbonyl] amino]benzonitrile.

Following the example 1e, the title compound was prepared as a yellow oil (0.33 g, 40%). $^1H$ NMR: (400MHz, DMSO-$d_6$): d 2.95 (s, 3H), 3.23 (t, J=4.9 Hz, 4H), 3.47 (t, J=4.9 Hz, 4H), 6.89 (d, J=9 Hz, 1H), 7.3 (d, J=9 Hz, 1H), 8.01 (s, 1H).

d) 2-Cyano-5-[N-methyl-N-[[4-morpholino]carbonyl] amino]phenyl glycidol.

Following the example 1f, the title compound was prepared as a brown oil (0.23 g, 60%). $^1H$ NMR (400MHz, DMSO-$d_6$): d 2.85 (t, J=4.5 Hz, 1H), 2.95 (s, 3H), 2.97 (t, J=4.5 Hz, 1H), 3.23 (t, J=4.9 Hz, 4H), 3.42 (m, 1H), 3.47 (t, J=4.9 Hz, 4H), 4.12 (dd, J=5.4, 11.4 Hz, 1H), 4.42 (dd, J=5.4, 11.4 Hz, 1H), 6.89 (d, J=9 Hz, 1H), 7.3 (d, J=9 Hz, 1H), 8.01 (s, 1H).

e) Synthesis of (R)-3-[2-cyano-4-[N-methyl-N'-morpholino]ureido]phenoxy]-1-[1,1-dimethyl-2-(2-naphthyl)ethylamino]-propan-2-ol.

Following the procedure in example 7, the title compound was prepared as an off white foam (0.6 g, 56%) $^1H$ NMR (400 MHz, DMSO-$d_6$): d 1.09 (s, 3H), 1.11 (s, 3H), 2.85 (t, J=4.5 Hz, 1H), 2.95 (s, 3H), 2.97 (t, J=4.5 Hz, 1H), 3.23 (t, J=4.9 Hz, 4H), 3.42 (m, 1H), 3.47 (t, J=4.9 Hz, 4H), 4.12 (dd, J=5.4, 11.4 Hz, 1H), 4.42 (dd, J=5.4, 11.4 Hz, 1H), 7.12 (d, J=7.2 Hz, 1H), 7.27 (m, 5H), 7.35 d, J=7.2 Hz, 1H), 7.55 (s, 1H), 7.67 (s, 1H), 7.76 (d, J=7.2 Hz, 1H). MS (m+1, m/z): 417.6. Anal. Calcd. for $C_{30}H_{36}N_4O_4$ 1.5$H_2O$: C, 66.28; H, 7.23; N, 10.3; Found: C, 66.61; H, 6.96; N, 9.92.

Example 15
N-[3-(2,3-dichloro-4-dipropylsulfamoyl)phenoxy-2(R)-hydroxypropyl]-2-(4-methoxyphenyl)-1,1-dimethylethylamine hydrochloride a) (2,3-dichloro-4-methoxy)phenylsufonylchloride 2,3-dichloroanisole (Aldrich, 9.0 g, 50.8 mmole) was utilized in the method of H. Harada et al *Chem Pharm Bull* (1987) 35(8) 3195–3214 to give the title compound as a white solid (13.3, 95%).

b) N,N-dipropyl-(2,3-dichloro-4-methoxy) phenylsulfonamide

The compound of 15(a) (8.0 g, 29.0 mmol) was dissolved in $CH_2Cl_2$ (200 mL) and dipropylamine (11.9 mL, 87.1 mmol) in EtOH (40 ml) was added at –20° C. The ice bath was removed and the mixture stirred 1.5 h. The mixture was poured into $H_2O$ and extracted with $CH_2Cl_2$. The combined organic extracts were washed with $H_2O$, brine concentrated in vacuo and azeotroped with toluene to yield the title compound as a light brown-tinted oil (9.8 g, 100%). $^1H$ NMR (400 MHz, CDCl$_3$) d 8.05 (d, J=10 Hz, 1H), 6.92 (d, J=10 Hz, 1H), 4.00 (s, 3H), 3.23 (t, J=8, 17 Hz, 4H), 1.52 (m, 4H), 0.83 (t, J=8, 13 Hz, 6H).

c) N,N-dipropyl-2,3-dichloro-4-hydroxyphenylsulfonamide

The compound from Example 15(b) (10.0 g, 29.4 mmol), $I_2$ (14.9 g, 58.8 mmol) and trimethylphenylsilane (15.1 mL, 88.2 mmol) were stirred together and heated to 110° C. for 18 h. The mixture was poured into aqueous $Na_2S_2O_3$, extracted with EtOAc, dried ($MgSO_4$), concentrated to dryness in vacuo and purified by column chromatography (silica gel, 40% EtOAc/Hexanes) to give a clear oil (9.2 g, 86%). $^1H$ NMR (400 MHz, CDCl$_3$) d 7.98 (d, J=10 Hz, 1H), 7.05 (d, J=10 Hz, 1H), 6.29 (bs, 1H), 3.24(t, J=9, 18 Hz, 4H), 1.56 (m, 4H), 0.84 (t, J=8,14 Hz, 6H).

d) [2,3-dichloro-4-(N,N-dipropylsulfamoyl)]phenyl glycidyl ether

The compound of Example 15(c) (5.0 g, 15.3 mmol), $K_2CO_3$ (6.4 g, 46.0 mmol), and (2R)-(–)-glycidyl 3-nitrobenzenesulfonate (5.6 g, 15.3 mmol) were heated in acetone (250 mL) to reflux 18 h. The solvent was concentrated in vacuo to half volume, poured into $H_2O$, extracted with EtOAc, the combined organic extracts were dried over $MgSO_4$, evaporated and purified by column chromatography (silica gel, 40% EtOAc/Hexanes) to give the title compound as a clear oil (4.9 g, 84%). $^1H$ NMR (400 MHz, CDCl$_3$) d 8.04 (d, J=8 Hz, 1H), 6.94 (d, J=8 Hz, 1H), 4.45 (dd, J=1,9 Hz, 1H), 4.11 (dd, J=7,11 Hz, 1H), 3.44 (m, 1H), 3.24 (t, J=9,18 Hz, 4H), 2.97 (m, 1H), 2.87(m, 1H), 1.52 (m, 4H), 0.84 (t, J=6,14 Hz, 6H).

e) N-[3-(2,3-dichloro-4-dipropylsulfamoyl)phenoxy-2(R)-hydroxypropyl]-N-[2-(4-methoxyphenyl)-1,1-dimethyl]ethylamine hydrochlonde salt The compound from Example 15(d) (1.6 g, 4.2 mmol), 1,1-dimethyl-2-(4-methoxyphenyl)ethylamine (0.75 g, 4.2 mmol) and LiClO$_4$ (0.89 g, 8.4 mmol) were dissolved in CH$_3$CN (150 mL) and refluxed 18 h. The mixture was concentrated in vacuo and purified by column chromatography (silica gel, 8% MeOH/CH$_2$Cl$_2$) to yield the title compound as a white solid (1.0 g, 44%). This was converted to the HCl salt by adding 1.7 mL of 1M HCl in MeOH, stirring 5 min, concentrating in vacuo, azeotroping with toluene then CH$_2$Cl$_2$. MS (ES) m/e 561.1 [M+H]$^+$; $^1H$ NMR (400 MHz, CDCl$_3$) d 9.94 (bs, 1H), 8.02 (d, J=8 Hz, 1H), 7.14 (d, J=8 Hz, 2H), 6.96 (d, J=8 Hz, 1H), 6.86 (d, J=7 Hz, 1H), 4.78 (m, 1H), 4.30 (m, 1H), 4.20 (m, 1H), 3.80 (s, 3H), 3.68 (m, 2H), 3.43 (bs, 1H), 3.23 (t, J=7,14 Hz, 4H), 3.12 (m, 2H), 1.50 (q, J=5,13 Hz, 4H), 1.43 (s, 3H), 1.38 (s, 3H), 0.83 (t, J=8,13, 6H).

Example 16
N-[3-(2,3-dichloro-4-dipropylsulfamoyl)phenoxy-2(R)-hydroxypropyl]-2-(2,3-dichlorophenyl)-1,1-dimethylethylamine hydrochloride Following the procedure of Example 15, except substituting 1,1-dimethyl-2-(2,3-dichlorophenyl)ethylamine for 1,1-dimethyl-2-(4-methoxyphenyl)ethylamine, the title compound was prepared (33 mg). MS (ES) m/e 599.1 [M+H]$^+$; $^1H$ NMR (400 MHz, CDCl$_3$)d 8.01(d, J=10 Hz, 1H), 7.36(m, 2H), 7.06(d, J=9 Hz, 1H), 6.94(d, J=10 Hz, 1H), 4.60(bm, 1H), 4.18(m, 2H), 3.34(d, J=11 Hz, 1H), 3.23(t, J=7 Hz, 4H), 3.18(d, J=12 Hz, 1H), 3.08(s, 2H), 1.53(q, J=6,13 Hz, 4H), 1.34(2 x s, 6H), 0.84(t, J=10 Hz, 6H).

Example 17

N-[3-(3-chloro-2-cyano-4-dimethylsulfamoyl)phenoxy-2(R)-hydroxyporopyl]-2-(4-methoxyphenyl)-1,1-dimethylethylamine hydrochloride a) 2-Chloro-6-methoxybenzonitrile 2-Chloro-6-fluorobenzonitrile (Aldrich, 5.0 g, 32.1 mmol) was dissolved in MeOH (100 mL), NaOMe (7.4 mL of 25% wt. solution, 32.1 mmol) and refluxed 18 h. The mixture was concentrated poured into EtOAc/H$_2$O and extracted with EtOAc to give the title compound (5.3 g, 59%).

b) (2-chloro-3-cyano-4-methoxy)phenylsulfonylchloride

Following the procedure from example 15(a) except substituting compound example 17(a) for 2,3-dichloroanisole, the title compound was prepared.

c) N-[2(R)-hydroxy-3-(3-chloro-2-cyanophenoxy-4-dimethylsulfonamidyl)propyl]-N-[2-(4-methoxyphenyl)-1,1-dimethylethyl]amine hydrochloride Following the procedure of Example 15(b)–15(e), except substituting dimethylamine for dipropylamine, and substituting compound of example 17 (b) for Example 15(a) the title compound was prepared (21 mg) MS (ES) m/e 496.2 [M+H]$^+$; $^1$H NMR (400 MHz, CDCl$_3$) d 8.22(d, J=10 Hz, 1H), 7.11(m, 3H), 6.82(d, 2H), 4.28(m, 2H), 4.20(m, 1H), 3.80(s, 3H), 3.12(dd, J=2,12 Hz, 1H), 2.98(dd, J=10, 12 Hz, 1H), 2.88(s, 6H), 2.78(s, 2H), 1.18(s, 6H).

Example 18

N-[3-(2,3-dichloro-4-morpholinosulfamoyl)phenoxy-2R)-hydroxypropyl]-2-(4-methoxyphenyl)-1,1-dimethylethylamine Following the procedure of Example 15, except substituting morpholine for dipropylamine, the title compound was prepared (5mg). $^1$H NMR (400 MHz, CDCl$_3$) d 8.04(d, J=8 Hz, 1H), 7.14(d, J=9 Hz, 2H), 7.00(d, J=9 Hz, 1H), 6.87(d, J=8 Hz, 2H), 4.76(m, 1H), 4.28(m, 2H), 3.82(s, 3H), 3.71(m, 5H), 3.49(m, 1H), 3.24(m, 4H), 3.11(m, 2H), 1.52(s, 3H), 1.43(s, 3H).

Example 19

N-[3-(3-chloro-2-cyano-4-morpholinosulfamoyl)phenoxy-2(R)-hydroxypropyl]-2-(4-methoxyyhenyl)-1,1-dimethylethylamine hydrochloride The title compound (70 mg) was prepared by the method of Example 17(c) substituting the method of I. T. Harrison Chem. Comm. 1969 p. 616 for procedure from example I(c) and substituting morpholine for dimethylamine. MS (ES) m/e 538.2[M+H]$^+$; $^1$H NMR (400 MHz, CDCl$_3$) d 8.20(d, J=9 Hz, 1H), 7.12(m, 3H), 6.81(d, J=9 Hz, 1H), 4.20–4.31 (m, 3H), 3.80(s, 3H), 3.72(m, 4H), 3.28(m, 4H), 3.13(d, J=10 Hz, 1H), 3.00(m, 1H), 2.80(s, 2H), 1.18(s, 6H).

Example 20

N-[3-(3-chloro-2-cyano-4-pyrrolidinosulfamoyl)phenoxy-2(R)-hydroxypropyl[2-(4-methoxyphenyl)-1,1-dimethylethylamine hydrochloride;

The title compound (105 mg) was prepared by the method of Example 19 substituting pyrrolidine for morpholine. MS (ES) m/e 522.1[M+H]$^+$; $^1$H NMR (400 MHz, CDCl$_3$) d 8.23(d, J=9 Hz, 1H), 7.11(d, J=9 Hz, 2H), 7.07(d, J=9 Hz, 1H), 6.83(d, J=9 Hz, 2H), 4.27(d, J=4 Hz, 2H), 4.18(m, 1H), 3.80(s, 3H), 3.40(m, 4H), 3.10(dd, J=2.10 Hz, 1H), 2.94(dd, J=8,12 Hz, 1H), 2.75(s, 2H), 1.95(m, 4H), 1.16(s, 6H).

Example 21

N-[3-(3-chloro-2-cyano-4-pyrrolidinosulfamoyl)phenoxy-2(R)-hydroxypropyl]-2-(4-fluorophenyl)-1,1-dimethylethylamine hydrochloride:

The title compound (35 mg) was prepared by the method of Example 20 substituting, 1,1-dimethyl-2-(4-fluorophenyl)ethylamine for), 1,1-dimethyl-2-(4-methoxyphenyl)ethylamine. MS (ES) m/e 510.1[M+H]$^+$; $^1$H NMR (400 MHz, CDCl$_3$) d 8.20(d, J=11 Hz, 1H), 1.10–7.30 (m, 3H), 6.99(m, 2H), 4.89(m, 1H), 4.03(dd, J=2,10 Hz, 1H), 3.95(dd, J=4,12 Hz, 1H), 3.39(m, 5H), 3.24(dd, J=3,10 Hz, 1H), 1.96(m, 4H), 1.23(s, 6H).

Example 22

N-[3-(3-chloro-2-cyano-4-pyrrolidinosulfamoyl)phenoxy-2(R)-hydroxypropyl]-2-(2-napthyl)-1,1-dimethylethylamine hydrochloride;

The title compound (130 mg) was prepared by the method of Example 20 substituting, 1,1-dimethyl-2-(2-napthylethylamine for), 1,1-dimethyl-2-(4-methoxyphenyl) ethylamine. MS (ES) m/e 542.2[M+H]$^+$; $^1$H NMR (400 MHz, CDCl$_3$) d 8.23(d, J=10 Hz, 1H), 7.80(m, 3H), 7.67(s, 1H), 7.45(m, 2H), 7.35(d, 1H), 3.38(m, 4H), 3.19(d, J=12 Hz, 1H), 3.06(m, 1H), 3.04(s, 2H), 1.95(m, 4H), 1.37(s, 6H).

Example 23

N-[3-(3-chloro-2-cyano-4-morpholinosulfamoyl)phenoxy-2(R)-hydroxypropyl]-2-(4-fluorophenyl)-dimethylethylamine hydrochloride The title compound (130 mg) was prepared by the method of Example 19 substituting 1,1-dimethyl-2-(4-fluorophenyl) ethylamine) for 1,1-dimethyl-2-(4-methoxyphenyl) ethylamine. MS (ES) m/e 526.2[M+H]$^+$; $^1$H NMR (400 MHz, CDCl$_3$) d 8.20(d, J=9 Hz, 1H), 7.22(m, 2H), 7.13(d, J=9 HZ, 1H), 7.01(d, J=9 Hz), 4.82(d, J=7 Hz, 1H), 4.68(m, 1H), 4.39(m, 2H), 3.73(m, 4H), 3.55–3.36(m, 2H), 3.27(m, 4H), 3.12(dd, J=12,22 Hz, 2H), 1.45(2xs, 6H).

Example 24

N-[3-(3-chloro-2-cyano-4-morpholinosulfamoyl)phenoxy-2(R)-hydroxypropyl]-2-(2-naphthyl)-1,1-dimethylethylamine hydrochloride The title compound (100 mg) was prepared by the method of Example 19 substituting, 1,1-dimethyl-2-(2-napthylethylamine) for 1,1-dimethyl -2-(4-methoxyphenyl) ethylamine. MS (ES) m/e 558.2[M+H]$^+$; $^1$H NMR (400 MHz, CDCl$_3$) d 8.17(d, J=9 Hz, 1H), 7.78(m, 3H), 7.65(s, 1H), 7.45(m, 2H), 7.33(d, J=10 Hz, 1H), 7.03(d, J=9 Hz, 1H), 4.26(d, J=3 Hz, 2H), 4.20(m, 1H), 3.75(m, 4H), 3.26(m, 4H), 3.17(dd, J=2,12 Hz, 1H), 3.01(m, 3H), 1.23(s, 6H).

Example 25

N-[3-(3-chloro-2-cyano-4-morpholinosulfamoyl)phenoxy-2(R)-hydroxypropyl]-2-(2-naphthyl)-1,1-dimethylethylamine hydrochloride The title compound (30 mg) was prepared by the method of Example 24 substituting thiomorpholine for morpholine MS (ES) m/e 574.2[M+H]$^+$; $^1$H NMR (400 MHz, CDCl$_3$) d 8.17(d, J=9 Hz, 1H), 7.77(m, 3H), 7.66(s, 1H), 7.43(m, 2H), 7.32(d, J=9 Hz, 1H), 7.02(d, J=9 Hz, 1H), 4.23 (m, 3H), 3.54(m, 4H), 3.13(d, J=12 Hz, 1H), 3.02(m, 3H), 2.68(m, 4H), 1.26(s, 6H).

Example 26

N-[3-(3-chloro-2-cyano-4-thiomorpholinosulfamoyl) phenoxy-2(R)-hydroxypropyl]-2-(4-methoxyphenyl)-1,1-dimethylethylamine hydrochloride The title compound (30 mg) was prepared by the method of Example 19 substituting thiomorpholine for morpholine. MS (ES) m/e 554.3[M+H]$^+$; $^1$H NMR (400 MHz, CDCl$_3$) d 8.13(d, J=10 Hz, 1H), 7.02(d, J=9 Hz, 2H), 6.98(d, J=10 Hz, 1H), 6.76(d, J=9 Hz, 2H), 4.17(d, J=4 Hz, 2H), 4.02(m, 1H), 3.73(s, 3H), 3.52(m, 2H), 2.97(dd, J=2,10 Hz, 1H), 2.82(dd, J=8,11 Hz, 1H), 2.64(m, 6H), 1.06(s, 6H).

Example 27
N-[3-[3-chloro-2-cyano-4-(2'-cyanoeth-1-yl)-cyclopropylsulfamoyl]phenoxy-2(R)-hydroxypropyl]-2-(4-methoxyuhenyl)-1,1-dimethylethylamine hydrochloride The title compound (70 mg) was prepared by the method of Example 19 substituting 3-(cyclopropylamino)propionitrile (Transworld Chemicals) for morpholine. MS (ES) m/e 561.3[M+H]⁺; ¹H NMR (400 MHz, CDCl₃) d 8.20(d, J=Hz, 1H), 7.01(d, J=8 Hz, 3H), 6.74(d, J=9 Hz, 1H), 4.18(m, 2H), 3.96(m, 1H), 3.69(m, 5H), 2.94(dd, J=3,11 Hz, 1H,) 2.78(d, 1H), 2.73(t, J=7,12 Hz, 2H), 2.49(m, 1H), 1.04(s, 6H), 0.62(m, 2H), 0.53(m, 2H).

Example 28
N-[3-[3-chloro-2-cyano-4-(2'-cyanoeth-1-yl)-cyclopropylsulfamoyl]phenoxy-2(R)-hydroxypropyl]-2-(2-napthyl)-1,1-dimethylethylamine hydrochloride The title compound (85 mg) was prepared by the method of Example 27 substituting 1,1-dimethyl-2-(2-napthylethylamine) for 1,1-dimethyl-2-(4-methoxyphenyl)ethylamine. MS (ES) m/e 581.3[M+H]⁺; ¹H NMR (400 MHz, CDCl₃) d 8.17(d, J=10 Hz, 1H), 7.71(m, 1H), 7.67(d, J=9 Hz, 2H), 7.53(s, 1H), 7.38(m, 2H), 7.26(d, J=8 Hz, 1H), 6.94(d, J=9 Hz, 1H), 4.15(m, 2H), 3.96(m, 1H), 3.69(t, J=8,14 Hz, 2H), 2.98(dd, J=2,12 Hz, 1H), 2.82(m, 3H), 2.74(t, J=2,12 Hz, 2H), 2.49(m, 1H), 1.08(s, 6H), 0.59(m, 2H), 0.40(m, 2H).

Example 29
N-[3-[3-chloro-2-cyano-4-(benzyl-cyclopropyl)sulfamoyl]phenoxy-2(R)-hydroxypropyl]-2-(2-napthyl)-1,1-dimethylethylamine hydrochloride:

a) N-cyclopropyl(2-chloro-3-cyano-4-methoxyphenyl)sulfonamide

The title compound was prepared utilizing the compound of Example 17(b) by the method of Example 15(b) substituting cyclopropylamine (Aldrich) for dipropylamine.

b) N-cyclopropyl-N-benzyl(2-chloro-3-cyano-4-methoxyphenyl)sulfonamide

The compound of Example 29(a) (1.3 g, 5.0 mmol), K₂CO₃(0.69 g, 5.0 mmol) and benzyl bromide (0.60 mL, 5.0 mmol) in acetone (40 mL) were refluxed 18 h. The solution was concentrated and poured into EtOAc/H₂O and extracted with EtOAc, dried and concentrated to dryness in vacuo to yield the title compound (1.8 g, 96%). ¹H NMR (400 MHz, CDCl₃) d 8.25(d, J=10 Hz, 1H), 7.39–7.20(m, 5H), 6.92(d, J=10 Hz, 1H), 4.58(s, 2H), 3.96(s, 3H), 2.26(m, 1H), 0.46 (m, 2H), 0.36(m, 2H).

c) N-2(R)-hydroxy-3-[3-chloro-2-cyano-4-[(N-propionitrile-N-cyclopropyl)sulfamidyl]phenoxypropyl]-N-[2-(2-napthylphenyl)-1,1-dimethylethyllamine hydrochloride The title compound (25 mg) was prepared by the method of Example 24 substituting the compound of Example 29(b) for. N-morpholino(2chloro-3-cyano-4-methoxyphenyl)sulfonamide. MS (ES) m/e 618.3[M+H]⁺; ¹H NMR (400 MHz, CDCl₃) d 8.16(d, J=10 Hz, 1H), 7.70(m, 3H), 7.57(s, 1H), 7.36(m, 4H), 7.25(m, 4H), 6.88(d, J=9 Hz, 1H), 4.54(s, 2H), 4.14(d, J=3 Hz, 2H), 4.01(m, 1H), 3.02(dd, J=2,11 Hz, 1H), 2.87(m, 3H), 2.22(m, 1H), 2.11 (m, 6H), 0.46(m, 2H), 0.33(m, 2H).

Example 30
N-[3-[3-chloro-2-cyano-4-(benzyl-cyclopropyl)sulfamoyl]phenoxy-2(R)-hydroxypropyl]-2-(4-methoxyphenyl)-1,1-dimethylethylamine hydrochloride;

The title compound (105 mg) was prepared by the method of Example 29 substituting 1,1-dimethyl-2-(4-methoxyphenyl)ethylamine for 1,1-dimethyl-2-(2-napthylethylamine). MS (ES) m/e 598.3[M+H]⁺; ¹H NMR (400 MHz, CDCl₃) d 8.18(d, J=9 Hz, 1H), 7.36–7.13(m, 5H), 7.01(d, J=9 Hz, 2H), 6.95(d, J=10 Hz, 1H), 6.72(d, J=9 Hz, 2H), 4.56(s, 2H), 4.15(m, 2H), 4.01(m, 1H), 3.70(s, 3H), 2.98 (m, 1H), 2.84(d, J=9,12 Hz, 1H), 2.62(s, 2H), 2.22(m, 1H) 1.04(s, 6H), 0.44(m, 2H), 0.35(m, 2H).

Example 31
N[3-[3-chloro-2-cyano-4-(4'-N-t-butoxycarbonylpiperazino)sulfamoyl]phenoxy)-2(R)-hydroxypropyl-2-(4-methoxyphenyl)-1,1-dimethylethylamine hydrochloride The title compound (20 mg) was prepared by the method of Example 19 substituting t-butyl-1-piperazinecarboxylate (Aldrich) for morpholine. MS (ES) m/e 637.4[M+H]⁺; ¹H NMR (400 MHz, CDCl₃) d 8.15(d, J=9 Hz, 1H), 7.05(m, 4H), 6.77(m, 3H), 4.21(m, 3H), 3.73(s, 3H), 3.46(m, 4H), 3.27(m, 4H), 3.07(m, 1H), 2.92(m, 1H), 2.72(s, 2H), 1.41(s, 9H), 1.12(s, 6H).

Example 32
N-[3-(2,3-dichloro-4-dipropylsulfamoyl)phenoxy-2(R)-hydroxypropyl]-2-(2-naphthyl)-1,1-dimethylethylamine hydrochloride Following the procedure of Example 15, substituting 1,1-dimethyl-2-(2-naphthyl)ethylamine for 1,1-dimethyl-2-(4-methoxyphenyl)ethylamine in 15(e), the title compound was prepared (157 mg). MS (ES) m/e 581.2 [M+H]⁺; ¹H NMR (400 MHz, CDCl₃) d10.00 (m, 1H), 8.24 (m, 1H), 7.98 (d, J=10.5 Hz, 1H), 7.81 (m, 3H), 7.73 (s, 1H), 7.48 (m, 2H), 7.34 (d, J=8 Hz, 1H), 6.87 (d, J=10.5 Hz, 1H), 4.80 (m, 1H), 4.28–4.12 (m, 2H), 3.55–3.30 (m, 2H), 3.37 (s, 2H), 3.23 (t, J=8 Hz, 4H), 1.53 (m, 10 H), 0.83 (t, J=8 Hz, 6H).

Example 33
N-[3-(2,3-dichloro-4-propylsulfamoyl)phenoxy-2(R)-hydroxypropyl]-2-(4-methoxyphenyl)-1,1-dimethylethylamine hydrochloride Following the procedure of Example 15, substituting propylamine for dipropylamine in 1(b), the title compound was prepared (211 mg). MS (ES) m/e 519.1 [M+H]⁺;. ¹H NMR (400 MHz, DMSO) d 9.00 (m, 1H), 8.69 (m, 1H), 7.95 (d, J=9 Hz, 1H), 7.92 (m, 1H), 7.37 (d, J=9 Hz, 1H), 7.15 (d, J=9 Hz, 2H), 6.91 (d, J=9 Hz, 2H), 6.04 (m, 1H), 4.38–4.23 (m, 3H), 3.74 (s, 3H), 3.39–3.28 (m, 1H), 3.19–3.06 (m, 1H), 2.95 (s, 2H), 1.42–1.31 (m, 2H), 1.22 (s, 6H).

Example 34
N-[3-(2,3-dichloro-4-sulfamoyl)phenoxy-2R)-hydroxypropyl]-2-(4-methoxyphenyl)-1,1-dimethylethylamine hydrochloride Following the procedure of Example 15, substituting ammonia (2M in methanol) for dipropylamine in 15(b), the title compound was prepared (14 mg). Purification by preparative HPLC [PRP-1, 215×250 mm, 30% CH₃CN/H₂O containing 0.1% TFA]. MS (ES) m/e 477.0 [M+H]⁺; ¹H NMR (360 MHz, CDCl₃) d7.98 (d, J=9.5 Hz, 1H), 7.10 (d, J=12 Hz, 2H), 6.93 (d, J=11 Hz, 1H), 6.85 (d, J=9.5 Hz, 2H), 4.55 (m, 1H), 4.29–4.21 (m, 1H), 4.15–4.08 (m,1H), 3.78 (s, 3H), 3.43–3.33 (m, 1H), 3.19–3.09 (m, 1H), 2.98 (dd, J=13, 39 Hz, 2H), 1.44 (s, 3H), 1.35 (s, 3H).

Example 35
N-[3-(2,3-dichloro-4-methylsulfamoyl)phenoxy-2(R)-hydroxypropyl]-2-(4-methoxyphenyl)-1,1-dimethylethylamine hydrochloride Following the procedure of Example 15, substituting methylamine (2M in methanol) for dipropylamine in 15(b), the title compound was prepared (123 mg). MS (ES) m/e 491.1 [M+H]+;. $^1$H NMR (400 MHz, DMSO) d 7.94 (d, J=9 Hz, 1H), 7.75 (m, 1H), 7.39 (d, J=9 Hz, 1H), 7.14 (d, J=9 Hz, 2H), 6.89 (d, J=9 Hz, 2H), 4.36–4.19 (m, 3H), 3.74 (s, 3H), 3.33–3.23 (m, 1H), 3.15–3.03 (m, 1H), 2.92 (s, 2H), 2.45 (d, J=6 Hz, 3H), 1.20 (s, 6H).

Example 36
N-[3-(2,3-dichloro-4-pyrrolidinosulfamoyl)phenoxy-2(R)-hydroxypropyl]2-(4-methoxyphenyl)-1,1-dimethylethylamine hydrochloride Following the procedure of Example 15, substituting pyrrolidine for dipropylamine in 15(b), the title compound was prepared (255 mg). MS (ES) m/e 531.2 [M+H]+; $^1$H NMR (400 MHz, DMSO) d 9.05 (m, 1H), 8.72 (m, 1H), 7.97 (d, J=10.5 Hz, 1H), 7.39 (d, J=10.5 Hz, 1H), 7.15 (d, J=9 Hz, 2H), 6.90 (d, J=9 Hz, 2H), 6.08–6.00 (m, 1H), 4.39–4.23 (m, 3.73 (s, 3H), 3.32–3.21 (m, 5H), 3.19–3.06 (m, 1H), 2.95 (s, 2H), 1.85 (m, 4H), 1.22 (s, 6H).

Example 37
N-[3-(2,3-dichloro-4-piperidinosulfamoyl)phenoxy-2(R)-hydroxypropyl]-2-(4-methoxyphenyl)-1,1-dimethylethylamine hydrochloride Following the procedure of Example 15, substituting piperidine for dipropylamine in 15(b), the title compound was prepared (800 mg). MS (ES) m/e 545.3 [M+H]+; $^1$H NMR (400 MHz, DMSO) d 9.05 (m, 1H), 8.74 (m, 1H), 7.97 (d, J=9 Hz, 1H), 7.40 (d, J=9 Hz, 1H), 7.16 (d, J=9 Hz, 2H), 6.91 (d, J=9 Hz, 2H), 6.09–6.00 (m, 1H), 4.40–4.22 (m, 3H), 3.75 (s, 3H), 3.40–3.27 (m, 1H), 3.22–3.06 (m, 5H), 2.96 (s, 2H), 1.59–1.42 (m, 6H), 1.23 (s, 6H).

Example 38
N-[3-(2,3-dichloro-4-cyclopropylsulfamoyl)phenoxy-2(R)-hydroxypropyl]-2-(4-methoxyphenyl)-1,1-dimethylethylamine hydrochloride Following the procedure of Example 15, substituting cyclopropylamine for dipropylamine in 15(b) and following the deprotection procedure referenced in Example 5 in place of the procedure of 15(c), the title compound was prepared (138 mg). MS (ES) m/e 517.1 [M+H]+; $^1$H NMR (400 MHz, DMSO) d 9.11–8.90 (bs, 1H), 8.82–8.59 (bs, 1H), 8.29 (m, 1H), 8.01 (d, J=9 Hz, 1H), 7.41 (d, J=9 Hz, 1H), 7.16 (d, J=9 Hz, 2H), 6.90 (d, J=9 Hz, 2H), 6.11–5.94 (bs, 1H), 4.39–4.22 (m, 3H), 3.74 (s, 3H), 3.37–3.24 (m, 1H), 3.16–3.04 (m, 1H), 2.93 (s, 2H), 2.18 (m, 1H), 1.21 (s, 6H), 0.50–0.36 (m, 4H).

Example 39
N-[3-[3-chloro-2-cyano-4-(4'-N-t-butoxycarbonylpiperazino)sulfamoyl]phenoxy)-2(R)-hydroxypropyl]-2-(2-naphthyl)-1,1-dimethylethylamine hydrochloride;

The title compound (10 mg,) was prepared by the method of example 31 substituting 1,1-dimethyl-2-(2-napthyl) ethylamine for 1,1-dimethyl-2-(4-methoxyphenyl) ethylamine. MS (ES) m/e 657.4[M+H]+; $^1$H NMR (400 MHz, CDCl$_3$) d 8.09(d, J=9 Hz, 1H), 7.77(m, 1H), 7.74(m, 2H), 7.59(s, 1H), 7.39(m, 2H), 7.25(d, J=8 Hz, 1H), 6.92(d, J=9 Hz, 1H), 4.16(d, J=4 Hz, 2H), 4.00(m, 1H), 3.42(m, 4H), 3.18(m, 4H), 3.09(dd, J=2,10 Hz, 1H), 2.87(s, 2H), 2.87(m, 1H), 1.40(s, 9H), 1.10(2s, 6H).

Example 40
Preparation of (R)-3-[2-cyano-4-[N-benzyl-N'-morpholino] ureido]phenoxy]-1-[1,1-dimethyl-2-(2-naghthyl) ethylamino]-propan-2-ol.

a) 2-Methoxyl-5-N-[[4-morpholino]carbonyl]amino benzonitrile

To a stirred mixture of 2-methoxyl-5-aminobenzonitrile (2 g, 12.34 mmol), and pyridine (1.28 g, 16.2 mmol) in dried CH$_2$Cl$_2$ (20 mL) was added 4-morpholinecarbonyl chloride (2.42 g, 16.2 mmol). After stirring at RT for 24 h, the mixture was diluted with CH$_2$Cl$_2$ and washed with H$_2$O, brine, dried over MgSO$_4$, concentrated to give an orange solid (3.04 g, 86%) $^1$H NMR: (400 MHz, DMSO-d$_6$): d 3.23 (t, J=4.9 Hz, 4H), 3.47 (t, J=4.9 Hz, 4H), 3.9 (s, 3H), 6.89 (d, J=9 Hz, 1H), 7.3 (d, J=9 Hz, 1H), 8.01 (s, 1H).

b) 2-Methoxyl-5-[N-methyl-N-[[4-morpholino]carbonyl] amino] benzonitrile.

To a stirred suspension of NaH (60%, pre-washed with hexane, 0.2 g, 4.98 mmol) in dry DMF (10 mL) was added example 14a (1 g, 3.8 mmol). After stirrineg at RT in 1 h, methyl iodide (1.62 g, 11.5 mmol) was added and stirred overnight, taken up in H$_2$O, extracted with EtOAc. The organic extracts were washed with brine, dried over MgSO$_4$, concentrated to give a brown oil (1.0 g, 98%). $^1$H NMR: (400 MHz, DMSO-d$_6$): d 2.95 (s, 3H), 3.23 (t, J=4.9 Hz, 4H), 3.47 (t, J=4.9 Hz, 4H), 3.9 (s, 3H), 6.89 (d, J=9 Hz, 1H), 7.3 (d, J=9 Hz, 1H), 8.01 (s, 1H).

c) 2-Hydroxy-5-[N-methyl-N-[[4-morpholino]carbonyl] amino]benzonitrile.

Following the example 1e, the title compound was prepared as a yellow oil (0.33 g, 40%). $^1$H NMR: (400 MHz, DMSO-d$_6$): d 2.95 (s, 3H), 3.23 (t, J=4.9 Hz, 4H), 3.47 (t, J=4.9 Hz, 4H), 6.89 (d, J=9 Hz, 1H), 7.3 (d, J=9 Hz, 1H), 8.01 (s, 1H).

d) 2-Cyano-5-[N-methyl-N-[[4-morpholino]carbonyl] amino]phenyl glycidol.

Following the example 1f, the title compound was prepared as a brown oil (0.23 g, 60%). $^1$H NMR (400 MHz, DMSO-d$_6$): d 2.85 (t, J=4.5 Hz, 1H), 2.95 (s, 3H), 2.97 (t, J=4.5 Hz, 1H), 3.23 (t, J=4.9 Hz, 4H), 3.42 (m,1H), 3.47 (t, J=4.9 Hz, 4H), 4.12 (dd, J=5.4, 11.4 Hz, 1H), 4.42 (dd, J=5.4, 11.4 Hz, 1H), 6.89 (d, J=9 Hz, 1H), 7.3 (d, J=9 Hz, 1H), 8.01 (s, 1H).

e) Synthesis of (R)-3-[2-cyano-4-[N-benzyl-N'-morpholino]ureido]phenoxy]-1-[1,1-dimethyl-2-(2-naphthyl)ethylamino]-propan-2-ol.

Following the procedure in example 7, the title compound was prepared as an off white foam (0.6 g, 56%) $^1$H NMR (400 MHz, DMSO-d$_6$): d 1.09 (s, 3H), 1.11 (s, 3H), 2.85 (t, J=4.5 Hz, 1H), 2.95 (s, 3H), 2.97 (t, J=4.5 Hz, 1H), 3.23 (t, J=4.9 Hz, 4H), 3.42 (m, 1H), 3.47 (t, J=4.9 Hz, 4H), 4.12 (dd, J=5.4, 11.4 Hz, 1H), 4.42 (dd, J=5.4, 11.4 Hz, 1H), 7.12 (d, J=7.2 Hz, 1H), 7.27 (m, 5H), 7.35 d, J=7.2 Hz, 1H), 7.55 (s, 1H), 7.67 (s, 1H), 7.76 (d, J=7.2 Hz, 1H). MS (m+1, m/z): 417.6. Anal. Calcd. for C$_{30}$H$_{36}$N$_4$O$_4$ 1.5H$_2$O: C, 66.28; H, 7.23; N, 10.3; Found: C, 66.61; H, 6.96; N, 9.92.

Example 40
Preparation of N-[2R-Hydroxy-3-[2-cyano-4-[N-benzyl-N-[(4-morpholino)carbonyl]amino]phenoxy]propyl]1,1-dimethyl-2-[2-napthyl]ethylamine a) 2-Methoxyl-5-[N-benzyl-N-[[4-morpholino]carbonyl] amino] benzonitrile Following the procedure in example 14b, the title compound was prepared as a tan solid (1.2 g, 81%): $^1$H NMR: (400 MHz, DMSO-d$_6$): d 3.23 (t, J=4.9 Hz, 4H), 3.47 (t, J=4.9 Hz, 4H), 3.9 (s, 3H), 4.8 (s, 2H), 6.89 (d, J=9 Hz, 1H), 7.28 (m, 5H), 7.43 (d, J=9 Hz, 1H), 8.01 (s, 1H).

b) 2-Hydroxy-5-[N-benzyl-N-[[4-morpholino]carbonyl] amino]benzonitrile

Following the example in example 14c, the title compound was prepared as a light yellow foam (0.64 g, 74%).

¹H NMR: (400 MHz, DMSO-d₆): d 3.23 (t, J=4.9 Hz, 4H), 3.47 (t, J=4.9 Hz, 4H), 4.8 (s, 2H), 6.89 (d, J=9 Hz, 1H), 7.28 (m, 5H), 7.43 (d, J=9 Hz, 8.01 (s, 1H).

c) 2-Cyano-5-[N-benzyl-N-[[4-morpholino]carbonyl]amino]phenyl glycidol

Following the procedure in example 1f, the title compound was prepared as an off white foam 0.71 g, 95%). ¹H NMR: (400 MHz, DMSO-d₆): d 2.75 (t, J=4.5 Hz, 1H), 2.85 (t, J=4.5 Hz, 1H), 3.23 (t, J=4.9 Hz, 4H), 3.47 (t, J=4.9 Hz, 4H), 4.71 (s, 2H), 6.89 (d, J=9 Hz, 1H), 7.28 (m, 5H), 7.43 (d, J=9 Hz, 1H), 8.01 (s, 1H).

d) Synthesis of (R)-3-[2-cyano-4-[N-benzyl-N'-morpholino]ureido]phenoxy]-1-[1,1-dimethyl-2-(2-naphthyl)ethylamino]-propan-2-ol.

Following the procedure in example 7, the title compound was prepared as yellow solid (0.6 g, 56%). ¹H NMR (400 MHz, DMSO-d₆): d 1.09 (s, 3H), 1.11 (s, 3H), 2.80 (m, 4H), 3.15 (t, J=4.9 Hz, 4H), 3.47 (t, J=4.9 Hz, 4H), 3.85 (m, 1H), 4.12 (m, 2H), 4.71 (s, 2H), 5.1 (m, 1H), 7.12 (d, J=7.2 Hz, 1H), 7.27 (m, 6H), 7.35 (d, J=7.2 Hz, 1H), 7.47 (m, 2H), 7.55 (s, 1H), 7.67 (s, 1H), 7.76 (d, J=7.2 Hz, 1H), 7.79 (m, 2H). MS (m+1, m/z): 593.7. Anal. Calcd. for $C_{36}H_{40}N_4O_4 \cdot H_2O$: C, 70.68; H, 7.08; N, 9.15; Found: C, 70.9; H, 6.94; N, 8.84.

Example 41

Preparation of (R)-1-[1,1-dimethyl-2-(4-methoxyphenyl)ethylamino]-3-[10,11-dihydro-2-cyano-3-oxy-5H-dibenzo[a,d]cycloheptene-10-(R)-acetic acid]-propan-2-ol hydrochloride salt a) Ethyl 10,11-dihydro3-hydroxyl-5H-dibenzo[a,d]cycloheptene-10-(R)-acetate.

AlCl₃ (2.2 g, 17 mmol) was added to a cold solution of methyl-(10R)-(10,11-dihydro-3-methyloxy-5H-dibenzo[a,d]cycloheptene-10-acetate (1.0 g, 3.4 mmol) and ethylmercaptan (1.2 mL, 17 mmol) in CH₂Cl₂ (15 mL). After 2 h at 0° C., the solution was concentrated and residue treated with ice/water (50 mL) and CH₂Cl₂ (50 mL). The organic layer was separated and washed with water (2×) and concentrated to give 0.95 g (95%) of the title compound. ¹H NMR (400 MHz, DMSO-d₆) δ 1.1–1.3 (m, 3H), 2.4–2.8 (m, 3H), 3.0–3.8 (m, 4H), 4.0–4.2 (m, 3H), 6.5–7.2 (m, 7H), 9.1–9.2 (s, 1H).

b) Ethyl 10,11-dihydro3-hydroxyl-2-formyl-5H-dibenzo[a,d]cycloheptene-10-(R)-acetate.

A solution of ethyl 10,11-dihydro-3-hydroxyl-5H-dibenzo[a,d]cycloheptene-10-(R)-acetate (2.9 g, 9.8 mmol), SnCl₄ (0.15 mL, 1.3 mmol) and tributylamine (1.2 mL, 5.2 mmol) in toluene (60 mL) was stirred at RT for 20 min under an argon atmosphere. Paraformaldehyde (0.86 g) was added and the solution was heated at reflux for 18 h. The solution was cooled to RT and poured into water and acidified with aqueous HCl (3M) to pH 2 (litmus paper). Ethyl ether was added and the layers separated. The organic layer was washed with water and concentrated. Flash chromatography (silica gel, 50% EtOAc/Hexane) yielded 2.5 g (70%) of the title compound. ¹H NMR (400 MHz, DMSO-d₆) δ 1.1–1.3 (m, 3H), 2.5–3.2 (m, 4H), 3.6–4.2 (m, 5H), 6.5–7.4 (m, 6H), 10.1–10.2 (s, 1H), 10.5–10.6 (s, 1H).

c) Ethyl 10,11-dihydro-3-hydroxyl-2-iminohydroxyl-5H-dibenzo[a,d]cycloheptene10-(R)-acetate.

A solution of ethyl 10,11-dihydro-3-hydroxyl-2-formyl-5H-dibenzo[a,d]cycloheptene-10-(R)-acetate (1.2 g, 3.8 mmol), hydroxylamine hydrochloride (0.68 g, 9.8 mmol) and triethylamine (1.4 mL, 10 mmol) in EtOH (20 mL) was heated at reflux under an argon atmosphere. After 18 h the solution was concentrated to give 2.5 g of the crude title compound which was used in the next step without further purification.

d) Ethyl 10,11-dihydro-2-cyano-3-oxyacetyl-5H-dibenzo[a,d]cycloheptene-10-(R)-acetate.

A solution of ethyl 10,11-dihydro-3-hydroxyl-2-iminohydroxyl-5H-dibenzo[a,d]cycloheptene-10-(R)-acetate (2.5 g, 3.8 mmol) in acetic anhydride (30 mL) was heated at reflux for 30 min. The solution was then concentrated. Flash chromatography (silica gel, 30% EtOAc/Hexane) yielded 0.8 g (58%) of the title compound. ¹H NMR (400 MHz, DMSO-d₆) δ 1.1–1.3 (m, 3H), 2.2–3.1 (m, 6H), 3.2–4.4 (m, 6H), 7.0–7.2 (m, 4H), 7.3–7.4 (s, 1H), 7.6–7.7 (m, 1H).

e) Ethyl 10,11-dihydro-2-cyano-3-hydroxyl-5H-dibenzo[a,d]cycloheptene-10-(R)-acetate.

A solution of ethyl 10,11-dihydro-2-cyano-3-oxyacetyl-5H-dibenzo[a,d]cycloheptene-10-(R)-acetate (0.8 g, 2.2 mmol) in EtOH/water (1:1, 10 mL) was treated with K₂CO₃ (0.76 g, 5.5 mmol). After 3 h the solution was concentrated. The residue was partitioned between EtOAc/water and aqueous HCl (1M) was added to adjust the solution to pH 2 (litmus paper). The EtOAc layer was separated and washed with water (2×) and concentrated to give 0.65 g (92%) of the title compound. ¹H NMR (400 MHz, DMSO-d₆) δ 1.1–1.2 (m, 3H), 2.6–3.2 (m, 4H), 3.6–4.2 (m, 5H), 6.8–6.9 (s, 1H), 7.0–7.2 (m, 4H), 7.3–7.4 (s, 1H), 10.8–10.9 (s, 1H).

f) (2R)-Glycidyl-[ethyl 10,11-dihydro-2-cyano-3-oxy-5H-dibenzo[a,d] cycloheptene-10-(R)-acetate].

A solution of ethyl 10,11-dihydro-2-cyano-3-hydroxyl-5H-dibenzo[a,d]cycloheptene-10-(R)-acetate (0.67 g, 2.1 mmol), (2R)-gycidyl 3-nitrobenzenesulfonate (Aldrich Chemicals, 0.54 g, 2.1 mmol) and K₂CO₃ (0.864 g, 6.3 mmol) in acetone (20 mL) was heated at reflux for 18 hr. The solution was filtered and the filtrate was concentrated to give 0.8 g of the title compound which was used in the next step without further purification.

g) (R)-1-[1,1-dimethyl-2-(4-methoxyphenyl)ethylamino]-3-[ethyl-10,11-dihydro-2-cyano-3-oxy-5H-dibenzo[a,d]cycloheptene-10-(R)-acetate]-propan-2-ol hydrochloride salt A solution of (2R)-glycidyl-(ethyl-10,11-dihydro-2-cyano-3-oxy-5H-dibenzo[a,d]cycloheptene-10-(R)-acetate) (0.8 g, 2.1 mmol), 1,1-dimethyl-2-(4-methoxyphenyl)ethyl amine (0.375 g, 2.1 mmol) and LiClO₄ (0.445 g, 4.2 mmol) in CH₃CN (10 mL) was heated at reflux for 18 hr. After this time the solution was concentrated. Flash chromatography (silica gel, 5% CH₃OH/CH₂Cl₂) and treatment with HCl in MeOH yielded 0.7 g (60%) of the title compound. MS (ES) m/e 557.3 (M+H)⁺; ¹H NMR (DMSO-d₆) δ 1.0–1.3 (m, 9H), 2.5–3.2 (m, 8H), 3.4–4.3 (m, 11H), 5.9–6.0 (s, 1H), 6.8–7.2 (m, 8H), 7.2–7.3 (s, 1H), 7.4–7.5 (s, 1H), 8.4–8.5 (broad s, 2H).

h) (R)-1-[1,1-dimethyl-2-(4-methoxyphenyl)ethylamino]-3-[10,11-dihydro-2-cyano-3-oxy-5H-dibenzo[a,d]cycloheptene-10-(R)-acetic acid]-propan-2-ol hydrochloride salt.

A solution of (R)-1-[1,1-dimethyl-2-(4-methoxyphenyl)ethylamino]-3-[ethyl-10,11-dihydro-2-cyano-3-oxy-5H-dibenzo[a,d]cycloheptene-10-(R)-acetate]-propan-2-ol (0.6 g, 1.1 mmol) in EtOH/water (1:1, 4 mL) was treated with aqueous NaOH (1M, 2 mL, 2 mmol). After 18 h the solution was concentrated and water (10 mL) was added. Solution was cooled and acidified with aqueous HCl (1M) (pH 6, litmus paper). The solution was filtered and the solid precipitate was triturated with EtOAc. Filtration and drying in vacuo gave 0.25 g (45%) of the title compound. MS (ES) m/e 529.4 (M+H)⁺; ¹H NMR (400 MHz, DMSO-d₆) δ 1.1–1.2 (s, 6H), 2.5–3.2 (m, 5H), 3.3–3.4 (s, 3H), 4.0–4.3 (m, 4H), 6.8–7.2 (m, 8H), 7.2–7.3 (s, 1H), 7.4–7.5 (s, 1H).

Example 42
Preparation of (R)-1-[1,1-dimethyl-2-(4-methoxyphenyl) ethylamino]-3-[ethyl-10,11-dihydro-2-cyano-3-oxy-5H-dibenzo[a,d]cycloheptene-10-(R/S)-acetate]-propan-2-ol a) (2R)-Glycidyl-(ethyl-10,11-dihydro-3-oxy-5H-dibenzo[a,d]cycloheptene-10-(R/S)-acetate)

Following the procedure of Example 41 (f) except substituting ethyl-(R/S)-10,11-dihydro-3-hydroxyl-5H-dibenzo[a,d]cycloheptene-10-acetate for compound of Example 41(e), 0.7 g of the title compound was prepared and used without further purification in the next step.

b) (R)-1-[1,1-dimethyl-2-(4-methoxyphenyl) ethylamino]-3-[ethyl-10,11-dihydro-2-cyano-3-oxy-5H-dibenzo[a,d]cycloheptene-10-(R/S)-acetate]-propan-2-ol hydrochloride salt Following the procedure of Example 41(g) except substituting (2R)-glycidyl-(ethyl-10,11-dihydro-3-oxy-5H-dibenzo[a,d]cycloheptene-10-(R/S)-acetate)(0.7 g, 2.1 mmol) for compound of Example 41(f), 0.44 g (45%) of the title compound was prepared. MS (ES) m/e 532.4 (M+H)$^+$; $^1$H NMR (400 MHz, DMSO-d6) δ 1.1–1.2 (s, 9H), 2.5–3.2 (m, 9H), 3.5–4.2 (m, 11H), 6.7–7.2 (m, 11H).

Example 43
Preparation of (R)-1-[1,1-dimethyl-2-(4-methoxythenyl) ethylamino]-3-[10,11-dihydro-2-cyano-3-oxy-5H-dibenzo[a,d]cycloheptene-10-(R/S)-acetic acid]-propan-2-ol hydrochloride salt a) (R)-1-[1,1-dimethyl-2-(4-methoxyphenyl)ethylamino]-3-[10,11-dihydro-2-cyano-3-oxy-5H-dibenzo[a,d]cydoheptene-10-(R/S)-acetic acid]-propan-2-ol hydrochloride salt.

Following the procedure of Example 41 (h) except substituting (R)-1-[1,1-dimethyl-2-(4-methoxyphenyl) ethylamino]-3-[ethyl-10,11-dihydro-2-cyano-3-oxy-5H-dibenzo[a,d]cycloheptene-10-(R/S)-acetate]-propan-2-ol hydrochloride salt for compound of Example 41 (g), 0.118 g (55%) of the title compound was prepared. MS (ES) m/e 504.2 (M+H)$^+$; $^1$H NMR (400 MHz, DMSO-d$_6$) δ 1.1–1.2 (m, 6H), 2.4–4.3 (m, 20H), 6.7–7.2 (m, 11H).

Example 44
Preparation of (R)-1-[1,1-dimethyl-2-(4-methoxthenyl) ethylamino]-3-[ethyl-10,11-dihydro-2-cyano-3-oxy-5H-dibenzo[a,d]cycloheptene-10-(R)-acetate]-propan-2-ol hydrochloride salt.

a) (2R)-Glycidyl ethyl-10,11-dihydro-2-cyano-3-oxy-5H-dibenzo[a,d]cycloheptene-10-(R)-acetate Following the procedure of Example 41 (f) except substituting ethyl-10,11-dihydro-2-cyano-3-oxyl-5H-dibenzo[a,d]cycloheptene-10-(R)-acetate.(0.337 g, 1.1 mmol) for the compound of Example 41 (e), 0.37 g of the title compound was prepared and used as without further purification in the next step.

b) (R)-1-[1,1-dimethyl-2-(4-methoxyphenyl) ethylamino]-3-[ethyl-10,11-dihydro-2-cyano-3-oxy-5H-dibenzo[a,d]cycloheptene-10-(R)-acetate1-propan-2-ol hydrochloride salt.

Following the procedure of Example 41 (g) except substituting (2R)-glycidyl ethyl-10,11-dihydro-2-cyano-3-oxy-5H-dibenzo[a,d]cycloheptene-10-(R)-acetate (0.37 g, 1.1 mmol) for the compound of Example 41 (f), 0.125 g (22%) of the title compound was prepared. MS (ES) m/e 532.3 (M+H)$^+$; $^1$H NMR (400 MHz, DMSO-d$_6$) δ 1.1–1.3 (m, 9H), 2.5–4.3 (m, 20H), 5.7–5.9 (s, 1H), 6.7–7.2 (m, 11H), 8.2–8.4 (broad s, 2H).

Example 45
Preparation of (R)-1-[1,1-dimethyl-2-(4-methoxytshenyl) ethylamino]-3-[10,11-dihydro-2-cyano-3-oxy-5H-dibenzo[a,d]cycloheptene-10-(R)-acetic acid]-propan-2-ol hydrochloride salt a) (R)-1-[1,1-dimethyl-2-(4-methoxyphenyl)ethylamino]-3-[10,11-dihydro-2-cyano-3-oxy-5H-dibenzo[a,d]cycloheptene-10-(R)-acetic acid]-propan-2-ol hydrochloride salt.

Following the procedure of Example 41 (h) except substituting (R)-1-[1,1-dimethyl-2-(4-methoxyphenyl) ethylamino]-3-[ethyl-10,11-dihydro-2-cyano-3-oxy-5H-dibenzo[a,d]cycloheptene-10(R)-acetate]-propan-2-ol hydrochloride salt (0.07 g, 0.13 mmol) for the compound of Example 1 (g) 0.03 g (50%) of the title compound was prepared. MS (ES) n/e 504.4 (M+H)$^+$; $^1$H NMR (400 MHz, DMSO-d$_6$) δ 1.1–1.2 (s, 6H), 2.5–3.3 (m, 7H), 3.5–4.3 (m, 12H), 6.8–7.2 (m, 8H), 7.2–7.3 (s, 1H), 7.4–7.5 (s, 1H).

Example 46
Preparation of (R)-1-[1,1-dimethyl-2-(4-methoxyphenyl) ethylamino]-3-[ethyl-10,11-dihydro-2-cyano-3-oxy-5H-dibenzo[a,d]cycloheptene-10(S)-acetate]-propan-2-ol hydrochloride salt.

a) (R)-1-[1,1-dimethyl-2-(4-methoxyphenyl)ethylamino]-3-[ethyl-10,11-dihydro-2-cyano-3-oxy-5H-dibenzo[a,d]cycloheptene-10-(S)-acetate]-propan-2-ol hydrochloride salt.

The 10-R,S-diastereoisomers from Example 42 (b) were resolved as their free base using a Chiralpak AD column (21.2×250 mm, 10 mL/min, 75% hexane/ethanol, 0.1% diethylamine). The pure diastereoisomers were converted to the corresponding HCl salts by treatment with HCl in MeOH to yield (R)-1-[1,1-dimethyl-2-(4-methoxyphenyl) ethylamino]-3-[ethyl-10,11-dihydro-2-cyano-3-oxy-5H-dibenzo[a,d]cycloheptene-10-(S)-acetate]-propan-2-ol hydrochloride salt (20 mg) and (R)-1-[1,1-dimethyl-2-(4-methoxyphenyl)ethylamino]-3-[ethyl-10,11-dihydro-2-cyano-3-oxy-5H-dibenzo[a,d]cycloheptene-10-(R)-acetate]-propan-2-ol hydrochloride salt (20 mg) which was identical to material synthesized in Example 44 (b).

Example 47
Preparation of (R)-1-[1,1-dimethyl-2-(2-naphthyl) ethylamino]-3-[ethyl-10,11-dihydro-2-cyano-3-oxy-5H-dibenzo[a,d]cycloheptene-10-(S)-acetate1-propan-2-ol hydrochloride salt.

a) Ethyl-10,11-dihydro-2-formyl-3-hydroxyl-5H-dibenzo[a,d]cycloheptene-10-(S)-acetate.

Following the procedure of Example 41 (b) except substituting ethyl-10,11-dihydro-3-hydroxyl-5H-dibenzo[a,d]cycloheptene-10-(S)-acetate (1.0 g, 3.4 mmol) for the compound of Example 41 (a) 0.9 g (41%) of the title compound was prepared. $^1$H NMR (400 MHz, DMSO-d$_6$) δ 1.1–1.2 (m, 3H), $_2$.4–4.$_2$ (m, 9H), 6.8–6.9 (s, 1H), 7.0–7.3 (m, 4H), 7.3–7.4 (s, 1H), 10.1–10.2 (s, 1H), 10.5–10.6 (s, 1H).

b) Ethyl-10,11-dihydro-2-iminohydroxyl-3-hydroxyl-5H-dibenzo[a,d]cycloheptene-10-(S)-acetate.

Following the procedure of Example 41 (c) except substituting ethyl-10,11-dihydro-2-formyl-3-hydroxyl-5H-dibenzo[a,d]cycloheptene-10-(S)-acetate(0.9 g, 2.8 mmol) for the compound of Example 41 (b) 0.9 g of the title compound was prepared and used without purification in the next step.

c) Ethyl-10,11-dihydro-2-cyano-3-hydroxyacetyl-5H-dibenzo[a,d]cycloheptene-10-(S)-acetate.

Following the procedure of Example 41 (d) except substituting ethyl-10,11-dihydro-2-iminohydroxyl-3-hydroxyl-5H-dibenzo[a,d]cycloheptene-10-(S)-acetate(0.9 g, 2.6 mmol) for the compound of Example 41 (c) 0.3 g (32%) of the title compound was prepared. $^1$H NMR (400 MHz, DMSO-d$_6$) δ 1.1–1.2 (m, 3H), 2.3–2.4 (s, 3H), 2.5–4.3 (m, 9H), 7.0–7.3 (m, 4H), 7.3–7.4 (s, 1H), 7.6–7.7 (s, 1H).

d) Ethyl-10,11-dihydro-2-cyano-3-hydroxyl-5H-dibenzo[a,d]cycloheptene-10-(S)-acetate.

Following the procedure of Example 41 (e) except substituting ethyl-10,11-dihydro-2-cyano-3-hydroxyacetyl-5H-dibenzo[a,d]cycloheptene-10-(S)-acetate (0.3 g, 2.6 mmol) for the compound of Example 41 (d) 0.3 g (75%) of the title compound was prepared. $^1$H NMR (400 MHz, DMSO-d$_6$) δ 1.1–1.2 (m, 3H), 2.5–4.2 (m, 9H), 6.8–6.9 (s, 1H), 7.0–7.3 (m, 4H), 7.3–7.4 (s, 1H).

e) (2R)-Glycidyl-(ethyl-10,11-dihydro-2-cyano-3-oxyl-5H-dibenzo[a,d]cycloheptene-10-(S)-acetate).

Following the procedure of Example 41 (f) except substituting ethyl-10,11-dihydro-2-cyano-3-hydroxyl-5H-dibenzo[a,d]cycloheptene-10-(S)-acetate(0.2 g, 0.6 mmol) for the compound of Example 41 (e) 0.2 g (87%)of the title compound was prepared and used without further purification in the next step.

f) (R)-1-[1,1-dimethyl-2-(2-naphthyl)ethylamino]-3-[ethyl-10,11-dihydro-2-cyano-3-oxy-5H-dibenzo[a,d]cycloheptene-10-(S)-acetate]-propan-2-ol hydrochloride salt.

Following the procedure of Example 41 (g) except substituting (2R)-glycidyl-(ethyl-10,11-dihydro-2-cyano-3-oxyl-5H-dibenzo[a,d]cycloheptene-10-(S)-acetate).(0.23 g, 0.62 mmol) for the compound of Example 41 (f) 0.3 g (86%) of the title compound was prepared. MS (ES) m/e 577.3 (M+H)$^+$; $^1$H NMR (400 MHz, DMSO-d$_6$) δ 1.1–1.3 (m, 9H), 2.5–4.3 (m, 16H), 7.1–8.0 (m, 13H).

Example 48

Preparation of (R)-1-[1,1-dimethyl-2-(2-naphthyl)ethylamino]-3-[10,11-dihydro-2-cyano-3-oxy-5H-dibenzo[a,d]cycloheptene-10-(S)-acetic acid]-propan-2-ol hydrochloride salt.

a) (R)-1-[1,1-dimethyl-2-(2-naphthyl)ethylamino]-3-[10,11-dihydro-2-cyano-3-oxy-5H-dibenzo[a,d]cycloheptene-10-(S)-acetic acid]-propan-2-ol hydrochloride salt.

Following the procedure of Example 41 (h) except substituting (R)-1-[1,1-dimethyl-2-(2-naphthyl)ethylamino]-3-[ethyl-10,11-dihydro-2-cyano-3-oxy-5H-dibenzo[a,d]cycloheptene-10-(S)-acetate1-propan-2-ol hydrochloride salt (0.14 g, 0.24 mmol) for the compound of Example 41 (g) 0.066 g (50%) of the title compound was prepared. MS (ES) m/e 549.4 (M+H)$^+$; $^1$H NMR (400 MHz, DMSO-d$_6$) δ 1.1–1.3 (m, 6H), 2.5–4.3 (m, 14H), 7.0–7.9 (m, 13H).

Example 49

Preparation of (R)-1-[1,1-dimethyl-2-(4-methoxyphcnyl)ethylamino]-3-[3-oxy-10-ethylthio-5H-dibenzo[a,d]cycloheptenel-propan-2-ol hydrochloride salt a) 3-Hydroxyl-10-ethylthio-5H-dibenzo[a,d]cycloheptene.

A cold solution of 3-hydroxyl-10-oxy-5H-dibenzo[a,d]cycloheptene (3.0 g, 12.6 mmol) and ethylmercaptan (6.5 mL, 86 mmol) in CH$_2$Cl$_2$ (50 mL) was treated with AlCl$_3$ (8.4 g, 60 mmol). After 3 h the solution was concentrated. Flash chromatography (silica gel, 30% EtOAc/Hexane) gave 2.4 g (70%) of the title compound. $^1$H NMR (400 MHz, DMSO-d$_6$) δ 1.1–1.3 (m, 3H), 2.6–2.7 (m, 2H), 3.3–3.4 (s, 2H), 6.5–7.8 (m, 8H), 9.5–9.6 (s, 1H).

b) (2R)-Glycidyl-(3-oxyl-10-ethylthio-5H-dibenzo[a,d]cycloheptene).

Following the procedure of Example 41 (f) except 3-hydroxyl-10-ethylthio-5H-dibenzo[a,d]cycloheptene (1.2 g, 4.5 mmol) for the compound of Example 41 (e) 1.3 g of the title compound was prepared and used without further purification in the next step.

c) (R)-1-[1,1-dimethyl-2-(4-methoxyphenyl)ethylamino]-3-[3-oxy-10-ethylthio-5H-dibenzo[a,dacycloheptene]-propan-2-ol hydrochloride salt.

Following the procedure of Example 41 (g) except substituting (2R)-glycidyl-(3-oxyl-10-ethylthio-5H-dibenzo[a,d]cycloheptene) (0.65 g, 2.0 mmol) for the compound of Example 41 (f) 0.5 g (50%) of the title compound was prepared. MS (ES) m/e 504.3 (M+H)$^+$; $^1$H NMR (400 MHz, DMSO-d$_6$) δ 1.1–1.3 (m, 9H), 2.7–4.2 (m, 14H), 6.8–7.8 (m, 12H).

Example 50

Preparation of (R)-1-[1,1-dimethyl-2-(2-naphthyl)ethylamino]-3-[3-oxy-10-ethylthio-5H-dibenzo[a.dlcyclohepteneI-propan-2-ol hydrochloride salt.

a) (R)-1-[1,1-dimethyl-2-(2-naphthyl)ethylamino]-3-[3-oxy-10-ethylthio-5H-dibenzo[a,d]cycloheptene]-propan-2-ol hydrochloride salt.

Following the procedure of Example 41 (g) except substituting (2R)-glycidyl-(3-oxy-10-ethylthio-5H-dibenzo[a,d]cycloheptene) (0.65 g, 2.0 mmol) for the compound of Example 41 (f) 0.2 g (20%) of the title compound was prepared. MS (ES) m/e 524.3 (M+H)$^+$; $^1$H NMR (400 MHz, DMSO$_6$) δ 1.1–1.3 (m, 9H), 2.7–4.2 (m, I 1H), 6.8–7.8 (m, 14H).

Example 51

Preparation of (R)-1-[1,1-dimethyl-2-(4-methoxyihenyl)ethylamino]-3-[3-oxy-10-oxy-5H-dibenzo[a,d]cyclohептenel-propan-2-ol hydrochloride salt a) (2R)-Glycidyl(3-oxy-10-oxy-5H-dibenzo[a,d]cycloheptene).

Following the procedure of Example 41 (f) except substituting 3-hydroxyl-10-oxy-5H-dibenzo[a,d]cycloheptene (0.9 g, 4.0 mmol) for the compound of Example 41(e) 1.1 g of the title compound was prepared and used without further purification in the next step.

b) (R)-1-[1,1-dimethyl-2-(4-methoxyphenyl)ethylamino]-3-[3-oxy-10-oxy-5H-dibenzo[a,d]cycloheptene]-propan-2-ol hydrochloride salt Following the procedure of Example 41 (g) except (2R)-glycidyl-(3-oxy-10-oxy-5H-dibenzo[a,d]cycloheptene) (0.6 g, 2.1 mmol) for the compound of Example 41 (f) 0.2 g (20%) of the title compound was prepared. MS (ES) m/e 460.3 (M+H)$^+$; $^1$H NMR (400 MHz, DMSO-d$_6$) δ 1.0–1.3 (m, 6H), 2.9–4.3 (m, 14H), 6.8–8.0 (m, 11H).

Example 52

Preparation of (R)-1-[1,1-dimethyl-2-(4-methoxyxhenyl)ethylamino]-3-[ethyl-10,11-dihydro-2-cyano-3-oxy-5HI-dibenzo[a,d]cycloheptene-10(R)-acetate]-propan-2-ol hydrochloride salt.

a) (R)-1-[1,1-dimethyl-2-(4-methoxyphenyl)ethylamino]-3-[ethyl-10,11-dihydro-2-cyano-3-oxy-5H-dibenzo[a,d]cycloheptene-10-(R)-acetate]-propan-2-ol hydrochloride salt.

A solution of (2R)-glycidyl-(ethyl-10,11-dihydro-2-cyano-3-oxy-5H-dibenzo[a,d]cycloheptene-10-(R)-acetate) (0.8 g, 2.1 mmol), 1,1-dimethyl-2-(4-methoxyphenyl)ethyl amine (0.375 g, 2.1 mmol) and LiClO$_4$ (0.445 g, 4.2 mmol) in CH$_3$CN (10 mL) was heated at reflux for 18 hr. The solution was then concentrated. Flash chromatography (silica gel, 5% CH$_3$OH/CH$_2$Cl$_2$) and treatment with HCl in MeOH yielded 0.7 g (60%) of the title compound. MS (ES) m/e 557.3 (M+H)$^+$; $^1$H NMR (DMSO-d$_6$) δ 1.0–1.3 (m, 9H), 2.5–3.2 (m, 8H), 3.4–4.3 (m, 11H), 5.9–6.0 (s, 1H), 6.8–7.2 (m, 8H), 7.2–7.3 (s, 1H), 7.4–7.5 (s, 1H), 8.4–8.5 (broad s, 2H).

Example 53

Preparation of (R)-1-[1,1-dimethyl-2-(2-naphthalenyl)ethylamino]-3-[3-oxy-dibenz[b,f][1,4]oxazepin-11(10H)-one]-propan-2-ol monohydrochloride.

a) 2-Carboxymethyl-5-methoxy-phenyl-oxy-(3-nitrobenzene)

A solution of 2-carboxymethyl-5-methoxyphenol (34.1 g, 0.187 mol), 2-nitrofluorobenzene (19.7 mL, 0.187 mol), and $K_2CO_3$ (65 g, 0.467 mol) in DMF (200 mL) was heated to 110° C. for 18 h. The solution was diluted with water (200 mL) and extracted with ethyl acetate. The ethyl acetate layer was concentrated to give the crude title compound which was used as is for the next step (57 g).

b) 2-Carboxymethyl-5-methoxy-phenyl-oxy-(3-aminobenzene)

A solution of 2-carboxymethyl-5-methoxy-phenyl-oxy-(3-nitrobenzene) (57 g, 0.187 mol) and 10% Pd/C (11 g) was hydrogenated in MeOH (1000 mL) at 50 psi for 2 h. The solution was filtered through Celite® and the filtrate was concentrated. Flash chromatography (silica gel, 20% EtOAc/Hexane) yielded the title compound (49.3 g, 96%): MS (ES) m/e 274.1 $(M+H)^+$.

c) 3-Methoxy-dibenz[b,f][1,4]oxazepin-11(10H).

A solution of 2-carboxymethyl-5-methoxy-phenyl-oxy-(3-aminobenzene) (9.2 g, 37 mmol) in toluene (400 mL) was treated with $AlMe_3$ (2M in toluene, 16 mL, 32 mmol). The solution was heated at reflux for 3 h and allowed to run at RT for 18 h. The reaction solution was poured into a 5% $NaHCO_3$ solution and ethyl acetate was added. The ethyl acetate layer was separated and washed with water (2×) and brine (1×). The ethyl acetate layer was concentrated to give the title compound (7.4 g, 91%): $^1$H NMR (400 MHz, DMSO-$d_6$) δ 3.8–3.9 (s, 3H), 6.8–7.9 (m, 7H).

d) 3-Hydroxy-dibenz[b,f][1,4]oxazepin-11(10H).

To a cold solution of 9-methoxy-dibenz[b,f][1,4]oxazepin-11(10H) (1 g, 4.1 mmol) and ethylmercaptan (1.5 mL, 20 mmol) in $CH_2Cl_2$ (15 mL) was added $AlCl_3$ (2.8 g, 20 mmol). After 2 h at 0° C., the solution was concentrated and residue was treated with ice/water (50 mL) and $CH_2Cl_2$ (50 mL). The organic layer was separated and washed with water (2×). The organic layer was concentrated to give the crude title compound which was used as is for the next step (0.95 g). $^1$H NMR (400 MHz, DMSO-$d_6$) δ 6.4–7.9 (m, 7H), 10.1–10.2 (s, 1H), 10.4–10.5 (s, 1H).

e) 2-R-Glycidyl-(9-oxy-dibenz[b,f][1,4]oxazepin-11 (10H)

A solution of 9-hydroxy-dibenz[b,f][1,4]oxazepin-11 (10H) (0.51 g 2.2 mmol), 2-R-gycidyl 3-nitrobenzenesulfonate (0.582 g, 2.2 mmol) and $K_2CO_3$ (0.93 g, 6.6 mmol) in acetone (20 mL) was heated to reflux for 18 hr. Solution was filtered and the filtrate was concentrated to give the title compound which was used as is for the next step (0.64 g).

f) (R)-1-[1,1-Dimethyl-2-(2-naihthalenyl)ethylamino]-3-[3-oxy-dibenz[b,f][1,4]oxazepin-11(10H)-one]-propan-2-ol monohydrochloride.

A solution of 2R-glycicyl-(9-oxy-dibenz[b,f][1,4]oxazepin-11(10H)(0.10 g, 0.4 mmol) and 1,1-dimethyl-2-(2-naphthyl)ethyl amine (0.07 g, 0.4 mmol) in EtOH (5 mL) was heated to reflux for 18 hr. The solution was concentrated. and purified by flash chromatography (silica gel, 5% $CH_3OH/CH_2Cl_2$). Treatment of the isolated product with HCl in MeOH yielded the title compound (0.1 g, 60%). MS (ES) m/e 483.1 $(M+H)^+$; $^1$HNMR (DMSO-$d_6$) δ 1.2–1.4 (m, 6H), 2.5–4.5 (m, 8H), 6.0–6.1 (s, 1H), 6.8–7.9 (m, 8H), 8.7–9.2 (m, 2H), 10.3–10.4 (s, 1H).

Example 54

Preparation of (R)-1-[1,1-dimethyl-2-(2-naphthalenyl) ethylamino]-3-[3-oxy-9,10-dihydrodibenz [b,f][1,4] oxazepin]-2-propanol monohydrochloride.

a) 3-Methoxy-(9,10-dihydrodibenz[b,f][1,4]azepin).

A solution of 3-methoxy-dibenz[b,f][1,4]oxazepin-11 (10H) (7.4 g, 30.7 mmol) in THF (200 mL) was treated dropwise with $LiAlH_4$ (30 mL, 1M in THF). Solution was cooled to 0° C. and treated carefully with water (2 mL). After 20 min., NaF (5 g, 120 mmol) in water (10 mL) was added to the solution. The solution was stirred at RT for 1 h. The solution was filtered and filtrate was concentrated to give the crude title compound which is used as is for the next step (7.6 g). MS (ES) m/e 228.0 $(M+H)^+$.

b) 3-Hydroxy-(9,10-dihydrodibenz[b,f][1,4]azepin).

Following the procedure of Example 53 (d) except substituting 3-methoxy-(9,10-dihydrodibenz[b,f][1,4]azepin) (1 g, 4.4 mmol) for the compound of Example 53 (c), the crude title compound was prepared and used as is for the next step (0.89 g).

c) 2R-Glycidyl-(3-oxy-dibenz[b,f][1,4] azepin-11(10H)

Following the procedure of Example 53 (e) except substituting 3-hydroxy-(9,10-dihydrodibenz[b,f][1,4]azepin) (0.89 g, 4.4 mmol) for the compound of Example 53 (d) the crude title compound was prepared and used as is for the next step (1.0 g).

d) (R)-1-[1,1-dimethyl-2-(2-naphthalenyl)ethylamino]-3-[3-oxy-9,10-dihydrodibenz[b,f][1,4]oxazepin]-2-propanol monohydrochloride.

Following the procedure of Example 53 (f) except substituting 2-R-glycicyl-(3-oxy-dibenz[b,f][1,4] azepin-11 (10H) (0.4 g, 1.5 mmol) for the compound of Example 53 (g) the title compound was prepared (0.3 g, 43%). MS (ES) m/e 469.2 $(M+H)^+$. $^1$HNMR (400 MHz, DMSO-$d_6$) δ 1.2–1.3 (s, 6H), 2.4–4.3 (m, 7H), 6.7–8.0 (m, 14H), 8.7–9.3 (m, 2H).

Example 55

Preparation of (R)-1-[1,1-dimethyl-2-(2-naphthalenyl) ethylamino]-3-[3-oxy-9,10-dihydrodibenz [b,f][1,4] oxazepin-11(10H)-ethylcarboxymethyl]-propan-2-ol monohydrochloride a) Ethyl-3-methoxy-dibenz[b,f][1,4]azepine-11(10H)-acetate A solution of 3-methoxy-(9,10-dihydrodibenz[b,f][1,4] azepin (1.0 g, 4.4 mmol), triethylamine (0.6 mL, 4.4 mmol) and methylbromoacetate (0.49 mL, 4.4 mmol) in acetonitrile (10 mL) was heated at reflux for 18 h. The solution was concentrated to give the crude title compound and used as is for the next step (1.2 g).

b) Ethyl-3-hydroxy-dibenz[b,f][1,4]azepine-11(10H)-acetate

Following the procedure of Example 53 (d) except substituting ethyl-3-methoxy-dibenz[b,f][1,4]azepine-11(10H)-acetate (1.2 g, 4.4 mmol) for the compound of Example 53 (c) the crude title compound was prepared and used as is for the next step (1.1 g).

c) Ethyl 2R-Glycidyl-(3-oxy-dibenz[b,f][1,4] azepin-11 (10H)acetate

Following the procedure of Example 53 (e) except substituting ethyl-3-hydroxy-dibenz[b,f][1,4]azepine-11(10H)-acetate (1.6 g, 4.4 mmol) for the compound of Example 53 (d) the crude title compound was prepared and used as is for the next step (1.7 g)

d) (R)-1-[1,1-dimethyl-2-(2-naphthalenyl)ethylamino]-3-[3-oxy-9,10-dihydrodibenz[b,f][1,4]oxazepin-11(10H)-ethylcarboxymethyl]-propan-2-ol monohydrochloride Following the procedure of Example 53 (f) except substituting ethyl 2R-glycidyl-(3-oxy-dibenz[b,f][1,4] azepin- 11(10H)acetate (0.09 g, 0.25 mmol) for the compound of Example 53 (g) the title compound was prepared (0.07 g, 50%). MS (ES) m/e 555.2 (M+H)+; $^1$H NMR (400 MHz, DMSO-d$_6$) δ 1.0–1.3 (s, 9H), 2.4–4.6 (m, 9H), 6.7–8.0 (m, 14H), 8.7–9.3 (m, 2H).

The above nuclear magnetic resonance spectra are recorded at either 250 or 400 MHz using, respectively, a Bruker AM 250 or Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million δ downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz (Hz). Continuous wave infrared (IR) spectra are recorded on a Perkin-Elmer 683 infrared spectrometer, and Fourier transform infrared (FTIR) spectra are recorded on a Nicolet Impact 400 D infrared spectrometer. IR and FTIR spectra are recorded in transmission mode, and band positions are reported in inverse wavenumbers (cl-1). Mass spectra are taken on either VG 70 FE, PE Syx API III, or VG ZAB HF instruments, using fast atom bombardment (FAB) or electrospray (ES) ionization techniques. Elemental analyses are obtained using a Perkin-Elmer 240C elemental analyzer. Melting points are taken on a Thomas-Hoover melting point apparatus and are uncorrected. All temperatures are reported in degrees Celsius.

Analtech Silica Gel GF and E. Merck Silica Gel 60 F-254 thin layer plates are used for thin layer chromatography. Both flash and gravity chromatography are carried out on E. Merck Kieselgel 60 (230–400 mesh) silica gel. Analytical and preparative HPLC are carried out on Rainin or Beckman chromatographs. ODS refers to an octadecylsilyl derivatized silica gel chromatographic support. 5 uApex-ODS indicates an octadecylsilyl derivatized silica gel chromatographic support having a nominal particle size of 5 u, made by Jones Chromatography, Littleton, Colo. YMC OQS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

Formulations for pharmaceutical use incorporating compounds of the present invention can be prepared in various forms and with numerous excipients. Examples of such formulations are given below.

Example 56

Inhalant Formulation

A compound of Formula (I), (1 mg to 100 mg) is aerosolized from a metered dose inhaler to deliver the desired amount of drug per use.

Tablet Formulation

| Tablets/Ingredients | | Per Tablet |
|---|---|---|
| 1. | Active ingredient (Cpd of Form. (I) | 40 mg |
| 2. | Corn Starch | 20 mg |
| 3. | Alginic acid | 20 mg |

-continued

Tablet Formulation

| Tablets/Ingredients | | Per Tablet |
|---|---|---|
| 4. | Sodium Alginate | 20 mg |
| 5. | Mg stearate | 1.3 mg |

Procedure for tablet formulation:

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

Example 58

Parenteral Formulation

A pharmaceutical composition for parenteral administration is prepared by dissolving an appropriate amount of a compound of formula I in polyethylene glycol with heating. This solution is then diluted with water for injections (to 100 mL). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound selected from the group consisting of:

(R)-3-[2-cyano-4-[N-benzyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[methylsulfonyl]amino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(4-methoxyphenyl)ethylamino]-propan-2-ol;

(R)-3-[2-cyano-4-[N-methylsulfonylamino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(2-naphthyl)ethylamino]-propan-2-ol;

(R)-3-[2-cyano-4-[N-[methylsulfonyl]amino]phenoxy]-1-[1,1-dimethyl-2-(2-naphthyl)ethylamino]-propan-2-ol;

(R)-3-[2-cyano-4-[N-benzyl-N-[4-methylphenylsulfonyl]amino]phenoxy]-1-[1,1-dimethyl-2-(2-naphthyl)ethylamino]-propan-2-ol;

(R)-3-[2-cyano-4-[N-benzyl-N-[4-methylphenylsulfonyl]amino]phenoxy]-1-[1,1-dimethyl-2-(benzyloxy)ethylamino]-propan-2-ol;

(R)-3-[2-cyano-4-[N-benzyl-N-[4-methylphenylsulfonyl]amino]phenoxy]-1-[1,1-dimethyl-3-phenylpropylamino]-propan-2-ol;

(R)-3-[2-cyano-4-[N-benzyl-N-[4-methylphenylsulfonyl]amino]phenoxy]-1-[1,1-dimethyl-4-phenylbutylamino]-propan-2-ol;

(R)-3-[2-cyano-4-[N-benzyl-N-ethylcarbonyl]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(4-methoxyphenyl)ethylamino]-propan-2-ol;

(R)-3-[2-cyano-4-[N-methyl-N'-morpholino]ureido]phenoxy]-1-[1,1-dimethyl-2-(2-naphthyl)ethylamino]-propan-2-ol;

(R)-3-[2-cyano-4-[N-methyl-N'-morpholino]ureido]phenoxy]-1-[1,1-dimethyl-2-(4-methoxyphenyl)ethylamino]-propan-2-ol;

(R)-1-[1,1-dimethyl-2-(4-methoxyphenyl)ethylamino]-3-[2-cyano-4-(N,N-dipropylaminocarbonyl)phenoxy]-propan-2-ol;

(R)-1-[1,1-dimethyl-2-(4-methoxyphenyl)ethylamino]-3-[2-cyano-4-(N-propylaminocarbonyl)phenoxy]-propan-2-ol;

(R)-1-[1,1-dimethyl-2-(4-methoxyphenyl)ethylamino]-3-[2-cyano-4-(N-piperidinylcarbonyl)phenoxy]-propan-2-ol;

(R)-1-[1,1-dimethyl-2-(4-methoxyphenyl)ethylamino]-3-[2-cyano-4-(N-morpholinylcarbonyl)phenoxy]-propan-2-ol;

(R)-1-[1,1-dimethyl-2-(4-methoxyphenyl)ethylamino]-3-[2,3-dichloro-4-(N-morpholinylcarbonyl)phenoxy]-propan-2-ol;

(R)-1-[1,1-dimethyl-2-(2-naphthyl)ethylamino]-3-[2,3-dichloro-4-(N-morpholinylcarbonyl)phenoxy]-propan-2-ol;

(R)-1-[1,1-dimethyl-2-(4-methoxyphenyl)ethylamino]-3-[2,3-dichloro-4-(N,N-dipropylaminocarbonyl)phenoxy]-propan-2-ol;

(R)-1-[1,1-dimethyl-2-(2-naphthyl)ethylamino]-3-[2,3-dichloro-4-(N,N-dipropylaminocarbonyl)phenoxy]-propan-2-ol;

(R)-1-[1,1-dimethyl-2-(4-methoxyphenyl)ethylamino]-3-[2-cyano, 3-chloro-4-(N-morpholinylcarbonyl)phenoxy]-propan-2-ol;

(R)-1-[1,1-dimethyl-2-(2-naphthyl)ethylamino]-3-[2-cyano, 3-chloro-4-(N-morpholinylcarbonyl)phenoxy]-propan-2-ol;

(R)-1-[1,1-dimethyl-2-(4-methoxyphenyl)ethylamino]-3-[2-cyano, 3-chloro-4-(N,N-dipropylaminocarbonyl)phenoxy]-propan-2-ol;

(R)-1-[1,1-dimethyl-2-(2-naphthyl)ethylamino]-3-[2-cyano, 3-chloro-4-(N,N-dipropylaminocarbonyl)phenoxy]-propan-2-ol;

(R)-1-[1,1-dimethyl-2-(4-methoxyphenyl)ethylamino]-3-[2-cyano-4-(N-pyrrolidinylcarbonyl)phenoxy]-propan-2-ol;

(R)-1-[1,1-dimethyl-2-(4-methoxyphenyl)ethylamino]-3-[2-cyano-4-(N-piperazinylcarbonyl)phenoxy]-propan-2-ol;

(R)-1-[1,1-dimethyl-2-(2-naphthyl)ethylamino]-3-[2-cyano-4-(N,N-dipropylaminocarbonyl)phenoxy]-propan-2-ol;

(R)-1-[1,1-dimethyl-2-(2-naphthyl)ethylamino]-3-[2-cyano-4-(N-piperidinylcarbonyl)phenoxy3-propan-2-ol;

(R)-1-[1,1-dimethyl-2-(2-naphthyl)ethylamino]-3-[2-cyano-4-(N-morpholinylcarbonyl)phenoxy]-propan-2-ol;

(R)-1-[1,1-dimethyl-2-(2-naphthyl)ethylamino]-3-[2-cyano-4-(N-piperazinylcarbonyl)phenoxy]-propan-2-ol;

(R)-1-[1,1-dimethyl-2-(2-naphthyl)ethylamino]-3-[2-cyano-4-(N-pyrrolidinylcarbonyl)phenoxy]-propan-2-ol;

(R)-1-[1,1-dimethyl-3-(phenyl)propylamino]-3-[2-cyano-4-(N,N-dipropylaminocarbonyl)phenoxy]-propan-2-ol;

(R)-1-[1,1-dimethyl-4-(phenyl)butylamino]-3-[2-cyano-4-(N,N-dipropylaminocarbonyl)phenoxy]-propan-2-ol;

(R)-1-[1,1-dimethyl-3-(phenoxy)propylamino]-3-[2-cyano-4-(N,N-dipropylaminocarbonyl)phenoxy]-propan-2-ol;

(R)-1-[1,1-dimethyl-2-(oxybenzyl)ethylamino]-3-[2-cyano-4-(N,N-dipropylaminocarbonyl)phenoxy]-propan-2-ol;

N-[3-(3-chloro-2-cyano-4-dipropylsulfamoyl)phenoxy-2(R)-hydroxypropyl]-2-(4-methoxyphenyl)-1,1-dimethylethylamine;

N-[3-(2,3-dichloro-4-dipropylsulfamoyl)phenoxy-2(R)-hydroxypropyl]-2-(2,3-dichlorophenyl)-1,1-dimethylethylamine;

N-[3-(3-chloro-2-cyano-4-dimethylsulfamoyl)phenoxy-2(R)-hydroxypropyl]-2-(4-methoxyphenyl)-1,1-dimethylethylamine;

N-[3-(2,3-dichloro-4-morpholinosulfamyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2(R)-hydroxypropyl]-2-(4-methoxyphenyl)-1,1-dimethylethylamine;

N-[3-(3-chloro-2-cyano-4-pyrrolidinosulfamyl)phenoxy-2(R)-hydroxypropyl]-2-(4-methoxyphenyl)-1,1-dimethylethylamine;

N-[3-(3-chloro-2-cyano-4-pyrrolidinosulfamyl)phenoxy-2(R)-hydroxypropyl]-2-(2-naphthyl)-1,1-dimethylethylamine;

N-[3-(3-chloro-2-cyano-4-morpholinosulfamyl)phenoxy-2(R)-hydroxypropyl]-2-(2-naphthyl)-1,1-dimethylethylamine;

N-[3-(3-chloro-2-cyano-4-thiomorpholinosulfamyl)phenoxy-2(R)-hydroxypropyl]-2-(2-naphthyl)-1,1-dimethylethylamine;

N-[3-(3-chloro-2-cyano-4-thiomorpholinosulfamyl)phenoxy-2(R)-hydroxypropyl]-2-(4-methoxyphenyl)-1,1-dimethylethylamine;

N-[3-[3-chloro-2-cyano-4-(2'-cyanoeth-1-yl)-cyclopropylsulfamoyl]phenoxy-2(R)-hydroxypropyl]-2-(4-methoxyphenyl)-1,1-dimethylethylamine;

N-[3-[3-chloro-2-cyano-4-(2'-cyanoeth-1-yl)-cyclopropylsulfamoyl]phenoxy-2(R)-hydroxypropyl]-2-(2-napthyl)-1,1-dimethylethylamine;

N-[3-[3-chloro-2-cyano-4-(benzyl-cyclopropyl)
  sulfamoyl]phenoxy-2(R)-hydroxypropyl]-2-(2-
  napthyl)-1,1-dimethylethylamine;
N-[3-[3-chloro-2-cyano-4-(benzyl-cyclopropyl)
  sulfamoyl]phenoxy-2(R)-hydroxypropyl]-2-(4-
  methoxyphenyl)-1,1-dimethylethylamine;
N-[3-[3-chloro-2-cyano-4-(4'-N-t-
  butoxycarbonylpiperazino)sulfamyl]phenoxy-2(R)-
  hydroxypropyl]-2-(4-methoxyphenyl)-1,1-
  dimethylethylamine;
N-[3-[3-chloro-2-cyano-4-(4'-N-t-
  butoxycarbonylpiperazino)sulfamyl]phenoxy)-2(R)-
  hydroxypropyl]-2-(2-naphthyl)-1,1-
  dimethylethylamine;
N-[3-(2,3-dichloro-4-dipropysulfamoyl)phenoxy-2(R)-
  hydroxypropyl]-2-(2-naphthyl)-1,1-
  dimethylethylamine;
N-[3-(2,3-dichloro-4-pyrrolidinolsulfamoyl)phenoxy-2
  (R)-hydroxypropyl]-2-(4-methoxyphenyl)-1,1-
  dimethylethylamine;
N-[3-(2,3-dichloro-4-pyperidinolsulfamoyl)phenoxy-2
  (R)-hydroxypropyl]-2-(4-methoxyphenyl)-1,1-
  dimethylethylamine;
N-[3-(2,3-dichloro-4-cyclopropylsulfamoyl)phenoxy-2
  (R)-hydroxypropyl]-2-(4-methoxyphenyl)-1,1-
  dimethylethylamine;
N-[3-(2,3-dichloro-4-dipropylsulfamoyl)phenoxy-2(R)-
  hydroxypropyl]-2-(4-methoxyphenyl)-1,1-
  dimethylethylamine;
N-[3-(2,3-dichloro-4-propylsulfamoyl)phenoxy-2(R)-
  hydroxypropyl]-2-(4-methoxyphenyl)-1,1-
  dimethylethylamine;
N-[3-(2,3-dichloro-4-sulfamoyl)phenoxy-2(R)-
  hydroxypropyl]-2-(4-methoxyphenyl)-1,1-
  dimethylethylamine;
N-[3-(2,3-dichloro-4-methylsulfamoyl)phenoxy-2(R)-
  hydroxypropyl]-2-(4-methoxyphenyl)-1,1-
  dimethylethylamine;
N-[3-(3-chloro-2-cyano-4-pyrrolidinosulfamyl)phenoxy-
  2(R)-hydroxypropyl]-2-(4-fluorophenyl)-1,1-
  dimethylethylamine;
N-[3-(3-chloro-2-cyano-4-morphoinosulfamyl)phenoxy-
  2(R)-hydroxypropyl]-2-(benzyloxy)-1,1-
  dimethylethylamine;
N-[3-(2,3-dichloro-4-morpholinosulfamyl)phenoxy-2
  (R)-hydroxypropyl]-3-phenyl-1,1-
  dimethylpropylamine;
N-[3-(2,3-dichloro-4-morpholinosulfamyl)phenoxy-2
  (R)-hydroxypropyl]-4-phenyl-1,1-
  dimethylbutylamine;
or a pharmaceutically acceptable salt thereof.

2. A compound according to claim 1 selected from the group consisting of:
  (R)-3-[2-cyano-4-[N-benzyl-N-[4-methylphenylsulfonyl]
    amino]phenoxy]-1-[1,1-dimethyl-2-(4-
    methoxyphenyl)ethylamino]-propan-2-ol;
  (R)-3-[2-cyano-4-[N-[4-methylphenylsulfonyl]amino]
    phenoxy]-1-[1,1-dimethyl-2-(4-methoxyphenyl)
    ethylamino]-propan-2-ol;
  (R)-3-(2-cyano-4-[N-methyl-N-[4-
    methylphenylsulfonyl]amino]phenoxy]-1-[1,1-
    dimethyl-2-(4-methoxyphenyl)ethylamino]-propan-2-
    ol;
  (R)-3-[2-cyano-4-[N-methyl-N-[methylsulfonyl]amino]
    phenoxy]-1-[1,1-dimethyl-2-(4-methoxyphenyl)
    ethylamino]-propan-2-ol;
  (R)-3-[2-cyano-4[N-benzyl-N-[methylsulfonyl]amino]
    phenoxy]-1-[1,1-dimethyl-2-(4-methoxyphenyl)
    ethylamino]-propan-2-ol;
  (R)-3-[2-cyano-4-[N-methylsulfonylamino]phenoxy]-1-
    [1,1-dimethyl-2-(4-methoxyphenyl)ethylamino]-
    propan-2-ol;
  (R)-3-[2-cyano-4-[N-benzyl-N-[methylsulfonyl]amino]
    phenoxy]-1-[1,1-dimethyl-2-(2-naphthyl)ethylamino]-
    propan-2-ol;
  (R)-3-[2-cyano-4-[N-[methylsulfonyl]amino]phenoxy]-
    1-[1,1-dimethyl-2-(2-naphthyl)ethylamino]-propan-2-
    ol;
  (R)-3-[2-cyano-4-[N-benzyl-N-[4-methylphenylsulfonyl]
    amino]phenoxy]-1-[1,1-dimethyl-2-(2-naphthyl)
    ethylamino]-propan-2-ol;
  (R)-3-[2-cyano-4-[N-benzyl-N'-morpholino]ureido]
    phenoxy]-1-[1,1-dimethyl-2-(2-naphthyl)ethylamino]-
    propan-2-ol;
  (R)-3-[2-cyano-4-[N-benzyl-N'-morpholino]ureido]
    phenoxy]-1-[1,1-dimethyl-2-(4-methoxyphenyl)
    ethylamino]-propan-2-ol;
  (R)-3-[2-cyano-4-[N-methyl-N'-morpholino]ureido]
    phenoxy]-1-[1,1-dimethyl-2-(2-naphthyl)ethylamino]-
    propan-2-ol;
  (R)-3-[2-cyano-4-[N-methyl-N'-morpholino]ureido]
    phenoxy]-1-[1,1-dimethyl-2-(4-methoxyphenyl)
    ethylamino]-propan-2-ol;
  (R)-1-[1,1-dimethyl-2-(4-methoxyphenyl)ethylamino]-3-
    [2-cyano-4-(N,N-dipropylaminocarbonyl)phenoxy]-
    propan-2-ol;
  (R)-1-[1,1-dimethyl-2-(4-methoxyphenyl)ethylamino]-3-
    [2-cyano-4-(N-piperidinylcarbonyl)phenoxy]-propan-
    2-ol;
  (R)-1-[1,1-dimethyl-2-(4-methoxyphenyl)ethylamino]-3-
    [2-cyano, 3-chloro-4-(N,N-dipropylaminocarbonyl)
    phenoxy]-propan-2-ol;
  (R)-1-[1,1-dimethyl-2-(2-naphthyl)ethylamino]-3-[2-
    cyano, 3-chloro-4-(N,N-dipropylaminocarbonyl)
    phenoxy]-propan-2-ol;
  (R)-1-[1,1-dimethyl-2-(4-methoxyphenyl)ethylamino]-3-
    [2-cyano-4-(N-pyrrolidinylcarbonyl)phenoxy]-propan-
    2-ol;
  (R)-1-[1,1-dimethyl-2-(2-naphthyl)ethylamino]-3-[2-
    cyano-4-(N,N-dipropylaminocarbonyl)phenoxy]-
    propan-2-ol;
  (R)-1-[1,1-dimethyl-2-(2-naphthyl)ethylamino]-3-[2-
    cyano-4-(N-piperidinylcarbony)phenoxy]-propan-2-ol;
  (R)-1-[1,1-dimethyl-2-(2-naphthyl)ethylamino]-3-[2-
    cyano-4-(N-pyrrolidinylcarbonyl)phenoxy]-propan-2-
    ol; N-[3-(3-chloro-2-cyano-4-dimethylsulfamoyl)
    phenoxy-2(R)hydroxypropyl]-2-(4-methoxyphenyl)-1,
    1-dimethylethylamine;
  N-[3-(2,3-dichloro-4-morpholinosulfamyl)phenoxy-2
    (R)-hydroxypropyl]-2-(4-methoxyphenyl)-1,1-
    dimethylethylamine;
  N-[3-(3-chloro-2-cyano-4-morpholinosulfamyl)phenoxy-
    2(R)-hydroxypropyl]-2-(4-methoxyphenyl)-1,1-
    dimethylethylamine;
  N-[3-(3-chloro-2-cyano-4-pyrrolidinosulfamyl)phenoxy-
    2(R)-hydroxypropyl]-2-(4-methoxyphenyl)-1,1-
    dimethylethylamine;
  N-[3-(3-chloro-2-cyano-4-pyrrolidinosulfamyl)phenoxy-
    2(R)-hydroxypropyl]-2-(2-naphthyl)-1,1-
    dimethylethylamine;

N-[3-(3-chloro-2-cyano-4-morpholinosulfamyl)phenoxy-2(R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]-2-(4-methoxyphenyl)-1,1-dimethylethylamine;

N-[3-[3-chloro-2-cyano-4-(benzyl-cyclopropyl) sulfamnoyl]phenoxy-2(R)-hydroxypropyl]-2-(2-napthyl)-1,1-dimethylethylamine;

N-[3-[3-chloro-2-cyano-4-(benzyl-cyclopropyl) sulfamoyl]phenoxy-2(R)-hydroxypropyl]-2-(4-methoxyphenyl)-1,1-dimethylethylamine;

N-[3-(2,3-dichloro-4-dipropylsulfamoyl)phenoxy-2(R)-hydroxypropyl]-2-(2-naphthyl)-1,1-dimethylethylamine;

N-[3-(2,3-dichloro-4-pyrrolidinolsulfamyl)phenoxy-2(R)-hydroxypropyl]-2-(4-methoxyphenyl)-1,1-dimethylethylamine;

N-[3-(2,3-dichloro-4-piperidinolsulfamyl)phenoxy-2(R)-hydroxypropyl][2-(4-methoxyphenyl)-1,1-dimethyl]ethylamine;

N-[3-[3-chloro-2-cyano-4-(2'-cyanoeth-1-yl)-cyclopropylsulfamoyl]phenoxy-2(R)-hydroxypropyl]-2-(4-methoxyphenyl)-1,1-dimethylethylamine;

N-[3-[3-chloro-2-cyano-4-(2'-cyanoeth-1-yl)-cyclopropylsulfamoyl]phenoxy-2(R)-hydroxypropyl]-2-(2-napthyl)-1,1-dimethylethylamine;

N-[3-(3-chloro-2-cyano-4-morpholinosulfamyl)phenoxy-2(R)-hydroxypropyl]-2-(benzyloxy)-1,1-dimethylethylamine;

N-[3-(2,3-dichloro-4-dipropylsulfamoyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2(R)-hydroxypropyl]-2-(benzyloxy)-1,1-dimethylethylamine;

N-[3-(2,3-dichloro-4-morpholinosulfamyl)phenoxy-2(R)-hydroxypropyl]-3-phenyl-1,1-dimethylpropylamine;

N-[3-(2,3-dichloro-4-morpholinosulfamyl)phenoxy-2(R)-hydroxypropyl]-4-phenyl-1,1-dimethylbutylamine;

or a pharmaceutically acceptable salt thereof.

3. A compound according to claim 2 selected from the group consisting of:

(R)-3-[2-cyano-4-[N-benzyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[4-methylphenylsulfonyl]amino]phenoxy]-1-[1,1-dimethyl-2-(4-methoxyphenyl)ethylamino]-propan-2-ol;

(R)-3-[2-cyano-4-[N-methyl-N-[methylsulfonyl]amino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(4-methoxyphenyl)ethylamino]-propan-2-ol;

(R)-3-[2-cyano-4-[N-benzyl-N-[methylsulfonyl]amino]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(2-naphthyl)ethylamino]-propan-2-ol;

(R)-3-[2-cyano-4-[N-benzyl-N'-morpholino]ureido]phenoxy]-1-[1,1-dimethyl-2-(4-methoxyphenyl)ethylamino]-propan-2-ol;

(R)-3-[2-cyano-4-[N-methyl-N'-morpholino]ureido]phenoxy]-1-[1,1-dimethyl-2-(2-naphthyl)ethylamino]-propan-2-ol;

(R)-3-[2-cyano-4-[N-methyl-N'-morpholino]ureido]phenoxy]-1-[1,1-dimethyl-2-(4-methoxyphenyl)ethylamino]-propan-2-ol (R)-3-[2-cyano-4-[N-benzyl-N-[4-methylphenylsulfonyl]amino]phenoxy]-1-[1,1-dimethyl-2-(2-naphthyl)ethylamino]-propan-2-ol;

(R)-1-[1,1-dimethyl-2-(4-methoxyphenyl)ethylamino]-3-[2-cyano-4-(N,N-dipropylaminocarbonyl)phenoxy]-propan-2-ol;

(R)-1-[1,1-dimethyl-2-(4-methoxyphenyl)ethylamino]-3-[2-cyano-4-(N-piperidinylcarbonyl)phenoxy]-propan-2-ol;

(R)-1-[1,1-dimethyl-2-(4-methoxyphenyl)ethylamino]-3-[2-cyano-4-(N-pyrrolidinylcarbonyl)phenoxy]-propan-2-ol;

(R)-1-[1,1-dimethyl-2-(2-naphthyl)ethylamino]-3-[2-cyano-4-(N,N-dipropylaminocarbonyl)phenoxy]-propan-2-ol;

(R)-1-[1,1-dimethyl-2-(2-naphthyl)ethylamino]-3-[2-cyano-4-(N-piperidinylcarbonyl)phenoxy]-propan-2-ol;

(R)-1-[1,1-dimethyl-2-(2-naphthyl)ethylamino]-3-[2-cyano-4-(N-pyrrolidinylcarbonyl)phenoxy]-propan-2-ol;

N-[3-(2,3-dichloro-4-morpholinosulfamyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2(R)-hydroxypropyl]-2-(4-methoxyphenyl)-1,1-dimethylethylamine;

N-[3-(3-chloro-2-cyano-4-pyrrolidinsulfamoyl)phenoxy-2(R)-hydroxypropyl]-2-(4-methoxyphenyl)1,1-dimethylethylamine;

N-[3-(3-chloro-2-cyano-4-pyrrolidinosulfamyl)phenoxy-2(R)-hydroxypropyl]-2-(2-naphthyl)-1,1-dimethylethylamine;

N-[3-(3-chloro-2-cyano-4-morpholinosulfarnyl)phenoxy-2(R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]-2-(2-naphthyl)-1,1-dimethylethylamine;

N-[3-(3-chloro-2-cyano-4-thiomorpholinosulfamyl) phenoxy-2(R)-hydroxypropyl]2-(4-methoxyphenyl)-1,1-dimethylethylamine;

N-[3-(2,3-dichloro-4-pyrrolidinolsulfamyl)phenoxy-2(R)-hydroxypropyl]-2-(4-methoxyphenyl)-1,1-dimethylethylamine;

N-[3-(2,3-dichloro-4-piperidinolsulfamyl)phenoxy-2(R)-hydroxypropyl]-2-(4-methoxyphenyl)-1,1-dimethylethylamine;

N-[3-(3-chloro-2-cyano-4-morpholinosulfamyl)phenoxy-2(R)-hydroxypropyl]-2-(benzyloxy)-1,1-dimethylethylamine;

N-[3-[3-chloro-2-cyano-4-(2'-cyanoeth-1-yl)cyclopropylsulfamoyl]phenoxy-2(R)-hydroxypropyl]-2-(4-methoxyphenyl)-1,1-dimethylethylamine;

N-[3-[3-chloro-2-cyano-4-(2'-cyanoeth-1-yl)cyclopropylsulfamoyl]phenoxy-2(R)-hydroxypropyl]-2-(2-napthyl)-1,1-dimethylethylamine;

N-[3-(3-chloro-2-cyano-4-morpholinosulfamyl)phenoxy-2(R)-hydroxypropyl]-2-(benzyloxy)-1,1-dimethylethylamine;

N-[3-(2,3-dichloro-4-morpholinosulfamyl)phenoxy-2(R)-hydroxypropyl]4-phenyl-1,1-dimethylbutylamine;

N-[3-(2,3-dichloro-4-morpholinosulfamyl)phenoxy-2(R)-hydroxypropyl]-3-phenyl-1,1-dimethylpropylamine;

N-[3-(2,3-dichloro-4-morpholinosulfamyl)phenoxy-2(R)-hydroxypropyl]-4-phenyl-1,1-dimethylbutylamine;

or a pharmaceutically salt thereof.

4. A method of antagonizing a calcium receptor which comprises administering to a subject in need thereof, an effective amount of a compound of claim 1.

5. A method of treating a disease or disorder characterized by an abnormal bone or mineral homeostasis, which comprises administering to a subject in need of treatment thereof an effective amount of a compound of claim 1.

6. A method according to claim 5 wherein the bone or mineral disease or disorder is selected from the group consisting of: osteosarcoma, periodontal disease, fracture healing, osteoarthritis, rheumatoid arthritis, Paget's disease, humoral hypercalcemia malignancy, and osteoporosis.

7. A method according to claim 6 wherein the bone or mineral disease or disorder is osteoporosis.

8. A method of increasing serum parathyroid levels which comprises administering to a subject in need of treatment an effective amount of a compound according to claim 1.

* * * * *